US011518800B2

(12) United States Patent
Monson

(10) Patent No.: US 11,518,800 B2
(45) Date of Patent: Dec. 6, 2022

(54) MUTATIONS THAT DRIVE VH4 ANTIBODY AUTOREACTIVITY

(71) Applicant: The Board of Regents of the University of Texas System, Austin, TX (US)

(72) Inventor: Nancy Monson, Ovilla, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 247 days.

(21) Appl. No.: 16/074,166

(22) PCT Filed: Jan. 31, 2017

(86) PCT No.: PCT/US2017/015755
§ 371 (c)(1),
(2) Date: Jul. 31, 2018

(87) PCT Pub. No.: WO2017/136313
PCT Pub. Date: Aug. 10, 2017

(65) Prior Publication Data
US 2021/0214423 A1 Jul. 15, 2021

Related U.S. Application Data

(60) Provisional application No. 62/289,736, filed on Feb. 1, 2016.

(51) Int. Cl.
*C07K 16/18* (2006.01)
*G01N 33/58* (2006.01)
*G01N 33/68* (2006.01)

(52) U.S. Cl.
CPC ........... *C07K 16/18* (2013.01); *G01N 33/583* (2013.01); *G01N 33/6896* (2013.01); *C07K 2317/565* (2013.01); *C07K 2317/567* (2013.01)

(58) Field of Classification Search
CPC .............. C07K 16/18; C07K 2317/565; C07K 2317/567; C07K 2317/56
See application file for complete search history.

(56) References Cited

U.S. PATENT DOCUMENTS

| 8,394,583 B2 | 3/2013 | Monson |
|---|---|---|
| 2010/0022440 A1 | 1/2010 | Monson |
| 2013/0150308 A1 | 6/2013 | Monson |
| 2013/0172263 A1 | 7/2013 | Monson |
| 2014/0371103 A1 | 12/2014 | Eastman |
| 2014/0371132 A1 | 12/2014 | Monson |
| 2017/0002064 A1 | 1/2017 | Monson |

FOREIGN PATENT DOCUMENTS

| CA | 2769002 | 1/2010 | |
|---|---|---|---|
| WO | WO-2009033743 A1 * | 3/2009 | ............ A61P 25/28 |
| WO | WO 2010/011894 | 1/2010 | |
| WO | WO 2013/059417 | 4/2013 | |
| WO | WO 2013/131074 | 9/2013 | |
| WO | WO 2015/070009 | 5/2015 | |
| WO | WO 2017/197265 | 11/2017 | |

OTHER PUBLICATIONS

Cameron et al., "Potential of a unique antibody gene signature to predict conversion to clinically definite multiple sclerosis", J. Neuroimmunol., 213:123-130, 2009.
International Preliminary Report on Patentability issued in corresponding PCT Application No. PCT/US2017/15755, dated Aug. 16, 2018.
International Search Report and Written Opinion issued in corresponding PCT Application No. PCT/US2017/15755, dated Jun. 20, 2017.
Ligocki et al., "A unique antibody gene signature is prevalent in the central nervous system of patients with multiple sclerosis", J. Neuroimmunol., 226(1-2):192-193, 2010.
Obermeier et al., "Related B cell clones that populate the CSF and CNS of patients with multiple sclerosis produce CSF immunoglobulin", J. Neuroimmunol., 233(1-2):245-248, 2011.

* cited by examiner

*Primary Examiner* — Gregory S Emch
(74) *Attorney, Agent, or Firm* — Parker Highlander PLLC

(57) ABSTRACT

Antibodies exhibiting a specific genetically modified signature associated with certain diseases of the central nervous system, like multiple sclerosis (MS) and clinically isolated syndrome have been identified. These antibodies recognize and bind with certain tissues in the brain and central nervous system and thus are useful as therapeutics, in the production of animal disease models, targets for therapies and as part of assays of the central nervous system.

10 Claims, 5 Drawing Sheets
Specification includes a Sequence Listing.

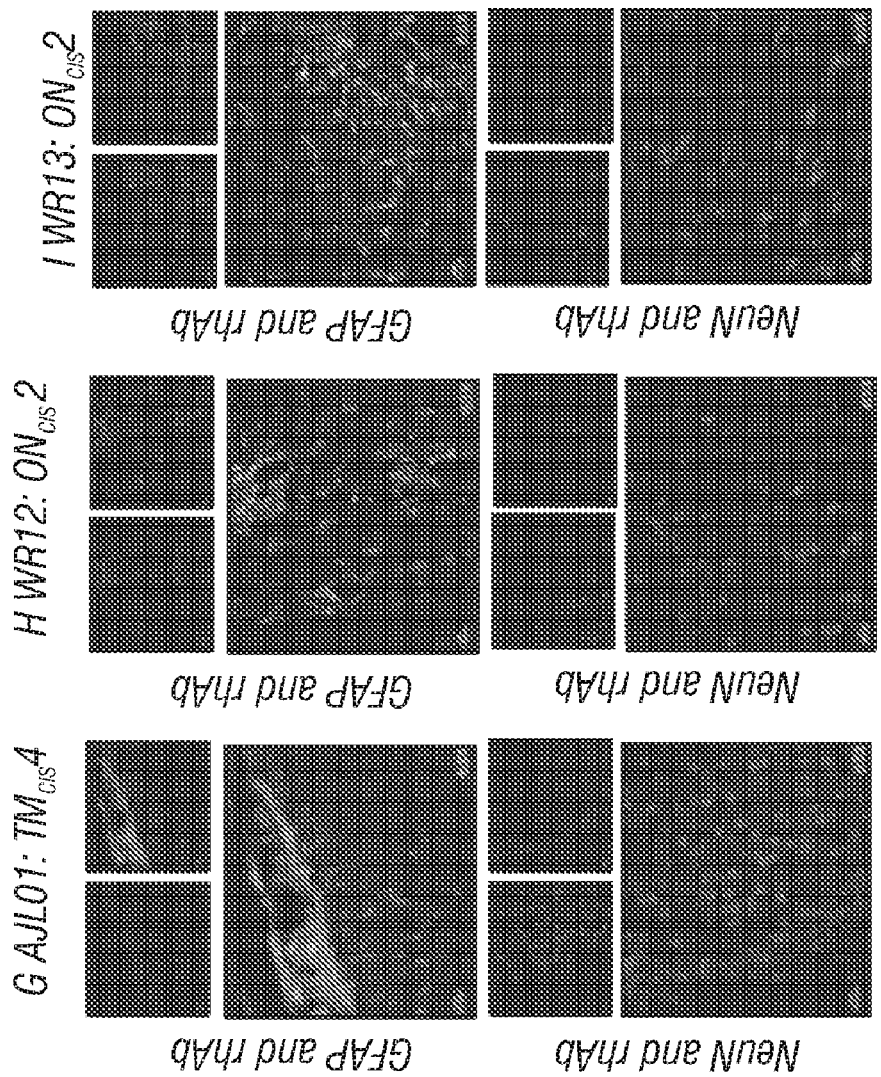

SEQUENCE LISTING

<160> NUMBER OF SEQ ID NOS: 74

<210> SEQ ID NO 1
<211> LENGTH: 100
<212> TYPE: PRT
<213> ORGANISM: Artificial sequence
<220> FEATURE:
<223> OTHER INFORMATION: Synthetic polypeptide

<400> SEQUENCE: 1

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Tyr Tyr Asn Pro Ser
 50                      55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Ala
            100

<210> SEQ ID NO 2
<211> LENGTH: 249
<212> TYPE: DNA
<213> ORGANISM: Artificial sequence
<220> FEATURE:
<223> OTHER INFORMATION: Synthetic oligonucleotide

<400> SEQUENCE: 2
caggtgcagc tgcaggagtc gggcccagga ctggtgaagc cttcacagac cctgtccctc      60
acctgcactg tctctggtgg ctccatcagc agtggtgatt actactggag ttggatccgc     120
cagcccccag ggaagggcct ggagtggatt gggtacatct attacagtgg gagcacctac     180
tacaacccgt ccctcaagct gagctctgtg actgccgcag acacggccgt gtattactgt     240
gccagagca                                                             249

<210> SEQ ID NO 3
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 3

Gln Val Gln Leu Gln Glu Ser Gly Pro Gly Leu Val Lys Pro Ser Gln
  1               5                  10                  15

Thr Leu Ser Leu Thr Cys Thr Val Ser Gly Asp Ser Val Ser Ser Asn
            20                  25                  30

Asp His Tyr Trp Ser Trp Ile Arg Gln Pro Pro Gly Gln Gly Leu Glu
            35                  40                  45

Trp Ile Gly Tyr Ile Ser His Gly Gly Thr Thr Tyr Tyr Asn Pro Ser
 50                      55                  60

Leu Lys Ser Arg Val Thr Met Ser Ile Asp Thr Ser Thr Asn Gln Phe
 65                  70                  75                  80

Ser Leu Arg Val Thr Ser Val Arg Ala Ala Asp Met Ala Val Tyr Phe
                85                  90                  95

Cys Ala Arg Ala Pro Ala Pro Ile Thr Thr Phe Gly Met Val Thr Pro
            100                 105                 110

Val Pro Tyr Phe His Ser
            115

<210> SEQ ID NO 4
<211> LENGTH: 354
<212> TYPE: DNA
<213> ORGANISM: Artificial sequence
<220> FEATURE:
```

<223> OTHER INFORMATION: Synthetic oligonucleotide
<220> FEATURE:
<221> NAME/KEY: misc_feature
<222> LOCATION: (231)..(231)
<223> OTHER INFORMATION: n is a, c, g, or t

<400> SEQUENCE: 4

```
caggtgcagc tgcaggagtc gggcccagga ctggtgaagc cttcacagac cctgtccctc     60
acctgcactg tctctggcga ctccgtcagc agtaatgatc actactggag ttggatccgc    120
cagcccccag ggcagggcct ggagtggatt gggtacatct ctcacggtgg gaccacctac    180
tacaacccgt ccctcaagag tcgagttacc atgtcgatcg acacgtccac naaccagttc    240
tccctgaggg tgacctccgt gcgagccgca gacatggccg tctacttctg tgccagggcc    300
ccggccccta taacgacttt tggaatggtg acaccagtcc cctactttca ctcc          354
```

<210> SEQ ID NO 5
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 5

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Asp Ser Val Ser Ser Asn
             20                  25                  30

Asp His Tyr Trp Ser Trp Ile Arg Gln Pro Pro Gly Gln Gly Leu Glu
         35                  40                  45

Trp Ile Gly Tyr Ile Ser His Gly Gly Thr Thr Tyr Tyr Asn Pro Ser
     50                  55                  60

Leu Lys Ser Arg Val Thr Met Ser Ile Asp Thr Ser Thr Asn Gln Phe
 65                  70                  75                  80

Ser Leu Arg Val Thr Ser Val Arg Ala Ala Asp Met Ala Val Tyr Phe
                 85                  90                  95

Cys Ala Arg Ala Pro Ala Pro Ile Thr Thr Phe Gly Met Val Thr Pro
            100                 105                 110

Val Pro Tyr Phe His Ser
        115
```

<210> SEQ ID NO 6
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 6

```
caggtgcagc tgcaggagtc gggcccagga ctggtgaagc cttcacagac cctgtccctc     60
acctgcactg tctctggcga ctccgtcagc agtaatgatc actactggag ttggatccgc    120
cagcccccag ggcagggcct ggagtggatt gggtacatct ctcacggtgg gaccacctac    180
tacaacccgt ccctcaagag tcgagttacc atgtcgatcg acacgtccac gaaccagttc    240
tccctgaggg tgacctccgt gcgagccgca gacatggccg tctacttctg tgccagggcc    300
ccggccccta taacgacttt tggaatggtg acaccagtcc cctactttca ctcc          354
```

<210> SEQ ID NO 7
<211> LENGTH: 99

<212> TYPE: PRT
<213> ORGANISM: Artificial sequence
<220> FEATURE:
<223> OTHER INFORMATION: Synthetic polypeptide

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 8
<211> LENGTH: 297
<212> TYPE: DNA
<213> ORGANISM: Artificial sequence
<220> FEATURE:
<223> OTHER INFORMATION: Synthetic oligonucleotide

<400> SEQUENCE: 8
caggtgcagc tgcaggagtc gggcccagga ctggtgaagc cttcacagac cctgtccctc    60
acctgtactg tctctggtgg ctccatcagc agtggtggtt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgaga      297

<210> SEQ ID NO 9
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly His Tyr Trp Ser Trp Ile Arg Gln Ser Pro Gly Lys Gly Leu Glu
        35                  40                  45

Trp Ile Gly Asn Val Tyr Tyr Ser Gly Ser Thr Tyr Tyr Thr Pro Ser
    50                  55                  60

Leu Asp Ser Arg Leu Thr Ile Ser Leu Asp Ser Lys Asn Gln Phe
65                  70                  75                  80

Ser Leu Arg Leu Ser Asn Val Thr Val Ala Asp Thr Ala Val Tyr Tyr
                85                  90                  95

Cys Ala Arg Gly Arg Asn Trp Glu Gly Glu Phe Asp Pro Trp Gly Gln
            100                 105                 110

Gly

<210> SEQ ID NO 10
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 10

```
caggtgcagc tgcaggagtc gggcccagga ctggtgaagc cttcacagac cctgtccctc    60
acctgtactg tctctggtgg ctccatcagc agtggtggtc actactggag ctggatccgc   120
cagtccccag ggaagggcct ggagtggatt gggaacgtct attatagtgg aagcacctac   180
tacaccccgt ccctcgacag ccgacttacc atatcattag acacgtctaa gaaccagttc   240
tccctgaggc tgagtaatgt gactgtcgcg gacacggccg tctattactg tgcgagaggt   300
agaaattggg agggcgaatt cgaccccctgg ggccaagga                          339
```

<210> SEQ ID NO 11
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 11

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly
```

<210> SEQ ID NO 12
<211> LENGTH: 294
<212> TYPE: DNA
<213> ORGANISM: Artificial sequence
<220> FEATURE:
<223> OTHER INFORMATION: Synthetic oligonucleotide

<400> SEQUENCE: 12

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg gctggagtg gattggggaa atcaatcata gtggaagcac caactacaac   180
ccgtccctca gagtcgagt caccatatca gtagacacgt ccaagaacca gttctccctg   240
aagctgagct ctgtgaccgc cgcggacacg gctgtgtatt actgtgcgag aggg          294
```

<210> SEQ ID NO 13
<211> LENGTH: 112
<212> TYPE: PRT
<213> ORGANISM: Artificial sequence
<220> FEATURE:

<223> OTHER INFORMATION: Synthetic polypeptide

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Asn Glu Phe
            20                  25                  30

Tyr Trp Ser Trp Ile Arg Gln Pro Ala Arg Lys Gly Leu Glu Trp Ile
        35                  40                  45

Gly Glu Ile Ser His Ser Gly Arg Ala Asn Tyr Asn Pro Ser Leu Lys
    50                  55                  60

Ser Arg Val Thr Leu Ser Val Asp Arg Ser Lys Asn Gln Phe Ser Leu
65                  70                  75                  80

Asn Leu Ser Pro Val Ala Ala Asp Thr Ala Val Tyr Tyr Cys Ala
                85                  90                  95

Arg Arg Glu Ile Val Val Thr Val Arg Gly Arg Ala Phe Asp Ile
            100                 105                 110

<210> SEQ ID NO 14
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 14
caggtgcagc tacagcagtg gggcgcagga ctgttgaagc cttcggagac cctgtccctc    60
acctgcgctg tctatggtgg gtccttcaat gaattctact ggagctggat ccgtcagccc   120
gcacggaagg gcctggagtg gattggagaa atcagtcata gcggaagagc caactacaac   180
ccgtccctca agagtcgcgt caccctgtct gtagacaggt ccaagaacca gttctccctg   240
aacctgagcc ctgtggccgc cgcggacaca gctgtctatt actgtgcgcg acgggagata   300
gtcgtaactg ttcgggggcg tcgtgctttt gatatc                             336

<210> SEQ ID NO 15
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 15

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Leu Ser Gly Tyr
            20                  25                  30

Tyr Trp Ser Trp Ile Arg Gln Pro Pro Gly Lys Gly Pro Glu Trp Ile
        35                  40                  45

Ala Glu Ile Asn His Ser Gly Asp Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Met Ser Ser Val Thr Val Ala Asp Thr Ala Leu Tyr Tyr Cys Ala
                85                  90                  95

Thr Gln Gly Ser Arg Leu Thr Thr Phe Ala Phe Asp Val
            100                 105

<210> SEQ ID NO 16
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 16

```
caggtgcagc tacagcagtg gggcgcagga ctgttgaagc cttcggagac cctgtccctc    60
acctgcgctg tctttggtgg gtccctcagt ggttactact ggagttggat ccgccagccc   120
ccagggaagg ggccggagtg gattgcggaa atcaatcata gtggagatgc aactacaac    180
ccgtccctca agagtcgagt cactatctca gtagacacgt ccaagaacca gttttccctg   240
aagatgagtt ctgtgaccgt cgcagacacg gctttatatt actgtgcgac tcaaggctct   300
aggttgacta cattcgcttt tgatgtg                                       327
```

<210> SEQ ID NO 17
<211> LENGTH: 100
<212> TYPE: PRT
<213> ORGANISM: Artificial sequence
<220> FEATURE:
<223> OTHER INFORMATION: Synthetic polypeptide

<400> SEQUENCE: 17

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp
            100
```

<210> SEQ ID NO 18
<211> LENGTH: 300
<212> TYPE: DNA
<213> ORGANISM: Artificial sequence
<220> FEATURE:
<223> OTHER INFORMATION: Synthetic oligonucleotide

<400> SEQUENCE: 18

```
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaagggact ggagtggatt ggagtatct attatagtgg gagcacctac    180
tacaacccgt ccctcaagag tcgagtcacc atatcagtag acacgtccaa gaaccagttc   240
tccctgaagc tgagctctgt gaccgccgcg gacacggccg tgtattactg tgcgagagat   300
```

<210> SEQ ID NO 19
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 19

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ser
            20                  25                  30

Arg Ser Tyr Trp Gly Trp Ile Arg Gln Pro Pro Gly Lys Gly Leu Glu
        35                  40                  45

Trp Ile Gly Ser Met Tyr Gln Ser Gly Ser Thr Tyr Tyr Ser Pro Ser
    50                  55                  60

Leu Lys Ser Arg Val Thr Ile Ser Met Asp Thr Ser Lys Asn Gln Phe
65                  70                  75                  80

Ser Leu Asn Leu Thr Ser Val Thr Ala Ala Asp Thr Ala Val Tyr Phe
                85                  90                  95

Cys Ala Arg His Ser Asn Pro Gly Thr Ala Asn Lys Leu Arg Leu Gly
            100                 105                 110

Glu Phe Ser Pro
        115

<210> SEQ ID NO 20
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 20
cagctgcagc tgcaggagtc gggcccagga ctggtgaagc cttcggagac cctgtccctc        60
acgtgcactg tctctggtgc ctccatcagc agtagtcgtt cctactgggg ctggatccgc       120
cagcccccag ggaagggct ggagtggatt gggagtatgt atcaaagtgg gagcacttac        180
tacagtccgt ccctcaagag tcgagtcacc atatccatgg acacgtccaa gaaccagttc       240
tccctaaacc tgacgtctgt gaccgccgcg gacacggctg tgtatttctg tgcgagacat       300
tcgaaccccg gaacggcgaa caaattgcgt ttggggagt tttcgccc                     348

<210> SEQ ID NO 21
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 21

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Arg
            20                  25                  30

Asn Asn Tyr Trp Gly Trp Ile Arg Gln Ser Pro Gly Lys Gly Leu Glu
        35                  40                  45

Trp Ile Gly Ser Leu Tyr Tyr Thr Gly Ser Asp Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Val Arg Val Asn Val Asp Asp Phe Trp Ser Gly Leu Gly Gly Ala
            100                 105                 110

Trp Phe Asp Pro
        115

<210> SEQ ID NO 22
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 22
cagctgcagc tgcaggagtc gggcccagga ctggtgaagc cttcggagac cctgtccctc    60
acctgcactg tctctggtgg ctccatcacc agtaggaata actactgggg ctggatccgc   120
cagtccccag ggaagggct ggagtggatt gggagtctct attatactgg agcgactac     180 tacaacccgt ccctcaagag tcgagtcacc atatcggtag acacatcgaa gaaccaattc   240
tccctgaggc tgagttctgt gaccgccgcg gacacggccg tgtattattg tgtcagagtt   300
aacgtagacg acttttggag tggtttaggg ggggcctggt tcgacccc              348

<210> SEQ ID NO 23
<211> LENGTH: 97
<212> TYPE: PRT
<213> ORGANISM: Artificial sequence
<220> FEATURE:
<223> OTHER INFORMATION: Synthetic polypeptide

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 24
<211> LENGTH: 291
<212> TYPE: DNA
<213> ORGANISM: Artificial sequence
<220> FEATURE:
<223> OTHER INFORMATION: Synthetic oligonucleotide

<400> SEQUENCE: 24
caggtgcagc tgcaggagtc gggcccagga ctggtgaagc cttcggagac cctgtccctc    60
acctgcactg tctctggtgg ctccatcagt agttactact ggagctggat ccggcagccc   120
gccgggaagg gactggagtg gattgggcgt atctatacca gtgggagcac caactacaac   180
ccctccctca agagtcgagt caccatgtca gtagacacgt ccaagaacca gttctccctg   240
aagctgagct ctgtgaccgc cgcggacacg gccgtgtatt actgtgcgag a            291

<210> SEQ ID NO 25
<211> LENGTH: 111

<212> TYPE: PRT
<213> ORGANISM: Artificial sequence
<220> FEATURE:
<223> OTHER INFORMATION: Synthetic polypeptide

<400> SEQUENCE: 25

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ala Val Ser Asn Tyr
            20                  25                  30

Tyr Trp Ser Trp Ile Arg Gln Ser Ala Gly Lys Gly Leu Glu Trp Leu
        35                  40                  45

Gly Arg Ile Tyr Ile Asn Gly Thr Thr Tyr Tyr Asn Pro Ser Leu Arg
    50                  55                  60

Ser Arg Val Ser Met Ser Val Asp Thr Ser Lys Gly Gln Phe Ser Leu
65                  70                  75                  80

Arg Leu Thr Ser Val Thr Ala Ala Asp Thr Ala Ile Tyr Tyr Cys Ala
                85                  90                  95

Arg Trp Gly Ala Leu Leu Gly Asp Tyr Tyr Tyr Gly Leu Asp Val
            100                 105                 110

<210> SEQ ID NO 26
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 26
caggtgcagc tgcaggagtc gggcccagga ctggtgaagc cttcggagac cctgtccctc      60
acgtgcagtg tctctggtgg cgccgtcagt aattactact ggagttggat ccggcagtcc     120
gccgggaagg gactggagtg gcttgggcgg atctatatca atggaactac ttactacaac     180
ccctccctca ggagccgggt ctccatgtca gttgacacgt ccaagggcca gttctccctg     240
aggttgacct ctgtgaccgc cgcggacacg gccatatatt attgtgcgag atggggtgcc     300
ctattgggcg actactatta cggtttggac gtc                                 333

<210> SEQ ID NO 27
<211> LENGTH: 115
<212> TYPE: PRT
<213> ORGANISM: Artificial sequence
<220> FEATURE:
<223> OTHER INFORMATION: Synthetic polypeptide

<400> SEQUENCE: 27

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Asn Asn
            20                  25                  30

Lys Trp Trp Asn Trp Val Arg Gln Ser Pro Gly Lys Gly Leu Glu Trp
        35                  40                  45

Ile Gly Glu Ile Tyr His Ser Gly Gly Thr Asn Tyr Asn Pro Ser Leu
    50                  55                  60

Lys Ser Arg Val Thr Ile Ser Val Asp Lys Ser Lys Asn Leu Phe Ser
65                  70                  75                  80

Leu Lys Leu Ser Ser Val Thr Ala Ala Asp Thr Ala Val Tyr Tyr Cys
                85                  90                  95

Ala Ser Ala Thr Thr Met Val Arg Gly Leu Ser Leu Tyr Tyr Tyr Gly

<210> SEQ ID NO 28
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 28

```
caggtgcagc tgcaggagtc gggcccagga ctggtgaagc cttcggggac cctgtccctc    60
acctgcgctg tctctggtgg ctccatcagc aataataagt ggtggaattg ggtccgccag   120
tccccaggga aggggctgga gtggattggg gaaatctatc atagtggggg caccaactac   180
aacccgtccc tcaagagtcg agtcaccata tcggtagaca gtccaagaa cctgttctcc   240
ctgaagctga gctctgtgac cgccgcggac acggccgtgt attactgtgc gagtgcgact   300
actatggttc ggggactgag tctttactac tacggtctgg acgtc                  345
```

<210> SEQ ID NO 29
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 29

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Asn Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Glu

<210> SEQ ID NO 30
<211> LENGTH: 294
<212> TYPE: DNA
<213> ORGANISM: Artificial sequence
<220> FEATURE:
<223> OTHER INFORMATION: Synthetic oligonucleotide

<400> SEQUENCE: 30

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca tgggagcac caactacaac   180
ccctccctca agagtcgagt caccatatca gtagacacgt ccaagaacca gttctccctg   240
aagctgagct ctgtgaccgc tgcggacacg gccgtgtatt actgtgcgag agaa        294
```

<210> SEQ ID NO 31

```
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 31
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Asn Gly Asn Ile Asn Tyr Asn Pro Ser Leu Lys
    50                  55                  60

Ser Arg Val Thr Ile Ser Arg Asp Met Ser Lys Asn Gln Phe Ser Leu
65                  70                  75                  80

Asn Leu Arg Ser Val Thr Ala Ala Asp Thr Ala Val Tyr Tyr Cys Gly
                85                  90                  95

Ile Gly Tyr Ser Ala Val Ala Ala Gly Thr Val Asp Tyr
            100                 105

```
<210> SEQ ID NO 32
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 32
```

| | | | | | |
|---|---|---|---|---|---|
| caggtgcagc | tgcaggagtc | gggcccagga | ctggtgaagc | cttcggagac | cctgtccctc | 60 |
| acctgcactg | tctctggtgg | ctccatcaac | aactattact | ggagttggat | ccggcagccc | 120 |
| ccagggaagg | gactggagtg | gattggttat | atctattaca | atgggaatat | taattacaac | 180 |
| ccttccctca | agagtcgagt | caccatatca | agagacatgt | ccaagaacca | gttctccctg | 240 |
| aacctgcggt | ctgtgaccgc | tgcggacacg | gccgtgtatt | actgtggaat | tggatatagt | 300 |
| gcggtggcag | ctggtacagt | tgactac | | | | 327 |

```
<210> SEQ ID NO 33
<211> LENGTH: 95
<212> TYPE: PRT
<213> ORGANISM: Artificial sequence
<220> FEATURE:
<223> OTHER INFORMATION: Synthetic polypeptide

<400> SEQUENCE: 33
```

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 34
<211> LENGTH: 285
<212> TYPE: DNA
<213> ORGANISM: Artificial sequence
<220> FEATURE:
<223> OTHER INFORMATION: Synthetic oligonucleotide

<400> SEQUENCE: 34

```
gccatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaggctc ctaaactcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt accct                   285
```

<210> SEQ ID NO 35
<211> LENGTH: 97
<212> TYPE: PRT
<213> ORGANISM: Artificial sequence
<220> FEATURE:
<223> OTHER INFORMATION: Synthetic polypeptide

<400> SEQUENCE: 35

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Gly
            20                  25                  30

Leu Ala Trp Tyr Gln Gln Glu Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Ala Ile Asp Phe Thr Leu Thr Ile Ser Ser Leu Gln Pro
65                  70                  75                  80

Glu Asp Phe Ala Thr Tyr Tyr Cys Gln Gln Phe Asn Ser Thr Phe Pro Tyr
                85                  90                  95

Thr

<210> SEQ ID NO 36
<211> LENGTH: 291
<212> TYPE: DNA
<213> ORGANISM: Artificial sequence
<220> FEATURE:
<223> OTHER INFORMATION: Synthetic oligonucleotide

<400> SEQUENCE: 36

```
gccatccagt tgacccagtc tccatcctcc ctgtctgcat ctgtgggaga cagagtcacc    60
atcacttgcc gggcaagtca gggcattagc agtggtttag cctggtatca gcaggaacca   120
gggaaagctc ctaaactcct gatctatgat gcctccactt tggaaagtgg ggtcccatca   180
agattcagcg gcagtggatc tgcaatagat ttcactctca ccatcagcag tctgcagcct   240
gaagattttg caacttatta ctgtcaacag tttaatactt cccgtatac t            291
```

<210> SEQ ID NO 37
<211> LENGTH: 95
<212> TYPE: PRT
<213> ORGANISM: Artificial sequence
<220> FEATURE:
<223> OTHER INFORMATION: Synthetic polypeptide

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Gln Gln Tyr Asp Asn Leu Pro
                85                  90                  95

<210> SEQ ID NO 38
<211> LENGTH: 285
<212> TYPE: DNA
<213> ORGANISM: Artificial sequence
<220> FEATURE:
<223> OTHER INFORMATION: Synthetic oligonucleotide

<400> SEQUENCE: 38
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatattg caacatatta ctgtcaacag tatgataatc tccct                   285

<210> SEQ ID NO 39
<211> LENGTH: 97
<212> TYPE: PRT
<213> ORGANISM: Artificial sequence
<220> FEATURE:
<223> OTHER INFORMATION: Synthetic polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Phe Gln Gln Gln Pro Gly Lys Ala Pro Lys Leu Leu Ile
        35                  40                  45

Tyr Asp Ala Ser Lys Leu Gln Met Gly Val Pro Ser Arg Phe Ser Gly
    50                  55                  60

Ser Ala Ser Gly Thr Asp Phe Thr Phe Thr Ile Ser Ser Leu Gln Pro
65              70                  75                  80

Glu Asp Ile Gly Thr Tyr Tyr Cys Gln Gln Tyr Tyr Asn Leu Pro Tyr
                85                  90                  95

Thr

<210> SEQ ID NO 40
<211> LENGTH: 291
<212> TYPE: DNA
<213> ORGANISM: Artificial sequence
<220> FEATURE:
<223> OTHER INFORMATION: Synthetic oligonucleotide

<400> SEQUENCE: 40

```
gacatccaga tgacccagtc tccatcctcc ctgtctgcat ctgtaggaga cagagtcacc    60
atcacttgcc aggcgagtca ggacattaac aactatttaa attggtttca gcagcaacca   120
gggaaagccc ctaagctgct gatctacgat gcatccaaat tgcaaatggg ggtcccatca   180
aggttcagtg gaagtgcatc tgggacagat tttactttta ccatcagcag cctgcagcct   240
gaagatattg gcacatatta ctgtcaacag tattataatc tcccgtacac t            291
```

<210> SEQ ID NO 41
<211> LENGTH: 95
<212> TYPE: PRT
<213> ORGANISM: Artificial sequence
<220> FEATURE:
<223> OTHER INFORMATION: Synthetic polypeptide

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 42
<211> LENGTH: 285
<212> TYPE: DNA
<213> ORGANISM: Artificial sequence
<220> FEATURE:
<223> OTHER INFORMATION: Synthetic oligonucleotide

<400> SEQUENCE: 42

```
gacatccaga tgacccagtc tccatcctcc ctgtctgcat ctgtaggaga cagagtcacc    60
atcacttgcc gggcaagtca gagcattagc agctctgtaa attggtttca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccct                  285
```

<210> SEQ ID NO 43
<211> LENGTH: 97
<212> TYPE: PRT
<213> ORGANISM: Artificial sequence
<220> FEATURE:
<223> OTHER INFORMATION: Synthetic polypeptide

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Val Asn Trp Phe Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60
```

```
Ser Gly Ser Gly Thr Asp Phe Thr Leu Thr Val Ser Ser Leu Gln Pro
 65                  70                  75                  80

Glu Asp Phe Ala Thr Tyr Tyr Cys Gln Gln Ser Tyr Ser Pro Pro Arg
                 85                  90                  95

Thr

<210> SEQ ID NO 44
<211> LENGTH: 291
<212> TYPE: DNA
<213> ORGANISM: Artificial sequence
<220> FEATURE:
<223> OTHER INFORMATION: Synthetic oligonucleotide

<400> SEQUENCE: 44
gacatccaga tgacccagtc tccatcctcc ctgtctgcat ctgtaggaga cagagtcacc    60
atcacttgcc gggcaagtca gggcattagc agctctgtaa attggtttca gcagaaacca   120
gggaaagccc ctgaactcct gatctatgct gcatccactt tgcaaagtgg ggtcccatca   180
agattcagtg gcagtggatc tgggacagat ttcactctca ccgtcagcag tctgcaacct   240
gaagattttg caacttacta ctgtcagcag agttacagtc ccctcgaac t             291

<210> SEQ ID NO 45
<211> LENGTH: 100
<212> TYPE: PRT
<213> ORGANISM: Artificial sequence
<220> FEATURE:
<223> OTHER INFORMATION: Synthetic polypeptide

<400> SEQUENCE: 45

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100

<210> SEQ ID NO 46
<211> LENGTH: 300
<212> TYPE: DNA
<213> ORGANISM: Artificial sequence
<220> FEATURE:
<223> OTHER INFORMATION: Synthetic oligonucleotide

<400> SEQUENCE: 46
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca atctccacaa ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
```

<210> SEQ ID NO 47
<211> LENGTH: 102
<212> TYPE: PRT
<213> ORGANISM: Artificial sequence
<220> FEATURE:
<223> OTHER INFORMATION: Synthetic polypeptide

<400> SEQUENCE: 47

```
Asp Ile Val Met Thr Gln Ser Pro Leu Ser Leu Pro Val Thr Pro Gly
1               5                   10                  15

Glu Pro Ala Ser Ile Ser Cys Arg Ser Thr Gln Ser Leu Leu His Ser
            20                  25                  30

Asn Glu Tyr Ile Tyr Leu Asp Trp Tyr Val Gln Lys Pro Gly Gln Ser
        35                  40                  45

Pro Gln Leu Leu Ile Phe Leu Ala Ser Asn Arg Ala Ser Gly Val Pro
    50                  55                  60

Asp Arg Phe Ser Gly Ser Ala Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Glu Ala Pro Trp Thr
            100
```

<210> SEQ ID NO 48
<211> LENGTH: 306
<212> TYPE: DNA
<213> ORGANISM: Artificial sequence
<220> FEATURE:
<223> OTHER INFORMATION: Synthetic oligonucleotide

<400> SEQUENCE: 48

```
gatattgtga tgactcagtc tccactctcc ctgcccgtca cccctggaga gccggcctcc    60
atctcctgca ggtctactca gagcctccta cacagtaatg aatacattta tttggattgg   120
tacgtgcaga agccagggca gtctccacaa ctcctgatct ttttggcttc taatcgggcc   180
tccggggtcc ctgacaggtt cagtggcagt gcatcaggca cagattttac actgaaaatc   240
agcagagtgg aggctgagga tgttggggtt tattactgca tgcaagctct agaagctccg   300
tggacg                                                              306
```

<210> SEQ ID NO 49
<211> LENGTH: 102
<212> TYPE: PRT
<213> ORGANISM: Artificial sequence
<220> FEATURE:
<223> OTHER INFORMATION: Synthetic polypeptide

<400> SEQUENCE: 49

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Ser Trp Tyr Leu Gln Lys Pro Gly Gln Ser
        35                  40                  45

Pro Gln Leu Leu Ile Phe Ser Ser Ile Arg Ala Ser Gly Val Pro
    50                  55                  60

Asp Arg Phe Ser Gly Ser Gly Ser Gly Thr Asp Phe Thr Leu Thr Ile
65                  70                  75                  80
```

Asn Arg Val Glu Ala Glu Asp Val Gly Val Tyr Tyr Cys Met Gln Ala
            85                  90                  95

Leu Gln Thr Pro Leu Thr
            100

<210> SEQ ID NO 50
<211> LENGTH: 306
<212> TYPE: DNA
<213> ORGANISM: Artificial sequence
<220> FEATURE:
<223> OTHER INFORMATION: Synthetic oligonucleotide

<400> SEQUENCE: 50
gatattgtga tgactcagtc tccactctcc ctgcccgtca cccctggaga gccggcctcc     60
atctcctgca ggtctagtca gagcctcctc catagtaatg gatacaacta tttgagttgg    120
tacctgcaga agccagggca gtctccacaa ctcctgatct tttcgagttc tattcgggcc    180
tccggggtcc ctgacaggtt cagtggcagt ggatcaggca cagattttac actgacaatc    240
aacagagtgg aggctgagga tgttggagtt tattactgca tgcaggctct acaaactccg    300
ctcact                                                               306

<210> SEQ ID NO 51
<211> LENGTH: 102
<212> TYPE: PRT
<213> ORGANISM: Artificial sequence
<220> FEATURE:
<223> OTHER INFORMATION: Synthetic polypeptide

<400> SEQUENCE: 51

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Ser Trp Tyr Leu Gln Lys Pro Gly Gln Ser
        35                  40                  45

Pro Gln Leu Leu Ile Phe Ser Ser Ser Ile Arg Ala Ser Gly Val Pro
    50                  55                  60

Asp Arg Phe Ser Gly Ser Gly Ser Gly Thr Asp Phe Thr Leu Thr Ile
65                  70                  75                  80

Asn Arg Val Glu Ala Glu Asp Val Gly Val Tyr Tyr Cys Met Gln Ala
            85                  90                  95

Leu Gln Thr Pro Leu Thr
            100

<210> SEQ ID NO 52
<211> LENGTH: 306
<212> TYPE: DNA
<213> ORGANISM: Artificial sequence
<220> FEATURE:
<223> OTHER INFORMATION: Synthetic oligonucleotide

<400> SEQUENCE: 52
gatattgtga tgactcagtc tccactctcc ctgcccgtca cccctggaga gccggcctcc     60
atctcctgca ggtctagtca gagcctcctc catagtaatg gatacaacta tttgagttgg    120
tacctgcaga agccagggca gtctccacaa ctcctgatct tttcgagttc tattcgggcc    180
tccggggtcc ctgacaggtt cagtggcagt ggatcaggca cagattttac actgacaatc    240
aacagagtgg aggctgagga tgttggagtt tattactgca tgcaggctct acaaactccg    300
ctcact                                                                306

<210> SEQ ID NO 53
<211> LENGTH: 100
<212> TYPE: PRT
<213> ORGANISM: Artificial sequence
<220> FEATURE:
<223> OTHER INFORMATION: Synthetic polypeptide

<400> SEQUENCE: 53

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 54
<211> LENGTH: 300
<212> TYPE: DNA
<213> ORGANISM: Artificial sequence
<220> FEATURE:
<223> OTHER INFORMATION: Synthetic oligonucleotide

<400> SEQUENCE: 54
gatattgtga tgacccagac tccactctct ctgtccgtca cccctggaca gccggcctcc     60
atctcctgca agtctagtca gagcctcctg catagtgatg gaaagaccta tttgtattgg    120
tacctgcaga agccaggcca gtctccacag ctcctgatct atgaagtttc caaccggttc    180
tctggagtgc cagataggtt cagtggcagc gggtcaggga cagatttcac actgaaaatc    240
agccgggtgg aggctgagga tgttggggtt tattactgca tgcaaagtat acagcttcct    300

<210> SEQ ID NO 55
<211> LENGTH: 102
<212> TYPE: PRT
<213> ORGANISM: Artificial sequence
<220> FEATURE:
<223> OTHER INFORMATION: Synthetic polypeptide

<400> SEQUENCE: 55

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr His Leu Tyr Trp Tyr Leu Gln Lys Pro Gly Gln Ser
        35                  40                  45

Pro Gln Ser Leu Ile Tyr Glu Val Ser Lys Arg Phe Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ser
                85                  90                  95

Ala Gln Leu Pro Tyr Thr
            100

<210> SEQ ID NO 56
<211> LENGTH: 306
<212> TYPE: DNA
<213> ORGANISM: Artificial sequence
<220> FEATURE:
<223> OTHER INFORMATION: Synthetic oligonucleotide

<400> SEQUENCE: 56
gatattgtga tgacccagac tccactctct ttgtccgtca cccctggaca gccggcctcc      60
atctcctgca aatctagtca gagcctcctg atagtgatg gaaagaccca tttgtactgg     120
tacctgcaga agccaggcca gtctccacag tccctgatct atgaagtttc taaacggttc     180
tctggagtgc cagataggtt cactggcagc gggtcaggga cagatttcac actgaaaatc     240
agccgggtgg aggctgagga tgttgggctt attactgca tgcaaagtgc acagcttccg     300
tacact                                                                306

<210> SEQ ID NO 57
<211> LENGTH: 96
<212> TYPE: PRT
<213> ORGANISM: Artificial sequence
<220> FEATURE:
<223> OTHER INFORMATION: Synthetic polypeptide

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 58
<211> LENGTH: 288
<212> TYPE: DNA
<213> ORGANISM: Artificial sequence
<220> FEATURE:
<223> OTHER INFORMATION: Synthetic oligonucleotide

<400> SEQUENCE: 58
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacct                  288

<210> SEQ ID NO 59
<211> LENGTH: 98
<212> TYPE: PRT

<213> ORGANISM: Artificial sequence
<220> FEATURE:
<223> OTHER INFORMATION: Synthetic polypeptide

<400> SEQUENCE: 59

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Leu Ile Gly Ser
            20                  25                  30
Phe Leu Ala Trp Tyr Gln Gln Lys Pro Gly Gln Ala Pro Arg Leu Leu
        35                  40                  45
Ile Tyr His Thr Ser Asn Arg Ala Ser Gly Ile Pro Asp Arg Phe Ser
    50                  55                  60
Gly Gly Gly Phe Gly Thr Asp Phe Thr Leu Thr Ile Ser Arg Leu Glu
65                  70                  75                  80
Pro Glu Asp Phe Ala Val Tyr Tyr Cys Gln Gln Tyr Asp Ser Pro
                85                  90                  95
Ile Thr
```

<210> SEQ ID NO 60
<211> LENGTH: 294
<212> TYPE: DNA
<213> ORGANISM: Artificial sequence
<220> FEATURE:
<223> OTHER INFORMATION: Synthetic oligonucleotide

<400> SEQUENCE: 60

```
gaaattgtgt tgacgcagtc tccaggcacc ctgtctttgt ctccagggga aagagccacc     60
ctctcctgca gggccagtca gagtcttatc ggcagcttct tagcctggta ccagcagaaa    120
cctggccagg ctcccaggct cctcatctat catacatcca acagggcctc tggcatccca    180
gacaggttca gtggcggtgg gtttgggaca gacttcactc tcaccatcag cagactggag    240
cctgaagatt ttgcagttta ttactgtcaa cagtatgata gctcaccgat cacc          294
```

<210> SEQ ID NO 61
<211> LENGTH: 99
<212> TYPE: PRT
<213> ORGANISM: Artificial sequence
<220> FEATURE:
<223> OTHER INFORMATION: Synthetic polypeptide

<400> SEQUENCE: 61

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Asp
            20                  25                  30
Ser Leu Ala Trp Tyr Gln Gln Lys Pro Gly Gln Thr Pro Arg Leu Leu
        35                  40                  45
Ile Tyr His Thr Ser Thr Arg Ala Ala Gly Ile Pro Asp Arg Phe Ser
    50                  55                  60
Gly Thr Gly Ser Gly Thr Asp Phe Thr Leu Thr Ile Ala Arg Leu Glu
65                  70                  75                  80
Pro Glu Asp Phe Ala Val Tyr Tyr Cys Gln His Tyr Gly Arg Ser Ser
                85                  90                  95
Leu Phe Thr
```

<210> SEQ ID NO 62
<211> LENGTH: 297

<212> TYPE: DNA
<213> ORGANISM: Artificial sequence
<220> FEATURE:
<223> OTHER INFORMATION: Synthetic oligonucleotide

<400> SEQUENCE: 62

```
gaaattgtgt tgacgcagtc tccaggcacc ctgtctttgt ctccagggga aagagccacc    60
ctctcctgca gggccagtca gagtgttagc agcgactcct tagcctggta ccagcagaaa   120
cctggccaga ctcccaggct cctcatttat catacatcca ccagggccgc tggcatccca   180
gacaggttca gtggcactgg gtctgggaca gacttcactc tcaccatcgc cagactggag   240
cctgaagatt ttgcagtcta ttactgtcag cactatggtc ggtcatccct attcacc     297
```

<210> SEQ ID NO 63
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 63

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Leu Ile Gly Ser
            20                  25                  30
Phe Leu Ala Trp Tyr Gln Gln Lys Pro Gly Gln Ala Pro Arg Leu Leu
        35                  40                  45
Ile Tyr His Thr Ser Asn Arg Ala Ser Gly Ile Pro Asp Arg Phe Ser
    50                  55                  60
Gly Gly Gly Phe Gly Thr Asp Phe Thr Leu Thr Ile Ser Arg Leu Glu
65                  70                  75                  80
Pro Glu Asp Phe Ala Val Tyr Tyr Cys Gln Gln Tyr Asp Ser Ser Pro
                85                  90                  95
Ile Thr
```

<210> SEQ ID NO 64
<211> LENGTH: 294
<212> TYPE: DNA
<213> ORGANISM: Artificial sequence
<220> FEATURE:
<223> OTHER INFORMATION: Synthetic oligonucleotide

<400> SEQUENCE: 64

```
gaaattgtgt tgacgcagtc tccaggcacc ctgtctttgt ctccagggga aagagccacc    60
ctctcctgca gggccagtca gagtcttatc ggcagcttct agcctggta ccagcagaaa    120
cctggccagg ctcccaggct cctcatctat catacatcca acaggcctc tggcatccca    180
gacaggttca gtggcggtgg gtttgggaca gacttcactc tcaccatcag cagactggag   240
cctgaagatt ttgcagttta ttactgtcaa cagtatgata gctcaccgat cacc          294
```

<210> SEQ ID NO 65
<211> LENGTH: 8
<212> TYPE: PRT
<213> ORGANISM: Artificial sequence
<220> FEATURE:
<223> OTHER INFORMATION: Synthetic peptide

<400> SEQUENCE: 65

```
Gly Gly Ala Val Ser Asn Tyr Tyr
1               5
```

```
<210> SEQ ID NO 66
<211> LENGTH: 7
<212> TYPE: PRT
<213> ORGANISM: Artificial sequence
<220> FEATURE:
<223> OTHER INFORMATION: Synthetic peptide

<400> SEQUENCE: 66

Ile Tyr Ile Asn Gly Thr Thr
1               5

<210> SEQ ID NO 67
<211> LENGTH: 16
<212> TYPE: PRT
<213> ORGANISM: Artificial sequence
<220> FEATURE:
<223> OTHER INFORMATION: Synthetic peptide

<400> SEQUENCE: 67

Ala Arg Trp Gly Ala Leu Leu Gly Asp Tyr Tyr Tyr Gly Leu Asp Val
1               5                   10                  15

<210> SEQ ID NO 68
<211> LENGTH: 11
<212> TYPE: PRT
<213> ORGANISM: Artificial sequence
<220> FEATURE:
<223> OTHER INFORMATION: Synthetic peptide

<400> SEQUENCE: 68

Gln Ser Leu Leu His Ser Asn Glu Tyr Ile Tyr
1               5                   10

<210> SEQ ID NO 69
<211> LENGTH: 9
<212> TYPE: PRT
<213> ORGANISM: Artificial sequence
<220> FEATURE:
<223> OTHER INFORMATION: Synthetic peptide

<400> SEQUENCE: 69

Met Gln Ala Leu Glu Ala Pro Trp Thr
1               5

<210> SEQ ID NO 70
<211> LENGTH: 8
<212> TYPE: PRT
<213> ORGANISM: Artificial sequence
<220> FEATURE:
<223> OTHER INFORMATION: Synthetic peptide

<400> SEQUENCE: 70

Gly Gly Ser Ile Asn Asn Tyr Tyr
1               5

<210> SEQ ID NO 71
<211> LENGTH: 7
<212> TYPE: PRT
<213> ORGANISM: Artificial sequence
<220> FEATURE:
<223> OTHER INFORMATION: Synthetic peptide

<400> SEQUENCE: 71

Ile Tyr Tyr Asn Gly Asn Ile
1               5
```

```
<210> SEQ ID NO 72
<211> LENGTH: 14
<212> TYPE: PRT
<213> ORGANISM: Artificial sequence
<220> FEATURE:
<223> OTHER INFORMATION: Synthetic peptide

<400> SEQUENCE: 72

Gly Ile Gly Tyr Ser Ala Val Ala Ala Gly Thr Val Asp Tyr
1               5                   10

<210> SEQ ID NO 73
<211> LENGTH: 6
<212> TYPE: PRT
<213> ORGANISM: Artificial sequence
<220> FEATURE:
<223> OTHER INFORMATION: Synthetic peptide

<400> SEQUENCE: 73

Gln Gly Ile Ser Ser Gly
1               5

<210> SEQ ID NO 74
<211> LENGTH: 9
<212> TYPE: PRT
<213> ORGANISM: Artificial sequence
<220> FEATURE:
<223> OTHER INFORMATION: Synthetic peptide

<400> SEQUENCE: 74

Gln Gln Phe Asn Thr Phe Pro Tyr Thr
1               5
```

MUTATIONS THAT DRIVE VH4 ANTIBODY AUTOREACTIVITY

This application is a national phase application under 35 U.S.C. § 371 of International Application No. PCT/US2017/015755, filed Jan. 31, 2017, which claims benefit of priority to U.S. Provisional Application Ser. No. 62/289,736, filed Feb. 1, 2016, the entire contents of each of which are hereby incorporated by reference.

BACKGROUND

1. Field

The disclosed subject matter relates to fields of pathology, immunology, molecular biology and neuroscience. More particularly, the present disclosure relates to antibodies exhibiting mutations in VH4 codons that correlate with binding to neurons or astrocytes in the brain, and uses therefor.

2. Background

B cells have been implicated in multiple sclerosis (MS) and have been recognized to play a role in MS pathology in addition to the well-accepted pathological role of T cells. B cells and antibodies are present in both the cerebrospinal fluid (CSF) and the central nervous system (CNS) of patients with MS and clinically isolated syndrome (CIS) patients who are at high risk of developing MS. The most common form of MS lesion is characterized by deposition of antibodies and complement (Lucchinetti et al., 2000), and plasmapheresis treatment of patients harboring these lesions leads to symptom improvement (Keegan et al., 2005). In fact, elevated B cells in the CSF correlates with lesion activity on MRI (Cepok et al., 2005) and both increased intrathecal immunoglobulin synthesis (Sellebjerg et al., 2000) and complement activation (Sellebjerg et al., 1998) are also associated with a more aggressive disease course. Collectively these findings implicate a pathological role for antibodies in the pathoetiology of MS.

The inventor's laboratory has previously discovered a biomarker for conversion from CIS to clinically definite MS (CDMS) in the antibody genetics of $V_H4$-utilizing B cells in the CSF, termed the antibody gene signature (AGS) (Cameron et al., 2009). She also found that B cells isolated from CNS lesions harbor the AGS (Ligocki et al., 2010). This shared pattern of somatic hypermutation at 6 codons along the $V_H4$ gene implicates that the B cell pools are recognizing a shared set of antigens in the MS disease state that are not recognized by B cells in healthy individuals. However, the existence of such a phenomenon, and identification of the antigens to which these antibodies bind, have been demonstrated. During this analysis, it became apparent that somatic hypermutations to particular amino acid residues associate with binding to neurons, astrocytes, both, or neither. This phenomenon is the subject of the current patent application.

SUMMARY

Thus, in accordance with the present disclosure, there is provided art demonstrating that antibodies cloned from B cells in the cerebrospinal fluid of MS patients bind to neurons and astrocytes; the sequences of these antibody heavy (and light) chains; and the decision chart used to predict binding to each cell type based on the amino acid change that occurs at particular codons within the VH4 genes.

Ther is provided a recombinant antibody or antigen-binding fragment thereof, including anti-idiotypic Abs and other disruptive constructs, wherein the recombinant antibody or fragment binds to an antigen in human brain gray matter that is recognized by a VH4-comprising antibody having a mutation with respect to the germline sequence at codon positions selected from 40 and 81, and optionally containing mutations at 31B, 32, 56, 57, 60, and/or 89. The recombinant antibody or fragment may have mutations at both codon position 40 and codon position 81, or at either codon position 40 or codon position 81. The recombinant antibody or fragment may have a serine at codon position 40, and/or may have an asparagine at codon position 81. The antibody or fragment may have heavy chain CDRs and light chain CDRs selected from Table 1 or 2. The antibody or fragment may be linked to a toxin, to a drug or prodrug, or to a label, such as a chromophore, fluorophore, chemilluminescent compound, dye, contrast agent, radioabel.

Also provide is a method of detecting immune mediated neurological diseases in a subject comprising (a) administering to said subject a recombinant antibody or fragment as described above; and (b) detecting the localization of said antibody in a neuronal tissue of said subject. The subject may be a human subject, or a non-human mammalian subject. The antibody or fragment may be is conjugated to a label. The antibody or fragment may be detected by the binding of a labeled secondary argent to said antibody. The label may be a chromophore, fluorophore, chemilluminescent compound, dye, contrast agent, radioabel.

In another embodiment, there is provided a method of preparing a neurologic disease animal model comprising (a) providing a non-human mammalian subject; and (b) administering to said subject one or more recombinant antibodies or fragments as defined above. The subject may be a mouse, hamster, rat or rabbit. The method may further comprising repeating step (b) at least once, and the repeating of step (b) may continue until a disease-like event is observed, so long as said animal is alive. The neurologic disease may be multiple sclerosis.

There is also provided a method of preparing a neurologica disease animal model comprising preparing a non-human mammalian subject that contains a transgenic B cell expressing a recombinant antibody or fragment thereof as defined above. The subject may be a mouse, hamster, rat or rabbit. Preparing may comprise administering a B cell expressing said antibody to said subject, wherein said B cell has been transformed with an expression construct that encodes said antibody under the control of a promoter active in said B cell. The B cells may be syngeneic B-cells. Preparing may alternatively comprise generating said non-human mammalian subject such that cells of said subject comprise a germ line insert of an exogenous expression construct that encodes said recombinant antibody or fragment thereof under the control of a promoter active in B cells of said subject. The neurologic disease may be multiple sclerosis.

In a further embodiment, there is provided a method of treating an immune mediated disease in a patient comprising administering to said subject an agent or subjecting said subject to a therapy that reduces the amount or function of an antibody as defined above. The agent may comprise an anti-idiotypic antibody to said antibody as set forth in claims 1-5, an antigen fragment that binds to said antibody, an siRNA that reduces said antibody's expression, or a non-Fc containing antibody that competes with said antibody. The therapy may be B-cell ablation that reduces B-cells producing said antibody. The therapy may comprise physical removal of B-cells producing said antibody or physical removal of said antibody. The method may further comprising administering to said subject one or more traditional MS therapies. The agent may be administered systemically, or through a route that targets neuronal tissue.

In still a further embodiment, there is provided a method of identifying B cell producing brain-reactive antibodies in a subject comprising (a) obtaining an antibody-containing sample from a subject; (b) determining the presence of an antibody or fragment as defined above in said sample, wherein the presence of the antibody or fragment 5 in said sample identifies said B cell. The method may further comprise treating said subject for disease when the antibody or fragment is identified. The method may also further comprise monitoring said subject for disease change when the antibody or fragment is identified. The sample may be cerebrospinal fluid, blood or other human samples that may contain antibody.

In an additional embodiment, there is provided a method for treating a neurodegenerative disorder in a patient, comprising administering to said patient an agent that reduces binding of the antibody as defined above. The agent may be administered such that the antibody contacting of the antigen in human grey matter in reduced. The agent may be an anti-idiotypic antibody, an antibody or antigen-binding portion thereof, a peptide, an aptamer, or a small molecule.

In some embodiments, other properties of the antibodies can be as described in U.S. Pat. No. 8,394,583 or as described herein with respect to preferrential usage of germline sequences. U.S. Pat. No. 8,394,583 is hereby incorporated by reference in its entirety.

In another embodiment, there is provided a method of detecting multiple sclerosis (MS) or pre-MS lesion in a subject comprising (a) administering to said subject a recombinant antibody or fragment as defined above, wherein the antibody or fragment carries a label; and (b) detecting the localization of said antibody in a neuronal tissue of said subject. The subject may be a human subject or a non-human mammalian subject.

In yet another embodiment, there is provided a method of preparing a multiple sclerosis (MS) model comprising (a) providing a non-human mammalian subject; and (b) administering to said subject one or more recombinant antibodies or fragments as defined above. The subject may be a mouse, hamster, rat or rabbit. The method may further comprise repeating step (b) at least once, and even repeating step (b) until an MS-like functional deficit is observed. Step (b) may be continued so long as said animal is alive.

In still yet another embodiment, there is provided a method of preparing a multiple sclerosis (MS) model comprising preparing a non-human mammalian subject that contains a transgenic B cell expressing a recombinant antibody or fragment thereof as defined above. The subject may be a mouse, hamster, rat or rabbit. Preparing may comprise administering a B cell expressing said antibody to said subject, wherein said B cell has been transformed with an expression construct that encodes said antibody under the control of a promoter active in said B cell, such as syngeneic B-cells. Alternatively, preparing may comprise generating a non-human mammalian subject that preparing comprises generating said non-human mammalian subject such that cells of said subject comprise a germ line insert of an exogenous expression construct that encodes said recombinant antibody or fragment thereof under the control of a promoter active in B cells of said subject.

A method of treating multiple sclerosis (MS) or clinically isolated syndrome in a patient comprising administering to said subject an agent or subjecting said subject to a therapy that reduces the amount or function of an antibody having a sequence as defined above. The agent may comprise an anti-idiotypic antibody to said antibody, an antigen fragment that binds to said antibody, an siRNA that reduces said antibody's expression, or a non-Fc containing antibody that competes with said antibody. The therapy may be B-cell ablation that reduces B-cells producing said antibody. The therapy may comprise physical removal of B-cells producing said antibody or physical removal of said antibody. The method may further comprise administering to said subject one or more traditional MS therapies. The agent maybe administered systemically or through a route that targets neuronal tissue.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DESCRIPTION OF ILLUSTRATIVE EMBODIMENTS

Figures 1A, 1B, 1C:
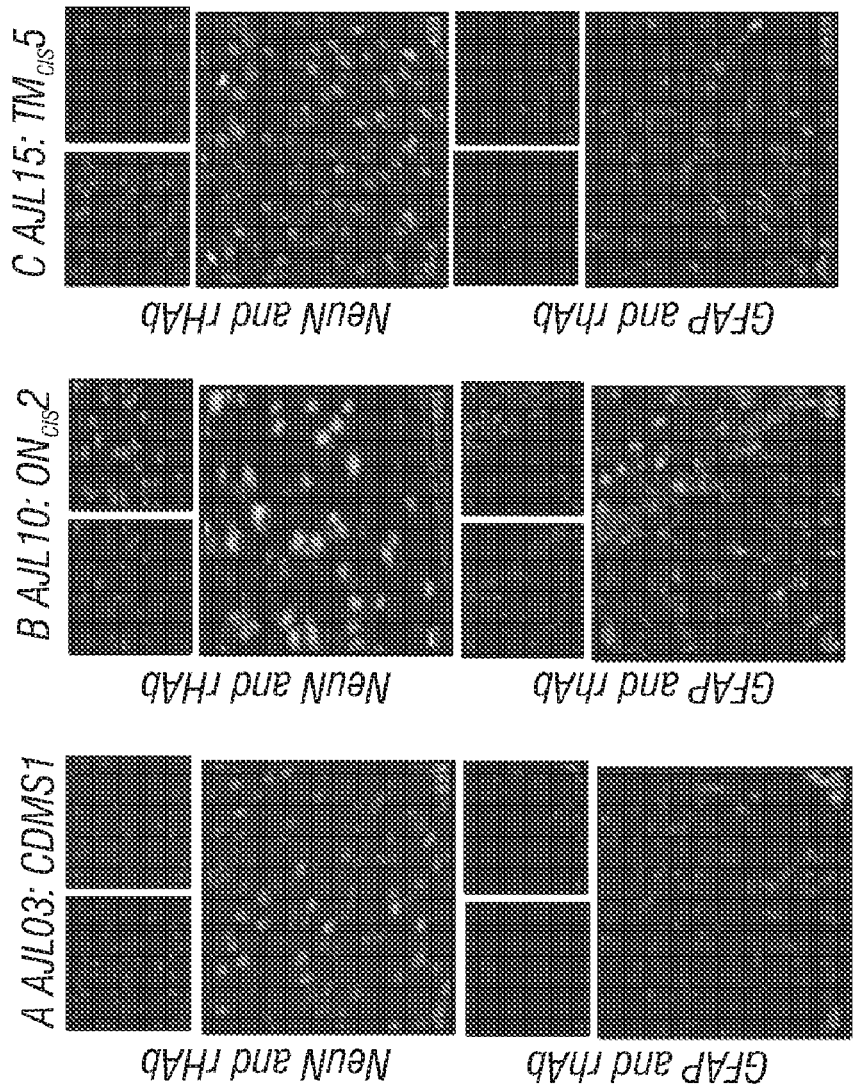
FIG. 1—ANTIBODY BINDING TO BRAIN TISSUE
Figures 1D, 1E, 1F:
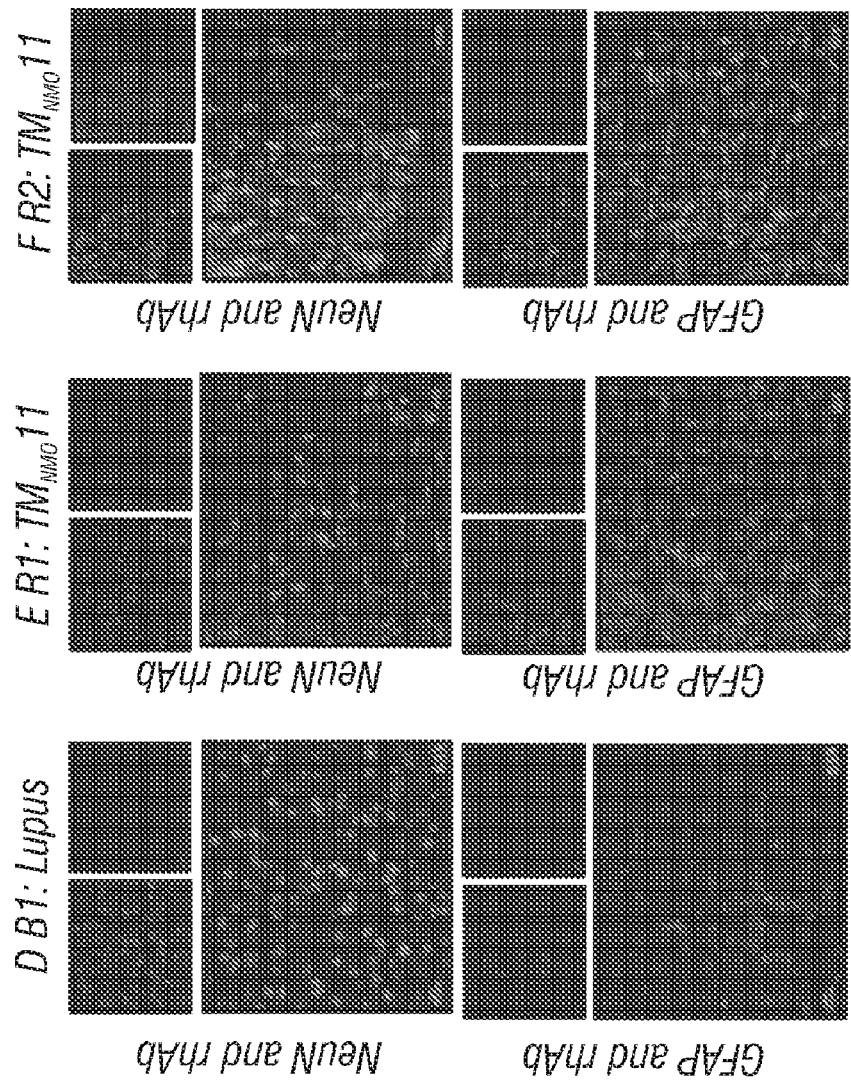
Figures 1J, 1K, 1L, 1M:
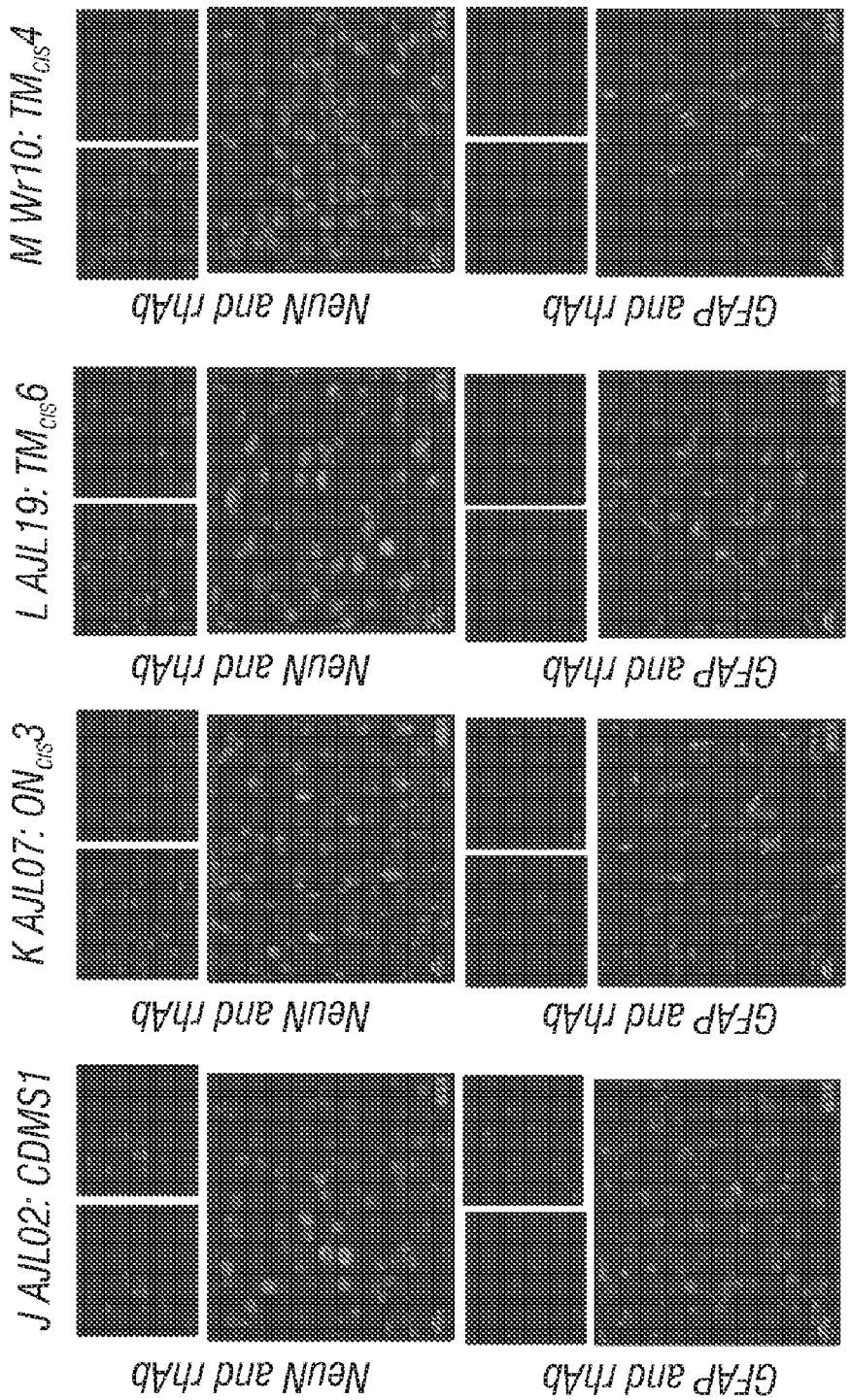
Figure 2:
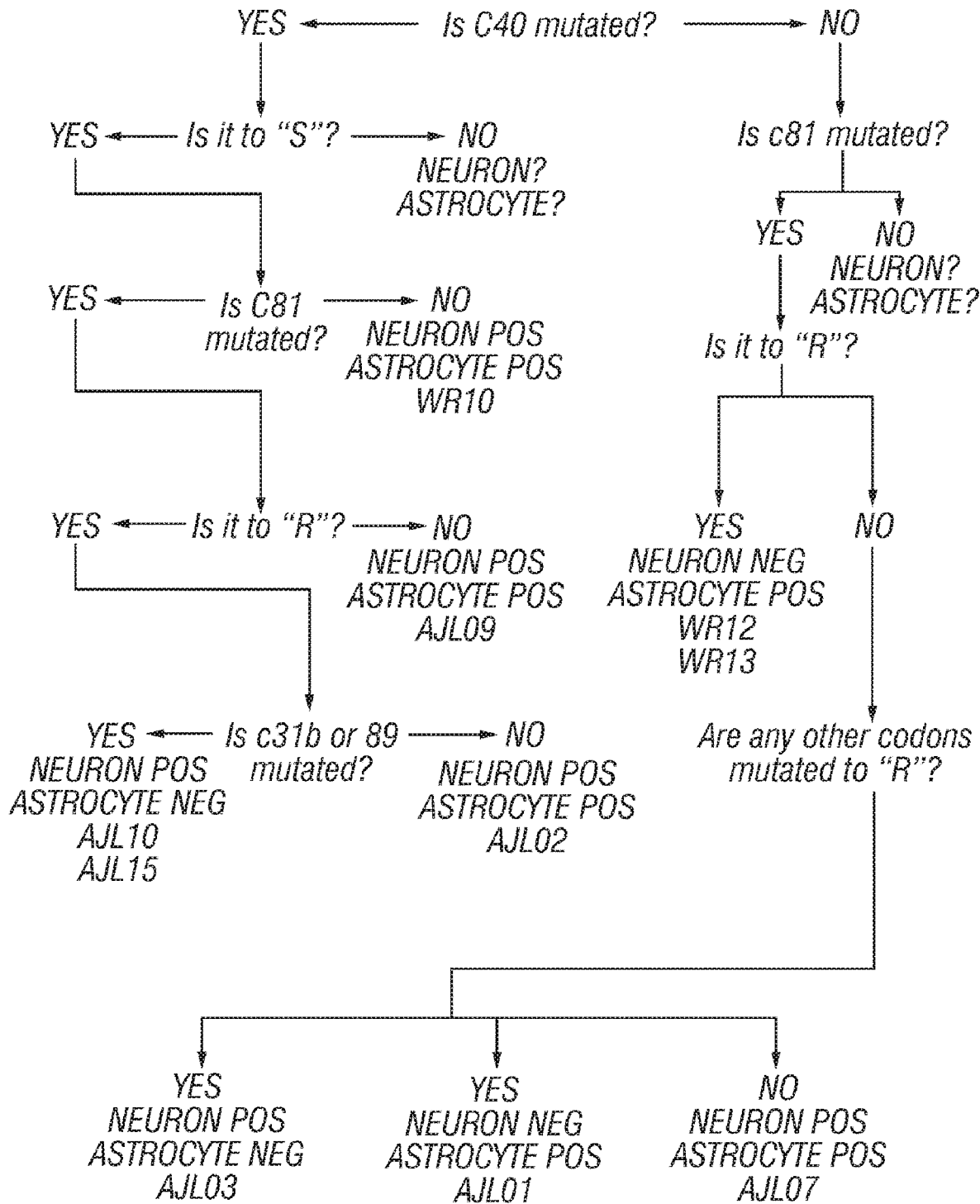
FIG. 2—CODON MUTATION DECISION TREE

As discussed above, the inventor's laboratory has discovered a biomarker for conversion from CIS to clinically definite MS (CDMS) in the antibody genetics of $V_H4$-utilizing B cells in the CSF, termed the antibody gene signature (AGS) (Cameron et al., 2009). She also found that B cells isolated from CNS lesions harbor the AGS (Ligocki et al., 2010). This shared pattern of somatic hypermutation at 6 codons along the $V_H4$ gene implicates that the B cell pools are recognizing a shared set of antigens in the MS disease state that are not recognized by B cells in healthy individuals. Thus, the inventor hypothesized that AGS-enriched antibodies may bind to targets within the CNS. To address this hypothesis, she generated a panel of 32 full-length recombinant human antibodies (rhAbs) from single CSF B cells whose antibody genes contained AGS-targeted mutations. Surveying B cells and antibodies within the CSF is relevant to CNS disease because there are shared B cell clones between the same MS patient's CSF and CNS (Obermeier et al., 2011), as well as between the meninges and CNS (Lovato et al., 2011). This panel of 32 rhAbs came from a diverse set of patients including CDMS and two initial CIS presentations (optic neuritis ($ON_{CIS}$) and transverse myelitis ($TM_{CIS}$)). $ON_{CIS}$ patients present with optic symptoms and lesions along the optic nerve, and $TM_{CIS}$ patients exhibit sensory symptoms with lesions along short segments of the spinal cord. Regardless of either presentation of CIS, both patient types have CSF B cells pools enriched for AGS and are at high risk of converting to CDMS.

These 32 rhAbs that contain somatic hypermutations at 2 or more the AGS codons were then demonstrated to bind to cellular targets in the gray matter of mice and human brain tissue. The cellular targets identified to date are neurons and astrocytes and are the subject of U.S. Pat. No. 8,394,583. Upon binning these rhAbs according to their reactivity towards neurons or astrocytes, the inventor discovered that certain mutations at particular codons were common in all rhAbs binding to neurons and that other mutations at particular codons were common in all rhAbs binding to astrocytes. Also, the absence of mutations at these codons were common in all rhAbs that did not bind either cell type. These data are summarized in Example 2.

These and other aspects of the disclosure are described in greater detail below.

I. MULTIPLE SCLEROSIS

A. Multiple Sclerosis

Multiple Sclerosis (MS) is one of the most common diseases of the central nervous system (brain and spinal cord). It is an inflammatory condition associated with demyelination, or loss of the myelin sheath. Myelin, a fatty material that insulates nerves, acts as insulator in allowing nerves to transmit impulses from one point to another. In MS, the loss of myelin is accompanied by a disruption in the ability of the nerves to conduct electrical impulses to and from the brain and this produces the various symptoms of MS, such as impairments in vision, muscle coordination, strength, sensation, speech and swallowing, bladder control, sexuality and cognitive function. The plaques or lesions where myelin is lost appear as hardened, scar-like areas. These scars appear at different times and in different areas of the brain and spinal cord, hence the term "multiple" sclerosis, literally meaning many scars.

Currently, there is no single laboratory test, symptom, or physical finding that provides a conclusive diagnosis of MS. To complicate matters, symptoms of MS can easily be confused with a wide variety of other diseases such as acute disseminated encephalomyelitis, Lyme disease, HIV-associated myelopathy, HTLV-I-associated myelopathy, neurosyphilis, progressive multifocal leukoencephalopathy, systemic lupus erythematosus, polyarteritis nodosa, Sjogren's syndrome, Behcet's disease, sarcoidosis, paraneoplastic syndromes, subacute combined degeneration of cord, subacute myelo-optic neuropathy, adrenomyeloneuropathy, spinocerebellar syndromes, hereditary spastic paraparesis/primary lateral sclerosis, strokes, tumors, arteriovenous malformations, arachnoid cysts, Arnold-Chiari malformations, and cervical spondylosis. Consequently, the diagnosis of MS must be made by a process that demonstrates findings that are consistent with MS, and also rules out other causes.

Generally, diagnosis of MS relies on two criteria. First, there must have been two attacks at least one month apart. An attack, also known as an exacerbation, flare, or relapse, is a sudden appearance of or worsening of an MS symptom or symptoms which lasts at least 24 hours. Second, there must be more than one area of damage to central nervous system myelin sheath. Damage to sheath must have occurred at more than one point in time and not have been caused by any other disease that can cause demyelination or similar neurologic symptoms. MRI (magnetic resonance imaging) currently is the preferred method of imaging the brain to detect the presence of plaques or scarring caused by MS.

The diagnosis of MS cannot be made, however, solely on the basis of MRI. Other diseases can cause comparable lesions in the brain that resemble those caused by MS. Furthermore, the appearance of brain lesions by MRI can be quite heterogeneous in different patients, even resembling brain or spinal cord tumors in some. In addition, a normal MRI scan does not rule out a diagnosis of MS, as a small number of patients with confirmed MS do not show any lesions in the brain on MRI. These individuals often have spinal cord lesions or lesions which cannot be detected by MRI. As a result, it is critical that a thorough clinical exam also include a patient history and functional testing. This should cover mental, emotional, and language functions, movement and coordination, vision, balance, and the functions of the five senses. Sex, birthplace, family history, and age of the person when symptoms first began are also important considerations. Other tests, including evoked potentials (electrical diagnostic studies that may reveal delays in central nervous system conduction times), cerebrospinal fluid (seeking the presence of clonally-expanded immunoglobulin genes, referred to as oligoclonal bands), and blood (to rule out other causes), may be required in certain cases.

B. Therapy and Prophylaxis

It may be that, on the basis of the diagnosis or prediction provided by the methods described herein, one will wish to begin, end or modify a therapeutic regimen. In particular, subjects diagnosed as having or at risk of developing MS may be started on a therapeutic regimen. The primary aims of therapy are returning function after an attack, preventing new attacks, and preventing disability. As with any medical treatment, medications used in the management of MS have several adverse effects, and many possible therapies are still under investigation.

During symptomatic attacks, administration of high doses of intravenous corticosteroids, such as methylprednisolone, is the routine therapy for acute relapses. The aim of this kind of treatment is to end the attack sooner and leave fewer lasting deficits in the patient. Although generally effective in the short term for relieving symptoms, corticosteroid treatments do not appear to have a significant impact on long-term recovery. Potential side effects include osteoporosis and impaired memory, the latter being reversible.

The earliest clinical presentation of relapsing-remitting MS (RRMS) is the clinically isolated syndrome (CIS). Several studies have shown that treatment with interferons during an initial attack can decrease the chance that a patient will develop MS. As of 2007, six disease-modifying treatments have been approved by regulatory agencies of different countries for relapsing-remitting MS. Three are interferons: two formulations of interferon beta-1a (trade names Avonex and Rebif) and one of interferon β-1b (U.S. trade name Betaseron®, in Europe and Japan Betaferon). A fourth medication is glatiramer acetate (Copaxone®). The fifth medication, mitoxantrone, is an immunosuppressant also used in cancer chemotherapy, is approved only in the USA and largely for SPMS. Finally, the sixth is natalizumab (marketed as Tysabri®). All six medications are modestly effective at decreasing the number of attacks and slowing progression to disability, although they differ in their efficacy rate and studies of their long-term effects are still lacking. Comparisons between immunomodulators (all but mitoxantrone) show that the most effective is natalizumab, both in terms of relapse rate reduction and halting disability progression; it has also been shown to reduce the severity of MS. Mitoxantrone may be the most effective of them all; however, it is generally considered not as a long-term therapy as its use is limited by severe cardiotoxicity.

The interferons and glatiramer acetate are delivered by frequent injections, varying from once-per-day for glatiramer acetate to once-per-week (but intra-muscular) for Avonex. Natalizumab and mitoxantrone are given by IV infusion at monthly intervals. Treatment of progressive MS is more difficult than relapsing-remitting MS. Mitoxantrone has shown positive effects in patients with secondary progressive and progressive relapsing courses. It is moderately effective in reducing the progression of the disease and the frequency of relapses in patients in short-term follow-up. On the other hand no treatment has been proven to modify the course of primary progressive MS.

Disease-modifying treatments only reduce the progression rate of the disease but do not stop it. As multiple sclerosis progresses, the symptomatology tends to increase. The disease is associated with a variety of symptoms and functional deficits that result in a range of progressive impairments and handicap. Management of these deficits is therefore very important. Both drug therapy and neurorehabilitation have shown to ease the burden of some symptoms, even though neither influence disease progression. As for any patient with neurologic deficits, a multidisciplinary approach is key to limiting and overcoming disability; however there are particular difficulties in specifying a 'core team' because people with MS may need help from almost any health profession or service at some point. Similarly for each symptom there are different treatment options. Treatments should therefore be individualized depending both on the patient and the physician.

II. PRODUCING AND USE OF MONOCLONAL ANTIBODIES

A. General Methods

Antibodies according to the present disclosure may be produced by standard methods as are well known in the art (see, e.g., Antibodies: A Laboratory Manual, Cold Spring Harbor Laboratory, 1988; U.S. Pat. No. 4,196,265). In brief, somatic cells with the potential for producing antibodies, specifically B lymphocytes (B cells), are selected. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

The normal immune system has the ability to generate millions of antibodies with different antigen binding abilities. The diversity is brought about by the complexities of constructing immunoglobulin molecules. These molecules consist of paired polypeptide chains (heavy and light) each containing a constant and a variable region. The structures of the variable regions of the heavy and light chains are specified by immunoglobulin V genes. The heavy chain variable region is derived from three gene segments known as VH, D and JH. In humans there are about 100 different VH segments, over 20 D segments and six JH segments. The light chain genes have only two segments, the VL and JL segments. Antibody diversity is the result of random combinations of VH/D/JH segments with VUJL components superimposed on which are several mechanisms including junctional diversity and somatic mutation.

The germline VH genes can be separated into at least six families (VH1 through VH6) based on DNA nucleotide sequence identity of the first 95 to 101 amino acids. Members of the same family typically have 80% or more sequence identity, whereas members of different families have less than 70% identity. These families range in size from one VH6 gene to an estimated greater than 45 VH3 genes. In addition, many pseudogenes exist. Recent studies have nearly completed a physical map of the VH locus on chromosome 14q32.13.15. It has now been estimated that the human VH repertoire is represented by approximately 50 functional VH segments with about an equal number of pseudogenes. These studies estimate the size of the VH locus to be approximately 1100 kb. The VH4 family of genes contains 9 different members: 4-04, 4-28, 4-30, 4-31, 4-34, 4-39, 4-59, 4-61, 4-B4.

The present disclosure relates in part to antibodies exhibiting a "signature" in the VH4 sequences of certain B cells. The sequence signature typically comprises residues 40 and/or 81, but also can include one or more of residues 31B, 32, 57, 60 and 89. In particular, residue 40 (serine) and 81 (asparagine or other) substitutions as compared to germline, and the lack of changes at residues 31B, 32, 57, 60 and 89, as compared to germline, indicate antibodies capable of binding to brain. By examining the sequence at these positions, and identifying mutations at one or more of the positions, it can be determined that a subject is at risk of developing MS and, in the presence of additional factors, has MS. In the present disclosure, the sequence at these positions can also determine whether a particular antibody will bind to the brain, and even what type of cell the antibody will bind. It is also possible these antibodies bind to yet undiscovered cell types in the human body In certain embodiments, the antibodies of the disclosure or binding fragments thereof do not specifically bind to myelin antigens (e.g., myelin basic protein (MBP), myelin oligodendrocyte glycoprotein (MOG)). For example, the antibodies of the disclosure or binding fragments thereof bind to a myelin antigen (MBP and/or MOG) with a $K_D$ greater than $10^{-5}$M or greater than $10^{-4}$M.

Furthermore, the antibodies sequences may vary from the sequences provided above, optionally using methods discussed in greater detail below. For example, amino sequences may vary from those set out above in that (a) the variable regions may be segregated away from the constant domains of the light chains, (b) the amino acids may vary from those set out above while not drastically affecting the chemical properties of the residues thereby (so-called conservative substitutions), (c) the amino acids may vary from those set out above by a given percentage, e.g., 80%, 85%, 90%, 91%, 92%, 93%, 94%, 95%, 96%, 97%, 98% or 99% homology. Alternatively, the nucleic acids encoding the antibodies may (a) be segregated away from the constant domains of the light chains, (b) vary from those set out above while not changing the residues coded thereby, (c) may vary from those set out above by a given percentage, e.g., 70%, 75%, 80%, 85%, 90%, 91%, 92%, 93%, 94%, 95%, 96%, 97%, 98% or 99% homology, or (d) vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C.

In making conservative changes in amino acid sequence, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

C. Engineering of Antibody Sequences

In various embodiments, one may choose to engineer sequences of the identified antibodies for a variety of reasons, such as improved expression, improved cross-reactivity, diminished off-target binding or abrogation of one or more natural effector functions, such as activation of complement or recruitment of immune cells (e.g., T cells). In particular, IgM antibodies may be converted to IgG antibodies. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns Recombinant full length IgG antibodies can be generated by subcloning heavy and light chain Fv DNAs from the cloning vector into a Lonza pConIgG1 or pConK2 plasmid vector, transfected into 293 Freestyle cells or Lonza CHO cells, and collected and purified from the CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, humanized or CDR-grafted antibody). In yet a further embodiment, the antibody is a fully human recombinant antibody.

The present disclosure also contemplates isotype modification. By modifying the Fc region to have a different isotype, different functionalities can be achieved. For example, changing to $IgG_4$ can reduce immune effector functions associated with other isotypes.

Modified antibodies may be made by any technique known to those of skill in the art, including expression through standard molecular biological techniques, or the chemical synthesis of polypeptides. Methods for recombinant expression are addressed elsewhere in this document.

D. Expression

Nucleic acids according to the present disclosure will encode antibodies, optionally linked to other protein-encoding sequences. As used in this application, the term "a nucleic acid encoding an antibody" refers to a nucleic acid molecule that has been isolated free of total cellular nucleic acid.

TABLE 1

| Amino acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAU |

The DNA segments of the present disclosure include those encoding biologically functional equivalent proteins and peptides of the sequences described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

Within certain embodiments, expression vectors are employed in order to produce the polypeptide. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment.

A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present disclosure, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988: Horlick et al., 1989; Johnson et al. 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988: Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), DIA dopamine receptor gene (Lee et al., 1997), insulin-like growth factor II (Wu et al., 1997), human platelet endothelial cell adhesion molecule-1 (Almendro et al., 1996).

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

2. IRES

In certain embodiments of the disclosure, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multi-Purpose Cloning Sites

Vectors can include a multiple cloning site (MCS), which is a nucleic acid region that contains multiple restriction enzyme sites, any of which can be used in conjunction with standard recombinant technology to digest the vector. See Carbonelli et al. (1999); Levenson et al. (1998); and Cocea (1997), incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference).

5. Termination Signals

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the disclosure, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670, 488). The various viral vectors described below, present specific advantages and disadvantages, depending on the particular gene-therapeutic application.

Adenoviral Vectors. In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present disclosure comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a iv sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenoviral encapsidation. The intermediate region encodes components of the adenoviral capsid. Adenoviral inverted terminal repeats (ITRs; 100-200 bp in length), are cis elements, and function as origins of replication and are necessary for viral DNA replication. The iv sequence is required for the packaging of the adenoviral genome.

A common approach for generating adenoviruses for use as a gene transfer vectors is the deletion of the E1 gene (E1−), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1−, replication-deficient virus is then proliferated in a "helper" cell line that provides the E1 polypeptides in trans (e.g., the human embryonic kidney cell line 293). Thus, in the present disclosure it may be convenient to introduce the transforming construct at the position from which the E1-coding sequences have been removed. However, the position of insertion of the construct within the adenovirus sequences is not critical to the disclosure. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1996) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the disclosure. The adenovirus may be of any of the 42 different known serotypes and/or subgroups A-F. Adenovirus type 5 of subgroup C is the preferred starting material in order to obtain the conditional replication-defective adenovirus vector for use in the present disclosure. This is because adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Adenovirus growth and manipulation is known to those of skill in the art, and exhibits broad host range in vitro and in vivo (U.S. Pat. Nos. 5,670,488; 5,932,210; 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors. In certain embodiments of the disclosure, the uses of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present disclosure may be genetically modified in such a way that some of the structural, infectious genes of the native virus have been removed and replaced instead with a nucleic acid sequence to be delivered to a target cell (U.S. Pat. Nos. 5,858,744; 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present disclosure are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. Nos. 5,955,331; 5,888,502, each specifically incorporated herein by reference). Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present disclosure (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery include a requirement for ongoing cell division for stable infection and a coding capacity that prevents the delivery of large genes. However, recent development of vectors such as lentivirus (e.g., HIV), simian immunodeficiency virus (SIV) and equine infectious-anemia virus (EIAV), which can infect certain non-dividing cells, potentially allow the in vivo use of retroviral vectors for gene therapy applications (Amado and Chen, 1999; Klimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado and Chen, 1999; Engel and Kohn, 1999), cancer (Clay et al., 1999), cerebrovascular disease (Weihl et al., 1999) and hemophilia (Kay, 1998).

Herpesviral Vectors. Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Garrido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or α genes, Early (E) or β genes and Late (L) or γ genes Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. Nos. 5,879,934; 5,851,826, each specifically incorporated herein by reference in its entirety).

One IE protein, ICP4, also known as α4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP4? (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors. Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins is expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTRs serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-loc gene in this disclosure, into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present disclosure, one may graft or transplant cells infected with the recombinant lentivirus ex vivo, or infect cells in vivo.

Other Viral Vectors. The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present disclosure and may be selected according to the requisite properties of the target system.

In certain embodiments, vaccinia viral vectors are contemplated for use in the present disclosure. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., $P_{450}$ (U.S. Pat. No. 5,506,138). The preparation, growth and manipulation of vaccinia viruses are described in U.S. Pat. Nos. 5,849,304 and 5,506,138 (each specifically incorporated herein by reference).

In other embodiments, sindbis viral vectors are contemplated for use in gene delivery. Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of Sindbis virus suggest that it would be a useful vector for the expression of heterologous genes. First, it has a wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors. Chimeric or hybrid viral vectors are being developed for use in therapeutic gene delivery and are contemplated for use in the present disclosure. Chimeric poxviral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

10. Non-Viral Transformation

Suitable methods for nucleic acid delivery for transformation of an organelle, a cell, a tissue or an organism for use with the current disclosure are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection. In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present disclosure include the introduction of a nucleic acid by direct microinjection. Direct microinjection has been used to introduce nucleic acid constructs into *Xenopus* oocytes (Harland and Weintraub, 1985).

Electroporation. In certain embodiments of the present disclosure, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human K-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner Examples of some species which have been transformed by electroporation of intact cells include maize (U.S. Pat. No. 5,384,253; Rhodes et al., 1995; D' Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 92/17598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Calcium Phosphate. In other embodiments of the present disclosure, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading. Additional embodiments of the present disclosure include the introduction of a nucleic acid by direct sonic loading. LTK⁻ fibroblasts have been transfected with the thymidine kinase gene by sonication loading (Fechheimer et al., 1987).

Liposome-Mediated Transfection. In a further embodiment of the disclosure, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the disclosure, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor-Mediated Transfection. Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present disclosure.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present disclosure, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present disclosure can be specifically delivered into a target cell in a similar manner 11. Expression Systems Numerous expression systems exist that comprise at least a part or all of the compositions discussed above. Prokaryote- and/or eukaryote-based systems can be employed for use with the present disclosure to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MaxBac® 2.0 from Invitrogen® and BacPack™ Baculovirus Expression System From Clontech®.

Other examples of expression systems include Stratagene 's Complete Control' Inducible Mammalian Expression System, which involves a synthetic ecdysone-inducible receptor, or its pET Expression System, an *E. coli* expression system. Another example of an inducible expression system is available from Invitrogen®, which carries the T-Rex™ (tetracycline-regulated expression) System, an inducible mammalian expression system that uses the full-length CMV promoter. Invitrogen® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

12. Preparation of Transgenic Animals

In an embodiment of the disclosure, a transgenic animal is produced by the integration of an antibody transgene into the genome in a manner that permits the expression of the transgene. Methods for producing transgenic animals are generally described by Wagner and Hoppe (U.S. Pat. No. 4,873,191; incorporated herein by reference), and Brinster et al. (1985; incorporated herein by reference).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of DNA for microinjection are described in in Palmiter et al. (1982); and in Sambrook et al. (2001).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by C02 asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/mi). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

13. Interfereing RNAs

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, *C. elegans*, Trypanasoma, *Drosophila*, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

The making of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen et al., 2000; Elbashir et al., 2001).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

F. Single Chain/Single Domain Antibodies

A Single Chain Variable Fragment (scFv) is a fusion of the variable regions of the heavy and light chains of immunoglobulins, linked together with a short (usually serine, glycine) linker. This chimeric molecule, also known as a single domain antibody, retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single domain or single chain variable fragments lack the constant Fc region found in complete antibody molecules, and thus, the common binding sites (e.g., protein A/G) used to purify antibodies (single chain antibodies include the Fc region). These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

III. PHARMACEUTICAL FORMULATIONS AND TREATMENT OF MS

A. Central Nervous System Therapies

In accordance with the present disclosure, the inventor proposes that the inhibition of antibodies described herein, i.e., those having the VH4 signature and binding to gray matter antigens, can be inhibited as part of a CNS disease therapy, such as Multiple Sclerosis. There are several different embodiments by which this can be achieved.

First, one may ablate the B cells populations that produce the antibodies described herein. The most well known example of a B cell ablative therapy is the use of an anti-CD20 antibody that non-selectively attacks B cells. This type of approach has been used to treat B cell malignancies and certain autoimmune disorders. Another option would be to tailore a specific agent that could physically ablate only the specific B cells described herein, such as an anti-idiotypic antibody, or one that could "silence" the expression of the antibodies, such as an siRNA directed to the specific message produced by these B cells.

Another approach would be to limit the activity of the antibodies described herein by providing an inhibitory factor. A factor with this capability could be an anti-idiotypic antibody that binds the AGS antibody, a peptide that reflects an epitope to which the AGS antibody binds, or an antibody fragment having the same specificity as the AGS antibody but lacking effector functions (i.e., lacking Fc structures).

B. Formulation and Administration

The present disclosure provides pharmaceutical compositions comprising antibody inhibitory substances. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Other suitable pharmaceutical excipients include starch, glucose, lactose, sucrose, saline, dextrose, gelatin, malt, rice, flour, chalk, silica gel, sodium stearate, glycerol monostearate, talc, sodium chloride, dried skim milk, glycerol, propylene glycol, water, ethanol and the like.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The antibodies of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

C. Combination Therapies

In the context of the present disclosure, it also is contemplated that agents described herein could be used similarly in conjunction with more traditional MS treatments. These compositions or therapies would be provided in a combined amount effective to treat the disease. This process may involve administration of the agent according to the present disclosure and the other agent or therapy at the same time. This may be achieved by administering a single composition or pharmacological formulation that includes both agents, or by contacting the cell with two distinct compositions or formulations, at the same time, wherein one composition includes the agent according to the present disclosure and the other includes the other agent.

Alternatively, the therapy according to the present disclosure may precede or follow the other agent/treatment by intervals ranging from minutes to weeks. In embodiments where the other agent is administered separately, one would generally ensure that a significant period of time did not expire between the time of each delivery, such that the agents would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either agent/therapy will be desired. Various combinations may be employed, where an agent according to the present disclosure therapy is "A" and the other agent/therapy is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Traditional therapeutic MS agents or factors suitable for combination are those described above in the discussion of MS therapy and prophylaxis.

IV. ANTIBODY CONJUGATES

Antibodies may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., immunosuppression/anti-inflammation. Non-limiting examples of such molecules are set out above. Such molecules are optionally attached via cleavable linkers designed to allow the molecules to be released at or near the target site.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging" Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{99}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups are often used to bind radioisotopes to antibody and exist as metallic ions are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and is described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, there are immunodetection methods using the antibodies of the present disclosure. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of antibodies also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to any antigen present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

B. Immunodetection Kits

In still further embodiments, there are kits for use with the immunodetection methods described above. The immunodetection kits will thus comprise, in suitable container means, a first antibody and, optionally, an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with embodiments discussed herein.

The kits may further comprise a suitably aliquoted composition of the antibody, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody and any other reagent containers in close confinement for commercial sale. Such containers may include injection or blow-molded plastic containers into which the desired vials are retained.

VI. EXAMPLES

The following examples are included to demonstrate preferred embodiments. It should be appreciated by those of skill in the art that the techniques disclosed in the examples which follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods

Patient sample acquisition and processing. CSF was obtained by lumbar puncture from patients recruited into the study in accordance with The University of Texas Southwestern Medical Center (UTSWMC) Institutional Review Board (IRB). This study includes patient samples as previously published by the inventor's group (Cameron et al., 2009 and Ligocki et al., 2013 and Ligocki et al., 2015) containing patients with clinically definite multiple sclerosis (CDMS), clinically isolated syndrome optic neuritis ($ON_{CIS}$), and clinically isolated syndrome transverse myelitis ($TM_{CIS}$). The samples were stained with fluorescently labeled antibodies and sorted for single $CD19^+$ B cells through a $CD45^+$ lymphocyte gate as previously described into 96-well plates using either the BD FACSAria flowcytometer (Becton Dickinson, San Jose, Calif.) or the MoFlo High-Performance Cell Sorter (Cytomation, Ft Collins, Colo.) (Ligocki et al., 2013).

Single-cell PCR and genetic analysis of $V_H$ and $V_K$ genes. After the single cell sort and cell lysis, either gDNA was amplified for the CDMS patient samples or cDNA was generated for the $ON_{CIS}$ and $TM_{CIS}$ patient samples as previously described (Ligocki et al., 2013). Multi-plexed nested PCR was performed to amplify and the Immunoglobulin (Ig) heavy chain and corresponding Ig kappa light chain from each individually sorted CSF B cell. The products were purified, sequenced, catalogued, and analyzed for gene and mutation characteristics (Ligocki et al., 2013).

Germline rearrangements were identified using the IMGT/V-QUEST Ig blasting tool (world-wide-web at imgt.org/IMGT_vquest/share/textes/). Antibody variable heavy ($V_H$) and variable kappa (Vκ) sequences were analyzed and compiled using a Perl program developed at UTSWMC (Ligocki et al., 2010 and Ligocki et al., 2013) using IMGT/V-QUEST as the initial source for sequence alignment.

Cloning of full-length recombinant human IgG antibodies (rhAbs). Sequences from CDMS, $ON_{CIS}$, and $TM_{CIS}$ patients were chosen as candidates for cloning into full-length expression vectors based on their $V_H$ genetics. The criteria was: expressing a $V_H4$ gene and have 2 or more of the 6 AGS codons mutated (Cameron et al., 2009 and Ligocki et al., 2010). 60% were also clonally expanded by identifying another $V_H$ sequence within the same patient with identical amino acids in the CDR3 region. The corresponding Vic sequence was amplified from the same well as the $V_H$ sequence to identify the antibody binding region of the single CSF B cell. Sequence and patient details for each selection are shown in Table 5 and Supplemental Table 6. Additional rounds of PCR were done to add restriction enzyme sites to both the 5' and 3' ends of the original PCR products to allow for insertion into the expression vectors using modifications of previously published primers (Yurasov et al., 2005). Some heavy and light chain rearrangement sequences were purchased from Integrated DNA Technologies (IDT, IA, USA) for extraction into the expression vectors. Dr. Michel Nussenzweig provided the backbone expression vectors for both the IgG and IgK chains. These vectors and the procedure have been extensively described for the production of monoclonal human $IgG_1$ (Tiller et al., 2008). Briefly, AgeI was used as the 5' restriction enzyme site for both the $V_H$ and Vκ inserts and plasmid backbone and SalI and BsiWI were used as the 3' restriction enzyme site for the $V_H$ and Vκ respectively (NEB, MA, USA). After digestion, ligation of both the insert and the corresponding expression vector backbone was performed using T4 ligase (NEB). DH5c cells were transformed with a plasmid and individual colonies from the plate were grown for miniprep (Qiagen, CA, USA). The vectors were sequenced in order to confirm that the insert matched the original patient heavy and light chain rearrangements captured by PCR and that the coding region remained in frame. Midiprep DNA (Qiagen) was used for transformation and production of rhAbs in culture. Sequences were validated after each growth.

Two control rhAbs were provided that were cloned from systemic lupus erythematosus (SLE) patient derived B cells. B1 has been shown to not bind to mouse brain and G11 has been shown to bind to NMDARs in the mouse brain as well as dsDNA (Zhang et al., 2009). These two antibodies have been studied and published and were used as controls for the full-length $IgG_1$ rhAb construct in all the experiments presented in this current study.

Production of monoclonal rhAbs. Human embryonic kidney fibroblast (HEK) 293T cells were grown to 50-80% confluency in a 10 cm dish in DMEM media supplemented with FCS (Gibco, Life Technologies). The cotransfection of paired cloning vectors corresponding to the IgK and the IgH of a rhAb were mixed (12.5 μg total DNA) with JetPEI solution (Polyplus transfection) and added dropwise to the cells. The plates were incubated in a 5% $CO_2$ water-jacketed incubator (Nuaire, MN, USA) at 37° C. in 20 ml DMEM media supplemented with ultra-low IgG FCS media (Gibco). Supernatant was harvested and fresh media added on days 3, 5, 7, and 10. ELISAs were used to determine the yield and the concentration of the rhAbs produced in culture. Goat anti-human IgG Fc antibody (Santa Cruz. Tex., USA) was used as the coating antibody and serially diluted samples were incubated for 2 hrs at room temperature. Plates were probed with goat anti-human IgG Fc HRP-conjugated antibody (Santa Cruz) for 1 hr and developed using tetramethylbenzidine (TMB) substrate solution (Ebioscience, CA, USA) and stopped with 1 M HCl. The plates were read at 450 nm using the Epoch Nano (Biotek, VT, USA). Standard curves and rhAb concentrations were interpolated using GraphPad Prism 6 (CA, USA). Supernatants were concentrated using the 10 kDa MWCO Amcion Ultra centrifugal filter units (Millipore, Mass., USA) following manufacturer's recommendations. A second ELISA was performed on the concentrated stocks of rhAbs and then aliquoted and stored at −80° C. Additionally, a non-transfected cell culture supernatant was confirmed to not contain any IgG above ELISA detection. These concentrated rhAbs were used as primary antibodies for all mouse brain immunohistochemistry.

Biotinylation of monoclonal rhAbs. A set of ten AGS rhAbs and 2 control rhAbs were purified by passing supernatant through a column with a bed of protein G sepharose beads followed by dialysis in PBS and DPBS (Life Technologies). Purity and yield were determined by SDS-page gel stained with coomasie blue and ELISA as described above. Each rhAb was biotinylated using 100 μg of column-purified product and following manufacturer's instructions for the Thermo Scientific EZ-Link Micro NHS-PEG4-Biotinylation kit (Thermo Scientific, MA, USA). These biotinylated rhAbs were used as primary antibodies for all human brain immunohistochemistry.

Processing of frozen brain tissue. Mice were sacrificed 2-3 days post stroke induction as previously described (Stowe et al., 2011) and perfused with 4% paraformaldehyde. The brains were extracted and preserved in 4% paraformaldehyde for 48 hrs at 4° C. followed by cryoprotection in sequential 15% and 30% sucrose solutions. Postmortem human brain samples were provided by the Human Brain and Spinal Fluid Resource Center (UCLA, Los Angeles, Calif.). Three samples were used for the studies: white matter (WM) from a healthy control without neurological complications (HC), white matter plaque from a patient with clinically definite MS (MS-P), normal appearing WM from the same MS patient (MS-WM), and normal appearing gray matter (MS-GM). Mean time to sampling from time of death was 16 hrs. Upon removing from −80° C., they were preserved similarly to mouse brains with 4% paraformaldehyde for 48 hrs at 4° C. followed by cryoprotection in sequential 15% and 30% sucrose solutions. All tissues were embedded in O.C.T freezing compound and stored at −20° C. until cryosectioned. Tissue sections (12-16 μm) were cut and attached to charged glass slides using a cryostat (Thermo Scientific MICROM) and frozen at −20° C. Tissues were stained with cresyl violet to validate the integrity of the preservation of the tissue.

Diaminobenzidine (DAB)-immunohistochemistry (IHC) staining of mouse tissue. Tissue sections were subjected to antigen retrieval for 2 min using low pH Antigen Unmasking Solution (Vector Laboratories, Burlingame, Calif., USA). Endogenous biotin was blocked using 3% $H_2O_2$ solution for 5 min at room temperature and then washed. The sections were blocked with 3% normal goat serum in PBS for 10 min at room temperature, washed with PBS, and then were incubated overnight at 4° C. with 1 μg rhAb (10 ng/μl) per brain slice. The next day, sections were washed and DAB staining was conducted following the manufacturer's instructions using a biotinylated secondary goat anti-human IgG Fc antibody (Vector Laboratories, Burlingame, Calif., USA). The slides were dehydrated and cleared with sequential washes in increasing percentages of EtOH, from 70% to 100%, with two final washes in xylenes. Slides were mounted with a permount:xylene solution and imaged using a 40× brightfield lens on the NanoZoomer (Hammatsu, Japan). Images were visualized using NDP.view software (Hammatsu, Japan) and 20× images were exported for visualization and adjustments to brightness and contrast were done with ImageJ software (NIH, USA).

DAB-IHC staining of human tissue. Initial processing of the human brain tissue sections remained the same as the mouse tissue. After blocking with 3% normal goat serum in PBS for 10 min at room temperature, an additional blocking step was performed with BloxAll for 10 min at room temperature (Vector Laboratories, Burlingame, Calif., USA). Tissues were incubated overnight at 4° C. with 1 μg biotinylated-rhAb (10 ng/μl) per brain slice. The next day, these biotinylated-rhAbs were detected without a secondary antibody and instead with ABC reagent alone (Vector Laboratories, Burlingame, Calif., USA). Dehydration, clearing, mounting, and visualization of the human tissue followed the same procedure as the mouse tissue.

Immunofluorescence (IFC) staining of mouse tissue. Ten AGS rhAbs and 2 control rhAbs from the DAB panel were selected for further experiments using IFC (Table 5). Tissue sections were subjected to antigen retrieval for 2 min using low pH Antigen Unmasking Solution (Vector Laboratories, Burlingame, Calif., USA). The sections were blocked with 1% normal goat serum and 1% Tween-20 in PBS for 1 hr at room temperature. Due to the presence of IgG deposits even in healthy brain and as an artifact of post-mortem tissue preparation, the set of 10 rhAbs and the 2 control rhAbs used in the mouse brain IFC were biotinylated to eliminate the need for a species specific secondary antibody. Most of the rhAbs were diluted in blocking solution. Pierce Immunostain Enhancer (Thermo Scientific) was used as the diluent for the primary rhAb incubation as well as the secondary Alexa Fluor488 for the following two rhAbs: AJL03, AJL15. Slides were washed with PBS, and then incubated overnight at 4° C. with 1 μg rhAb (10 ng/μl) per brain slice. Next day, the sections were washed and incubated for 1 hr at room temperature with the secondary antibody Alexa Fluor 488 goat anti-human IgG Fc (Life Technologies). Then a colocalization marker, either GFAP (Abcam) or NeuN (Chemicon) were used at 1:1000 and 1:100 dilutions respectively, was incubated for 1 hr at room temperature and then incubated for an additional hour with the appropriate secondary antibody Alexa Fluor 594 anti-rabbit IgG Fc for GFAP or Alexa Fluor 594 anti-mouse IgG Fc for NeuN detection (Life Technologies). Next, the stained tissue sections were incubated for three minutes with DAPI (1:1000) as a counterstain for nuclei (Life Technologies). The sections were washed and wet mounted with Fluoro-Gel (Electron Microscopy Diatome). Slides were viewed with a fluorescent Leica TCS SP5 confocal microscope (Leica microsystems) and viewed and adjusted in brightness and contrast using ImageJ software (NIH, USA).

IFC staining of human tissue. Initial processing of the human brain tissue sections remained the same as the mouse tissue above. After the initial blocking, endogenous biotin was blocked per manufacturer's instructions using the streptavidin-biotin blocking kit (Vector Laboratories, Burlingame, Calif., USA). Pierce Immunostain Enhancer (Thermo Scientific) was used as the diluent for the primary rhAb incubation as well as the secondary Alexa Fluor 488 for all human tissue IFC. Slides were washed with PBS, and then incubated overnight at 4° C. with 2 μg rhAb (20 ng/μl) per brain slice. Next day, the sections were washed, and incubated for 1.5 hrs at room temperature with the secondary antibody Alexa Fluor 488 goat anti-streptavidin (Life Technologies). The colocalization with either GFAP or NeuN, DAPI counterstain, mounting and visualization followed the same procedure as the mouse brain tissue.

Example 2—Results

Of the 32 rhAbs that were evaluated for binding to brain tissue, 30 bound to brain tissue by DAB staining. Of those, 10 were evaluated for binding to neurons and astrocytes by IFC. Of those 10, 4 bound to both neurons and astrocytes, 3 bound to neurons only and 3 bound to astrocytes only. Further investigation of the 6 AGS codons revealed that all brain binding antibodies must have replacement mutations in at least two of the AGS codons. One of these mutations is typically an "R" or "N" replacement result at codon 81. Antibodies that do not have a mutation at codons 31b, 40, or 89 but have a "T" or "R" replacement result at codon 56 bind astrocytes, but not neurons. Antibodies that do not meet the astrocyte binding criteria bind neurons, and also have an "S" replacement result at codon 40. Those antibodies that bind neurons and astrocytes do not have a mutation at codon 31b and no "R" replacement result at codon 56. This finding could have profound implications in the diagnostic and therapeutic treatment of CNS disease, such as Multiple Sclerosis.

Example 3—Discussion

It has been well-established in the literature that somatic hypermutations in the variable antibody gene regions enable antibodies to bind their cognate antigen with greater affinity. In fact, some studies have demonstrated that loss of particular mutations at certain codons in a single antibody gene can abrogate binding of the particular antibody to its cognate antigen. In the case of these AGS-enriched antibodies, we describe, for the first time, a commonality of somatic hypermutation to particular replacement amino acids among a panel of antibodies expressed by individual B cells with distinct CDR3 regions that bind neurons, astrocytes, both neurons and astrocytes or neither cell type. Thus, by following the Decision Tree based on the amino acid resulting from somatic hypermutation at particular codons, one can predict whether the antibody will bind neurons, astrocytes, both neurons and astrocytes or neither cell type (FIG. 2).

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

TABLE 1

Heavy Chain Sequences of AGS Enriched CSF Antibodies

| | 4-30 Codon | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| | 4-30 Kabat | | | | | | | | | | | | | | | | | |
| | | 1 | 2 | 3 | 4 | 5 | 6 | 7 | 8 | 9 | 10 | 11 | 12 | 13 | 14 | 15 | 16 | 17 |
| Region | FR1 | | | | | | | | | | | | | | | | | |
| Germ. AA | Q | V | Q | L | Q | E | S | G | P | | G | L | V | K | P | S | Q | T |
| Germ. Nuc | cag | gtg | cag | ctg | cag | gag | tcg | ggc | cca | | gga | ctg | gtg | aag | cct | tca | cag | acc |
| WR12 AA | Q | V | Q | L | Q | E | S | G | P | | G | L | V | K | P | S | Q | T |
| WR12 Nuc | cag | gtg | cag | ctg | cag | gag | tcg | ggc | cca | | gga | ctg | gtg | aag | cct | tca | cag | acc |

TABLE 1-continued Heavy Chain Sequences of AGS Enriched CSF Antibodies

| | | | | | | | | | | | | | | | | | | |
|---|---|---|---|---|---|---|---|---|---|---|---|---|---|---|---|---|---|---|
| WR13 AA | Q | V | Q | L | Q | E | S | G | P | | G | L | V | K | P | S | Q | T |
| WR13 Nuc | cag | gtg | cag | ctg | cag | gag | tcg | ggc | cca | | gga | ctg | gtg | aag | cct | tca | cag | acc |

| | | | | | | | | | | | | | | | | | | |
|---|---|---|---|---|---|---|---|---|---|---|---|---|---|---|---|---|---|---|
| | | | | | | | | 4-30 Codon | | | | | | | | | | |
| | 19 | 20 | 21 | 22 | 23 | 24 | 25 | 26 | 27 | 28 | 29 | 30 | 31 | 32 | 33 | 34 | 35 | 36 |
| | | | | | | | | 4-30 Kabat | | | | | | | | | | |
| | 18 | 19 | 20 | 21 | 22 | 23 | 24 | 25 | 26 | 27 | 28 | 29 | 30 | | 31 | 31a | 31b | |
| Region | | | | FR1 | | | | | | | | | CDR1 | | | | | |
| Germ. AA | L | S | L | T | C | T | V | S | G | G | S | I | S | | S | G | D | |
| Germ. Nuc | ctg | tcc | ctc | acc | tgc | act | gtc | tct | ggt | ggc | tcc | atc | agc | | agt | ggt | gat | |
| WR12 AA | L | S | L | T | C | T | V | S | G | D | S | V | S | | S | N | D | |
| WR12 Nuc | ctg | tcc | ctc | acc | tgc | act | gtc | tct | ggc | gac | tcc | gtc | agc | | agt | aat | gat | |
| WR13 AA | L | S | L | T | C | T | V | S | G | D | S | V | S | | S | N | D | |
| WR13 Nuc | ctg | tcc | ctc | acc | tgc | act | gtc | tct | ggc | gac | tcc | gtc | agc | | agt | aat | gat | |

| | | | | | | | | | | | | | | | | | | |
|---|---|---|---|---|---|---|---|---|---|---|---|---|---|---|---|---|---|---|
| | | | | | | | | 4-30 Codon | | | | | | | | | | |
| | 37 | 38 | 39 | 40 | 41 | 42 | 43 | 44 | 45 | 46 | 47 | 48 | 49 | 50 | 51 | 52 | 53 | 54 |
| | | | | | | | | 4-30 Kabat | | | | | | | | | | |
| | 32 | 33 | 34 | 35 | 36 | 37 | 38 | 39 | 40 | 41 | 42 | 43 | 44 | 45 | 46 | 47 | 48 | 49 |
| Region | CDR1 | | | | | | | | | | FR2 | | | | | | | |
| Germ. AA | Y | Y | W | S | W | I | R | Q | P | P | G | K | G | L | E | W | I | G |
| Germ. Nuc | tac | tac | tgg | agt | tgg | atc | cgc | cag | ccc | cca | ggg | aag | ggc | ctg | gag | tgg | att | ggg |
| WR12 AA | H | Y | W | S | W | I | R | Q | P | P | G | Q | G | L | E | W | I | G |
| WR12 Nuc | cac | tac | tgg | agt | tgg | atc | cgc | cag | ccc | cca | ggg | cag | ggc | ctg | gag | tgg | att | ggg |
| WR13 AA | H | Y | W | S | W | I | R | Q | P | P | G | Q | G | L | E | W | I | G |
| WR13 Nuc | cac | tac | tgg | agt | tgg | atc | cgc | cag | ccc | cca | ggg | cag | ggc | ctg | gag | tgg | att | ggg |

| | | | | | | | | | | | | | | | | | | |
|---|---|---|---|---|---|---|---|---|---|---|---|---|---|---|---|---|---|---|
| | | | | | | | | 4-30 Codon | | | | | | | | | | |
| | 55 | 56 | 57 | 58 | 59 | 60 | 61 | 62 | 63 | 64 | 65 | 66 | 67 | 68 | 69 | 70 | 71 | 72 |
| | | | | | | | | 4-30 Kabat | | | | | | | | | | |
| | 50 | 51 | 52 | 53 | 54 | | | | 55 | 56 | 57 | 58 | 59 | 60 | 61 | 62 | 63 | 64 |
| Region | FR2 | | | | | CDR2 | | | | | | | | | FR3 | | | |
| Germ. AA | Y | I | Y | Y | S | | | | G | S | T | Y | Y | N | P | S | L | K |
| Germ. Nuc | tac | atc | tat | tac | agt | | | | ggg | agc | acc | tac | tac | aac | ccg | tcc | ctc | aag |
| WR12 AA | Y | I | S | H | G | | | | G | T | T | Y | Y | N | P | S | L | K |
| WR12 Nuc | tac | atc | tct | cac | ggt | | | | ggg | acc | acc | tac | tac | aac | ccg | tcc | ctc | aag |
| WR13 AA | Y | I | S | H | G | | | | G | T | T | Y | Y | N | P | S | L | K |
| WR13 Nuc | tac | atc | tct | cac | ggt | | | | ggg | acc | acc | tac | tac | aac | ccg | tcc | ctc | aag |

| | | | | | | | | | | | | | | | | | | |
|---|---|---|---|---|---|---|---|---|---|---|---|---|---|---|---|---|---|---|
| | | | | | | | | 4-30 Codon | | | | | | | | | | |
| | 73 | 74 | 75 | 76 | 77 | 78 | 79 | 80 | 81 | 82 | 83 | 84 | 85 | 86 | 87 | 88 | 89 | 90 |
| | | | | | | | | 4-30 Kabat | | | | | | | | | | |
| | | 65 | 66 | 67 | 68 | 69 | 70 | 71 | 72 | 73 | 74 | 75 | 76 | 77 | 78 | 79 | 80 | 81 |
| Region | | | | | | | | | FR3 | | | | | | | | | |
| Germ. AA | | S | R | V | T | I | S | V | D | T | S | K | N | Q | F | S | L | K |
| Germ. Nuc | | agt | cga | gtt | acc | ata | tca | gta | gac | acg | tcc | aag | aac | cag | ttc | tcc | ctg | aag |
| WR12 AA | | S | R | V | T | M | S | I | D | T | S | T | N | Q | F | S | L | R |
| WR12 Nuc | | agt | cga | gtt | acc | atg | tcg | atc | gac | acg | tcc | aca | aac | cag | ttc | tcc | ctg | agg |
| WR13 AA | | S | R | V | T | M | S | I | D | T | S | T | N | Q | F | S | L | R |
| WR13 Nuc | | agt | cga | gtt | acc | atg | tcg | atc | gac | acg | tcc | acg | aac | cag | ttc | tcc | ctg | agg |

| | | | | | | | | | | | | | | | | |
|---|---|---|---|---|---|---|---|---|---|---|---|---|---|---|---|---|
| | | | | | | | | 4-30 Codon | | | | | | | | |
| | 91 | 92 | 93 | 94 | 95 | 96 | 97 | 98 | 99 | 100 | 101 | 102 | 103 | 104 | 105 | 106 | |
| | | | | | | | | 4-30 Kabat | | | | | | | | |
| | 82 | 82a | 82b | 82c | 83 | 84 | 85 | 86 | 87 | 88 | 89 | 90 | 91 | 92 | 93 | 94 | |
| Region | | | | | | | | FR3 | | | | | | | | CDR3 | |
| Germ. AA | L | S | S | V | T | A | A | D | T | A | V | Y | Y | C | A | R | A |
| Germ. Nuc | ctg | agc | tct | gtg | act | gcc | gca | gac | acg | gcc | gtg | tat | tac | tgt | gcc | aga | gca |
| WR12 AA | V | T | S | V | R | A | A | D | M | A | V | Y | F | C | A | R | A P |
| WR12 Nuc | gtg | acc | tcc | gtg | cga | gcc | gca | gac | atg | gcc | gtc | tac | ttc | tgt | gcc | agg | gcc ccg |
| WR13 AA | V | T | S | V | R | A | A | D | M | A | V | Y | F | C | A | R | A P |
| WR13 Nuc | gtg | acc | tcc | gtg | cga | gcc | gca | gac | atg | gcc | gtc | tac | ttc | tgt | gcc | agg | gcc ccg |

TABLE 1-continued

Heavy Chain Sequences of AGS Enriched CSF Antibodies 4-30 Codon
4-30 Kabat
CDR3

| Region | | | | | | | | | | | | | | | | |
|---|---|---|---|---|---|---|---|---|---|---|---|---|---|---|---|---|
| Germ. AA | | | | | | | | | | | | | | | | |
| Germ. Nuc | | | | | | | | | | | | | | | | |
| WR12 AA | A | P | I | T | T | F | G | M | V | T | P | V | P | Y | F | H | S |
| WR12 Nuc | gcc | cct | ata | acg | act | ttt | gga | atg | gtg | aca | cca | gtc | ccc | tac | ttt | cac | tcc |
| WR13 AA | A | P | I | T | T | F | G | M | V | T | P | V | P | Y | F | H | S |
| WR13 Nuc | gcc | cct | ata | acg | act | ttt | gga | atg | gtg | aca | cca | gtc | ccc | tac | ttt | cac | tcc |

(SEQ ID NOS: 1-6, top to bottom)

4-31 Codon

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|

4-31 Kabat

| Region | 1 | 2 | 3 | 4 | 5 | 6 | 7 | 8 FR1 | 9 | 10 | 11 | 12 | 13 | 14 | 15 | 16 | 17 |
|---|---|---|---|---|---|---|---|---|---|---|---|---|---|---|---|---|---|
| Germ. AA | Q | V | Q | L | Q | E | S | G | P | G | L | V | K | P | S | Q | T |
| Germ. Nuc | cag | gtg | cag | ctg | cag | gag | tcg | ggc | cca | gga | ctg | gtg | aag | cct | tca | cag | acc |
| AJL02 AA | Q | V | Q | L | Q | E | S | G | P | G | L | V | K | P | S | Q | T |
| AJL02 Nuc | cag | gtg | cag | ctg | cag | gag | tcg | ggc | cca | gga | ctg | gtg | aag | cct | tca | cag | acc |

4-31 Codon

| | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|

4-31 Kabat

| Region | 18 | 19 | 20 | 21 FR1 | 22 | 23 | 24 | 25 | 26 | 27 | 28 | 29 | 30 | 31 CDR1 | 31a | 31b |
|---|---|---|---|---|---|---|---|---|---|---|---|---|---|---|---|---|
| Germ. AA | L | S | L | T | C | T | V | S | G | G | S | I | S | | S | G | G |
| Germ. Nuc | ctg | tcc | ctc | acc | tgt | act | gtc | tct | ggt | ggc | tcc | atc | agc | | agt | ggt | ggt |
| AJL02 AA | L | S | L | T | C | T | V | S | G | G | S | I | S | | S | G | G |
| AJL02 Nuc | ctg | tcc | ctc | acc | tgt | act | gtc | tct | ggt | ggc | tcc | atc | agc | | agt | ggt | ggt |

4-31 Codon

| | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|

4-31 Kabat

| Region | 32 CDR1 | 33 | 34 | 35 | 36 | 37 | 38 | 39 | 40 | 41 | 42 FR2 | 43 | 44 | 45 | 46 | 47 | 48 | 49 |
|---|---|---|---|---|---|---|---|---|---|---|---|---|---|---|---|---|---|---|
| Germ. AA | Y | Y | W | S | W | I | R | Q | H | P | G | K | G | L | E | W | I | G |
| Germ. Nuc | tac | tac | tgg | agc | tgg | atc | cgc | cag | cac | cca | ggg | aag | ggc | ctg | gag | tgg | att | ggg |
| AJL02 AA | H | Y | W | S | W | I | R | Q | S | P | G | K | G | L | E | w | I | G |
| AJL02 Nuc | cac | tac | tgg | agc | tgg | atc | cgc | cag | tcc | cca | ggg | aag | ggc | ctg | gag | tgg | att | ggg |

4-31 Codon

| | 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|

4-31 Kabat

| Region | 50 FR2 | 51 | 52 | 53 | 54 CDR2 | | | | | 55 | 56 | 57 | 58 | 59 | 60 | 61 FR3 | 62 | 63 | 64 |
|---|---|---|---|---|---|---|---|---|---|---|---|---|---|---|---|---|---|---|---|
| Germ. AA | Y | I | Y | Y | S | | | | | G | S | T | Y | Y | N | P | S | L | K |
| Germ. Nuc | tac | atc | tat | tac | agt | | | | | ggg | agc | acc | tac | tac | aac | ccg | tcc | ctc | aag |
| AJL02 AA | N | V | Y | Y | S | | | | | G | S | T | Y | Y | T | P | S | L | D |
| AJL02 Nuc | aac | gtc | tat | tat | agt | | | | | gga | agc | acc | tac | tac | acc | ccg | tcc | ctc | gac |

4-31 Codon

| | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|

4-59 Kabat

| Region | 65 | 66 | 67 | 68 | 69 | 70 | 71 | 72 FR3 | 73 | 74 | 75 | 76 | 77 | 78 | 79 | 80 | 81 |
|---|---|---|---|---|---|---|---|---|---|---|---|---|---|---|---|---|---|---|
| Germ. AA | S | R | V | T | I | S | V | D | T | S | K | N | Q | F | S | L | K |
| Germ. Nuc | agt | cga | gtt | acc | ata | tca | gta | gac | acg | tct | aag | aac | cag | ttc | tcc | ctg | aag |
| AJL02 AA | S | R | L | T | I | S | L | D | T | S | K | N | Q | F | S | L | R |
| AJL02 Nuc | agc | cga | ctt | acc | ata | tca | tta | gac | acg | tct | aag | aac | cag | ttc | tcc | ctg | agg |

TABLE 1-continued

Heavy Chain Sequences of AGS Enriched CSF Antibodies

4-31 Codon

| | 91 | 92 | 93 | 94 | 95 | 96 | 97 | 98 | 99 | 100 | 101 | 102 | 103 | 104 | 105 | 106 | | |
|---|---|---|---|---|---|---|---|---|---|---|---|---|---|---|---|---|---|---|
| 4-31 Kabat | | | | | | | | | | | | | | | | | | |
| Region | 82 | 82a | 82b | 82c | 83 | 84 | 85 | 86 | 87 | 88 | 89 | 90 | 91 | 92 | 93 | 94 | | |
| | | | | FR3 | | | | | | | | | | | | CDR3 | | |
| Germ. AA | L | S | S | V | T | A | A | D | T | A | V | Y | Y | C | A | R | | |
| Germ. Nuc | ctg | agc | tct | gtg | act | gcc | gcg | gac | acg | gcc | gtg | tat | tac | tgt | gcg | aga | | |
| AJL02 AA | L | S | N | V | T | V | A | D | T | A | V | Y | Y | C | A | R | G | R |
| AJL02 Nuc | ctg | agt | aat | gtg | act | gtc | gcg | gac | acg | gcc | gtc | tat | tac | tgt | gcg | aga | ggt | aga |

4-31 Codon / 4-31 Kabat

| Region | | | | | | | | | | | | |
|---|---|---|---|---|---|---|---|---|---|---|---|---|
| | | | | | CDR3 | | | | | | | |
| Germ. AA | | | | | | | | | | | | |
| Germ. Nuc | | | | | | | | | | | | |
| AJL02 AA | N | W | E | G | E | F | D | P | W | G | Q | G |
| AJL02 Nuc | aat | tgg | gag | ggc | gaa | ttc | gac | ccc | tgg | ggc | caa | gga |

(SEQ ID NOS: 7-10, top to bottom)

4-34 Codon

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 4-34 Kabat | | | | | | | | | | | | | | | | | | |
| Region | 1 | 2 | 3 | 4 | 5 | 6 | 7 | 8 | 9 | 10 | 11 | 12 | 13 | 14 | 15 | 16 | 17 | |
| | | | | | | | | FR1 | | | | | | | | | | |
| Germ. AA | Q | V | Q | L | Q | Q | W | G | A | | G | L | L | K | P | S | E | T |
| Germ. Nuc | cag | gtg | cag | cta | cag | cag | tgg | ggc | gca | | gga | ctg | ttg | aag | cct | tcg | gag | acc |
| AJL01 AA | Q | V | Q | L | Q | Q | W | G | A | | G | L | L | K | P | S | E | T |
| AJL01 Nuc | cag | gtg | cag | cta | cag | cag | tgg | ggc | gca | | gga | ctg | ttg | aag | cct | tcg | gag | acc |
| AJL19 AA | Q | V | Q | L | Q | Q | W | G | A | | G | L | L | K | P | S | E | T |
| AJL19 Nuc | cag | gtg | cag | cta | cag | cag | tgg | ggc | gca | | gga | ctg | ttg | aag | cct | tcg | gag | acc |

4-34 Codon

| | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| 4-34 Kabat | | | | | | | | | | | | | | | | | | |
| Region | 18 | 19 | 20 | 21 | 22 | 23 | 24 | 25 | 26 | 27 | 28 | 29 | | | | | 30 | 31 |
| | | | | FR1 | | | | | | | | | CDR1 | | | | | |
| Germ. AA | L | S | L | T | C | A | V | Y | G | G | S | F | | | | | S | G |
| Germ. Nuc | ctg | tcc | ctc | acc | tgc | gct | gtc | tat | ggt | ggg | tcc | ttc | | | | | agt | ggt |
| AJL01 AA | L | S | L | T | C | A | V | Y | G | G | S | F | | | | | N | E |
| AJL01 Nuc | ctg | tcc | ctc | acc | tgc | gct | gtc | tat | ggt | ggg | tcc | ttc | | | | | aat | gaa |
| AJL19 AA | L | S | L | T | C | A | V | F | G | G | S | L | | | | | S | G |
| AJL19 Nuc | ctg | tcc | ctc | acc | tgc | gct | gtc | ttt | ggt | ggg | tcc | ctc | | | | | agt | ggt |

4-34 Codon

| | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|
| 4-34 Kabat | | | | | | | | | | | | | | | | | | |
| Region | 32 | 33 | 34 | 35 | 36 | 37 | 38 | 39 | 40 | 41 | 42 | 43 | 44 | 45 | 46 | 47 | 48 | 49 |
| | CDR1 | | | | | | | | | | FR2 | | | | | | | |
| Germ. AA | Y | Y | W | S | W | I | R | Q | P | P | G | K | G | L | E | W | I | G |
| Germ. Nuc | tac | tac | tgg | agc | tgg | atc | cgc | cag | ccc | cca | ggg | aag | ggg | ctg | gag | tgg | att | ggg |
| AJL01 AA | F | Y | W | S | W | I | R | Q | P | A | R | K | G | L | E | W | I | G |
| AJL01 Nuc | ttc | tac | tgg | agc | tgg | atc | cgt | cag | ccc | gca | cgg | aag | ggc | ctg | gag | tgg | att | gga |
| AJL19 AA | Y | Y | W | S | W | I | R | Q | P | P | G | K | G | P | E | W | I | A |
| AJL19 Nuc | tac | tac | tgg | agt | tgg | atc | cgc | cag | ccc | cca | ggg | aag | ggg | ccg | gag | tgg | att | gcg |

4-34 Codon

| | 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|
| 4-34 Kabat | | | | | | | | | | | | | | | | | | |
| Region | 50 | 51 | 52 | 53 | 54 | | | 55 | 56 | 57 | 58 | 59 | 60 | 61 | 62 | 63 | 64 | |
| | FR2 | | | | CDR2 | | | | | | | | | | FR3 | | | |
| Germ. AA | E | I | N | H | S | | | G | S | T | N | Y | N | P | S | L | K | |
| Germ. Nuc | gaa | atc | aat | cat | agt | | | gga | agc | acc | aac | tac | aac | ccg | tcc | ctc | aag | |

TABLE 1-continued

Heavy Chain Sequences of AGS Enriched CSF Antibodies

| | | | | | | | | | | | | | | |
|---|---|---|---|---|---|---|---|---|---|---|---|---|---|---|
| AJL01 AA | E | I | S | H | S | | G | R | A | N | Y | N | P | S | L | K |
| AJL01 Nuc | gaa | atc | agt | cat | agc | | gga | aga | gcc | aac | tac | aac | ccg | tcc | ctc | aag |
| AJL19 AA | E | I | N | H | S | | G | D | A | N | Y | N | P | S | L | K |
| AJL19 Nuc | gaa | atc | aat | cat | agt | | gga | gat | gcc | aac | tac | aac | ccg | tcc | ctc | aag |

| | | | | | | | | 4-34 Codon | | | | | | | | |
|---|---|---|---|---|---|---|---|---|---|---|---|---|---|---|---|---|
| | 73 | 74 | 75 | 76 | 77 | 78 | 79 | 80 | 81 | 82 | 83 | 84 | 85 | 86 | 87 | 88 | 89 | 90 |
| | | | | | | | | | 4-34 Kabat | | | | | | | | |
| | | 65 | 66 | 67 | 68 | 69 | 70 | 71 | 72 | 73 | 74 | 75 | 76 | 77 | 78 | 79 | 80 | 81 |
| Region | | | | | | | | | FR3 | | | | | | | | | |

| | | | | | | | | | | | | | | | | |
|---|---|---|---|---|---|---|---|---|---|---|---|---|---|---|---|---|
| Germ. AA | | S | R | V | T | I | S | V | D | T | S | K | N | Q | F | S | L | K |
| Germ. Nuc | | agt | cga | gtc | acc | ata | tca | gta | gac | acg | tcc | aag | aac | cag | ttc | tcc | ctg | aag |
| AJL01 AA | | S | R | V | T | L | S | V | D | R | S | K | N | Q | F | S | L | N |
| AJL01 Nuc | | agt | cgc | gtc | acc | ctg | tct | gta | gac | agg | tcc | aag | aac | cag | ttc | tcc | ctg | aac |
| AJL19 AA | | S | R | V | T | I | S | V | D | T | S | K | N | Q | F | S | L | K |
| AJL19 Nuc | | agt | cga | gtc | act | atc | tca | gta | gac | acg | tcc | aag | aac | cag | ttt | tcc | ctg | aag |

| | | | | | | | | 4-34 Codon | | | | | | | |
|---|---|---|---|---|---|---|---|---|---|---|---|---|---|---|---|
| | 91 | 92 | 93 | 94 | 95 | 96 | 97 | 98 | 99 | 100 | 101 | 102 | 103 | 104 | 105 | 106 |
| | | | | | | | | 4-34 Kabat | | | | | | | |
| | 82 | 82a | 82b | 82c | 83 | 84 | 85 | 86 | 87 | 88 | 89 | 90 | 91 | 92 | 93 | 94 |
| Region | | | | | FR3 | | | | | | | | | | | CDR3 |

| | | | | | | | | | | | | | | | | |
|---|---|---|---|---|---|---|---|---|---|---|---|---|---|---|---|---|
| Germ. AA | L | S | S | V | T | A | A | D | T | A | V | Y | Y | C | A | R | G |
| Germ. Nuc | ctg | agc | tct | gtg | acc | gcc | gcg | gac | acg | gct | gtg | tat | tac | tgt | gcg | aga | ggg |
| AJL01 AA | L | S | P | V | A | A | A | D | T | A | V | Y | Y | C | A | R | R | E |
| AJL01 Nuc | ctg | agc | cct | gtg | gcc | gcc | gcg | gac | aca | gct | gtc | tat | tac | tgt | gcg | cga | cgg | gag |
| AJL19 AA | M | S | S | V | T | V | V | D | T | A | L | Y | Y | C | A | T | Q | G |
| AJL19 Nuc | atg | agt | tct | gtg | acc | gtc | gca | gac | acg | gct | tta | tat | tac | tgt | gcg | act | caa | ggc |

| | | | | |
|---|---|---|---|---|
| | | 4-34 Codon | | |
| | | 4-34 Kabat | | |
| Region | | CDR3 | | |

| | | | | | | | | | | | |
|---|---|---|---|---|---|---|---|---|---|---|---|
| Germ. AA | | | | | | | | | | | |
| Germ. Nuc | | | | | | | | | | | |
| AJL01 AA | I | V | V | T | V | R | G | R | R | A | F | D | I |
| AJL01 Nuc | ata | gtc | gta | act | gtt | cgg | ggg | cgt | cgt | gct | ttt | gat | atc |
| AJL19 AA | S | R | L | T | T | F | A | F | D | V | | | |
| AJL19 Nuc | tct | agg | ttg | act | aca | ttc | gct | ttt | gat | gtg | | | |

(SEQ ID NOS: 11-16, top to bottom)

| | | | | | | | | 4-39 Codon | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| | | | | | | | | | 4-39 Kabat | | | | | | | | |
| | | 1 | 2 | 3 | 4 | 5 | 6 | 7 | 8 | 9 | 10 | 11 | 12 | 13 | 14 | 15 | 16 | 17 |
| Region | | | | | | | | | FR1 | | | | | | | | | |

| | | | | | | | | | | | | | | | | |
|---|---|---|---|---|---|---|---|---|---|---|---|---|---|---|---|---|
| Germ. AA | Q | L | Q | L | Q | E | S | G | P | | G | L | V | K | P | S | E | T |
| Germ. Nuc | cag | ctg | cag | ctg | cag | gag | tcg | ggc | cca | | gga | ctg | gtg | aag | cct | tcg | gag | acc |
| AJL03 AA | Q | L | Q | L | Q | E | S | G | P | | G | L | V | K | P | S | E | T |
| AJL03 Nuc | cag | ctg | cag | ctg | cag | gag | tcg | ggc | cca | | gga | ctg | gtg | aag | cct | tcg | gag | acc |
| AJL15 AA | Q | L | Q | L | Q | E | S | G | P | | G | L | V | K | P | S | E | T |
| AJL15 Nuc | cag | ctg | cag | ctg | cag | gag | tcg | ggc | cca | | gga | ctg | gtg | aag | cct | tcg | gag | acc |

TABLE 1-continued

Heavy Chain Sequences of AGS Enriched CSF Antibodies

| | 4-39 Codon | | | | | | | | | | | | | | | | | |
|---|---|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 34 | 35 | 36 |
| | 4-39 Kabat | | | | | | | | | | | | | | | | | |
| | 18 | 19 | 20 | 21 | 22 | 23 | 24 | 25 | 26 | 27 | 28 | 29 | 30 | | 31 | 31a | 31b | |
| Region | | | | FR1 | | | | | | | | | | CDR1 | | | | |
| Germ. AA | L | S | L | T | C | T | V | S | G | G | S | I | S | | S | S | S | |
| Germ. Nuc | ctg | tcc | ctc | acc | tgc | act | gtc | tct | ggt | ggc | tcc | atc | agc | | agt | agt | agt | |
| AJL03 AA | L | S | L | T | C | T | V | S | G | A | S | I | S | | S | S | R | |
| AJL03 Nuc | ctg | tcc | ctc | acg | tgc | act | gtc | tct | ggt | gcc | tcc | atc | agc | | agt | agt | cgt | |
| AJL15 AA | L | S | L | T | C | T | V | S | G | G | S | I | T | | S | R | N | |
| AJL15 Nuc | ctg | tcc | ctc | acc | tgc | act | gtc | tct | ggt | ggc | tcc | atc | acc | | agt | agg | aat | |

| | 4-39 Codon | | | | | | | | | | | | | | | | | |
|---|---|---|---|---|---|---|---|---|---|---|---|---|---|---|---|---|---|---|
| | 37 | 38 | 39 | 40 | 41 | 42 | 43 | 44 | 45 | 46 | 47 | 48 | 49 | 50 | 51 | 52 | 53 | 54 |
| | 4-39 Kabat | | | | | | | | | | | | | | | | | |
| | 32 | 33 | 34 | 35 | 36 | 37 | 38 | 39 | 40 | 41 | 42 | 43 | 44 | 45 | 46 | 47 | 48 | 49 |
| Region | CDR1 | | | | | | | | | | FR2 | | | | | | | |
| Germ. AA | Y | Y | W | G | W | I | R | Q | P | P | G | K | G | L | E | W | I | G |
| Germ. Nuc | Tac | tac | tgg | ggc | tgg | atc | cgc | cag | ccc | cca | ggg | aag | ggg | ctg | gag | tgg | att | ggg |
| AJL03 AA | S | Y | W | G | W | I | R | Q | P | P | G | K | G | L | E | W | I | G |
| AJL03 Nuc | Tcc | tac | tgg | ggc | tgg | atc | cgc | cag | ccc | cca | ggg | aag | ggg | ctg | gag | tgg | att | ggg |
| AJL15 AA | N | Y | W | G | W | I | R | Q | S | P | G | K | G | L | E | W | I | G |
| AJL15 Nuc | Aac | tac | tgg | ggc | tgg | atc | cgc | cag | tcc | cca | ggg | aag | ggg | ctg | gag | tgg | att | ggg |

| | 4-39 Codon | | | | | | | | | | | | | | | | | |
|---|---|---|---|---|---|---|---|---|---|---|---|---|---|---|---|---|---|---|
| | 55 | 56 | 57 | 58 | 59 | 60 | 61 | 62 | 63 | 64 | 65 | 66 | 67 | 68 | 69 | 70 | 71 | 72 |
| | 4-39 Kabat | | | | | | | | | | | | | | | | | |
| | 50 | 51 | 52 | 53 | 54 | | | | 55 | 56 | 57 | 58 | 59 | 60 | 61 | 62 | 63 | 64 |
| Region | FR2 | | | | CDR2 | | | | | | | | | | FR3 | | | |
| Germ. AA | S | I | Y | Y | S | | | | G | S | T | Y | Y | N | P | S | L | K |
| Germ. Nuc | Agt | atc | tat | tat | agt | | | | ggg | agc | acc | tac | tac | aac | ccg | tcc | ctc | aag |
| AJL03 AA | S | M | Y | Q | S | | | | G | S | T | Y | Y | S | P | S | L | K |
| AJL03 Nuc | Agt | atg | tat | caa | agt | | | | ggg | agc | act | tac | tac | agt | ccg | tcc | ctc | aag |
| AJL15 AA | S | L | Y | Y | T | | | | G | S | D | Y | Y | N | P | S | L | K |
| AJL15 Nuc | Agt | ctc | tat | tat | act | | | | ggg | agc | gac | tac | tac | aac | ccg | tcc | ctc | aag |

| | 4-39 Codon | | | | | | | | | | | | | | | | | |
|---|---|---|---|---|---|---|---|---|---|---|---|---|---|---|---|---|---|---|
| | 73 | 74 | 75 | 76 | 77 | 78 | 79 | 80 | 81 | 82 | 83 | 84 | 85 | 86 | 87 | 88 | 89 | 90 |
| | 4-39 Kabat | | | | | | | | | | | | | | | | | |
| | 65 | 66 | 67 | 68 | 69 | 70 | 71 | 72 | 73 | 74 | 75 | 76 | 77 | 78 | 79 | 80 | 81 | |
| Region | | | | | | | | FR3 | | | | | | | | | | |
| Germ. AA | S | R | V | T | I | S | V | D | T | S | K | N | Q | F | S | L | K | |
| Germ. Nuc | agt | cga | gtc | acc | ata | tca | gta | gac | acg | tcc | aag | aac | cag | ttc | tcc | ctg | aag | |
| AJL03 AA | S | R | V | T | I | S | M | D | T | S | K | N | Q | F | S | L | N | |
| AJL03 Nuc | agt | cga | gtc | acc | ata | tcc | atg | gac | acg | tcc | aag | aac | cag | ttc | tcc | cta | aac | |
| AJL15 AA | S | R | V | T | I | S | V | D | T | S | K | N | Q | F | S | L | R | |
| AJL15 Nuc | agt | cga | gtc | acc | ata | tcg | gta | gac | aca | tcg | aag | aac | caa | ttc | tcc | ctg | agg | |

| | 4-39 Codon | | | | | | | | | | | | | | | |
|---|---|---|---|---|---|---|---|---|---|---|---|---|---|---|---|---|
| | 91 | 92 | 93 | 94 | 95 | 96 | 97 | 98 | 99 | 100 | 101 | 102 | 103 | 104 | 105 | 106 |
| | 4-39 Kabat | | | | | | | | | | | | | | | |
| | 82 | 82a | 82b | 82c | 83 | 84 | 85 | 86 | 87 | 88 | 89 | 90 | 91 | 92 | 93 | 94 |
| Region | | | | | FR3 | | | | | | | | | | | CDR3 |
| Germ. AA | L | S | S | V | T | A | A | D | T | A | V | Y | Y | C | A | R | D |
| Germ. Nuc | ctg | agc | tct | gtg | acc | gcc | gcg | gac | acg | gcc | gtg | tat | tac | tgt | gcg | aga | gat |
| AJL03 AA | L | T | S | V | T | A | A | D | T | A | V | Y | F | C | A | R | H | S |
| AJL03 Nuc | ctg | acg | tct | gtg | acc | gcc | gcg | gac | acg | gct | gtg | tat | tc | tgt | gcg | aga | cat | tcg |
| AJL15 AA | L | S | S | V | T | A | A | D | T | A | V | Y | Y | C | V | R | V | N |
| AJL15 Nuc | ctg | agt | tct | gtg | acc | gcc | gcg | gac | acg | gcc | gtg | tat | tat | tgt | gtc | aga | gtt | aac |

TABLE 1-continued

Heavy Chain Sequences of AGS Enriched CSF Antibodies

4-39 Codon / 4-39 Kabat CDR3

| Region | | | | | | | | | | | | | | | |
|---|---|---|---|---|---|---|---|---|---|---|---|---|---|---|---|
| Germ. AA | | | | | | | | | | | | | | | |
| Germ. Nuc | | | | | | | | | | | | | | | |
| AJL03 AA | N | P | G | T | A | N | K | L | R | L | G | E | F | S | P |
| AJL03 Nuc | aac | ccc | gga | acg | gcg | aac | aaa | ttg | cgt | ttg | ggg | gag | ttt | tcg | ccc |
| AJL15 AA | V | D | D | F | W | S | G | L | G | G | A | W | F | D | P |
| AJL15 Nuc | gta | gac | gac | ttt | tgg | agt | ggt | tta | ggg | ggg | gcc | tgg | ttc | gac | ccc |

(SEQ ID NOS: 17-22, top to bottom)

4-4 Codon

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 4-4 Kabat | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | |
| Region | | | | | | | | FR1 | | | | | | | | | | |
| Germ. AA | Q | V | Q | L | Q | E | S | G | P | G | L | V | K | P | S | E | T | |
| Germ. Nuc | cag | gtg | cag | ctg | cag | gag | tcg | ggc | cca | gga | ctg | gtg | aag | cct | tcg | gag | acc | |
| AJL10 AA | Q | V | Q | L | Q | E | S | G | P | G | L | V | K | P | S | E | T | |
| AJL10 Nuc | cag | gtg | cag | ctg | cag | gag | tcg | ggc | cca | gga | ctg | gtg | aag | cct | tcg | gag | acc | |
| WR10 AA | Q | V | Q | L | Q | E | S | G | P | G | L | V | K | P | S | G | T | |
| WR10 Nuc | cag | gtg | cag | ctg | cag | gag | tcg | ggc | cca | gga | ctg | gtg | aag | cct | tcg | ggg | acc | |

4-4 Codon

| | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|
| 4-4 Kabat | | | | | | | | | | | | | | | | | | |
| | 18 | 19 | 20 | 21 | 22 | 23 | 24 | 25 | 26 | 27 | 28 | 29 | | | | | 30 | 31 |
| Region | | | FR1 | | | | | | | | | | CDR1 | | | | | |
| Germ. AA | L | S | L | T | C | T | V | S | G | G | S | I | | | | | S | S |
| Germ. Nuc | ctg | tcc | ctc | acc | tgc | act | gtc | tct | ggt | ggc | tcc | atc | | | | agt | agt | |
| AJL10 AA | L | S | L | T | C | S | V | S | G | G | A | V | | | | | S | N |
| AJL10 Nuc | ctg | tcc | ctc | acg | tgc | agt | gtc | tct | ggt | ggc | gcc | gtc | | | | agt | aat | |
| WR10 AA | L | S | L | T | C | A | V | S | G | G | S | I | S | | | | N | N |
| WR10 Nuc | ctg | tcc | ctc | acc | tgc | gct | gtc | tct | ggt | ggc | tcc | atc | agc | | | aat | aat | |

4-4 Codon

| | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|
| 4-4 Kabat | | | | | | | | | | | | | | | | | | |
| | 32 | 33 | 34 | 35 | 36 | 37 | 38 | 39 | 40 | 41 | 42 | 43 | 44 | 45 | 46 | 47 | 48 | 49 |
| Region | CDR1 | | | | | | | | | | FR2 | | | | | | | |
| Germ. AA | Y | Y | W | S | W | I | R | Q | P | A | G | K | G | L | E | W | I | G |
| Germ. Nuc | tac | tac | tgg | agc | tgg | atc | cgg | cag | ccc | gcc | ggg | aag | gga | ctg | gag | tgg | att | ggg |
| AJL10 AA | Y | Y | W | S | W | I | R | Q | S | A | G | K | G | L | E | W | L | G |
| AJL10 Nuc | tac | tac | tgg | agt | tgg | atc | cgg | cag | tcc | gcc | ggg | aag | gga | ctg | gag | tgg | ctt | ggg |
| WR10 AA | K | W | W | N | W | V | R | Q | S | P | G | K | G | L | E | W | I | G |
| WR10 Nuc | aag | tgg | tgg | aat | tgg | gtc | cgc | cag | tcc | cca | ggg | aag | ggg | ctg | gag | tgg | att | ggg |

4-4 Codon

| | 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|
| 4-4 Kabat | | | | | | | | | | | | | | | | | | |
| | 50 | 51 | 52 | 53 | 54 | | | | 55 | 56 | 57 | 58 | 59 | 60 | 61 | 62 | 63 | 64 |
| Region | FR2 | | | | | CDR2 | | | | | | | | | FR3 | | | |
| Germ. AA | R | I | Y | T | S | | | | G | S | T | N | Y | N | P | S | L | K |
| Germ. Nuc | cgt | atc | tat | acc | agt | | | | ggg | agc | acc | aac | tac | aac | ccc | tcc | ctc | aag |
| AJL10 AA | R | I | Y | I | N | | | | G | T | T | Y | Y | N | P | S | L | R |
| AJL10 Nuc | cgg | atc | tat | atc | aat | | | | gga | act | act | tac | tac | aac | ccc | tcc | ctc | agg |
| WR10 AA | E | I | Y | H | S | | | | G | G | T | N | Y | N | P | S | L | K |
| WR10 Nuc | gaa | atc | tat | cat | agt | | | | ggg | ggc | acc | aac | tac | aac | ccg | tcc | ctc | aag |

TABLE 1-continued

Heavy Chain Sequences of AGS Enriched CSF Antibodies

| | | | | | | | | | 4-4 Codon | | | | | | | | | |
|---|---|---|---|---|---|---|---|---|---|---|---|---|---|---|---|---|---|---|
| | 73 | 74 | 75 | 76 | 77 | 78 | 79 | 80 | 81 | 82 | 83 | 84 | 85 | 86 | 87 | 88 | 89 | 90 |
| | | | | | | | | | 4-4 Kabat | | | | | | | | | |
| | 65 | 66 | 67 | 68 | 69 | 70 | 71 | 72 | 73 | 74 | 75 | 76 | 77 | 78 | 79 | 80 | 81 | |
| Region | | | | | | | | | FR3 | | | | | | | | | |
| Germ. AA | S | R | V | T | M | S | V | D | T | S | K | N | Q | F | S | L | K | |
| Germ. Nuc | agt | cga | gtc | acc | atg | tca | gta | gac | acg | tcc | aag | aac | cag | ttc | tcc | ctg | aag | |
| AJL10 AA | S | R | V | S | M | S | V | D | T | S | K | G | Q | F | S | L | R | |
| AJL10 Nuc | agc | cgg | gtc | tcc | atg | tca | gtt | gac | acg | tcc | aag | ggc | cag | ttc | tcc | ctg | agg | |
| WR10 AA | S | R | V | T | I | S | V | D | K | S | K | N | L | F | S | L | K | |
| WR10 Nuc | agt | cga | gtc | acc | ata | tcg | gta | gac | aag | tcc | aag | aac | ctg | ttc | tcc | ctg | aag | |

| | | | | | | | | | 4-4 Codon | | | | | | |
|---|---|---|---|---|---|---|---|---|---|---|---|---|---|---|---|
| | 91 | 92 | 93 | 94 | 95 | 96 | 97 | 98 | 99 | 100 | 101 | 102 | 103 | 104 | 105 | 106 |
| | | | | | | | | | 4-4 Kabat | | | | | | |
| | 82 | 82a | 82b | 82c | 83 | 84 | 85 | 86 | 87 | 88 | 89 | 90 | 91 | 92 | 93 | 94 |
| Region | | | | | FR3 | | | | | | | | | | | CDR3 |
| Germ. AA | L | S | S | V | T | A | A | D | T | A | V | Y | Y | C | A | R |
| Germ. Nuc | ctg | agc | tct | gtg | acc | gcc | gcg | gac | acg | gcc | gtg | tat | tac | tgt | gcg | aga |
| AJL10 AA | L | T | S | V | T | A | A | D | T | A | I | Y | Y | C | A | R | W | G |
| AJL10 Nuc | ttg | acc | tct | gtg | acc | gcc | gcg | gac | acg | gcc | ata | tat | tat | tgt | gcg | aga | tgg | ggt |
| WR10 AA | L | S | S | V | T | A | A | D | T | A | V | Y | Y | C | A | S | A | T |
| WR10 Nuc | ctg | agc | tct | gtg | acc | gcc | gcg | gac | acg | gcc | gtg | tat | tac | tgt | gcg | agt | gcg | act |

| | | | | | | | 4-4 Codon | | | | | | |
|---|---|---|---|---|---|---|---|---|---|---|---|---|---|---|
| | | | | | | | 4-4 Kabat | | | | | | |
| Region | | | | | | | CDR3 | | | | | | |
| Germ. AA | | | | | | | | | | | | | | |
| Germ. Nuc | | | | | | | | | | | | | | |
| AJL10 AA | A | L | L | G | D | Y | Y | Y | G | L | D | V | | |
| AJL10 Nuc | gcc | cta | ttg | ggc | gac | tac | tat | tac | ggt | ttg | gac | gtc | | |
| WR10 AA | T | M | V | R | G | L | S | L | Y | Y | Y | G | L | D | V |
| WR10 Nuc | act | atg | gtt | cgg | gga | ctg | agt | ctt | tac | tac | tac | ggt | ctg | gac | gtc |

(SEQ ID NOS: 23-28, top to bottom)

| | | | | | | | | | 4-59 Codon | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| | | | | | | | | | 4-59 Kabat | | | | | | | | | |
| | 1 | 2 | 3 | 4 | 5 | 6 | 7 | 8 | 9 | 10 | 11 | 12 | 13 | 14 | 15 | 16 | 17 | |
| Region | | | | | | | | | FR1 | | | | | | | | | |
| Germ. AA | Q | V | Q | L | Q | E | S | G | P | G | L | V | K | P | S | E | T | |
| Germ. Nuc | cag | gtg | cag | ctg | cag | gag | tcg | ggc | cca | gga | ctg | gtg | aag | cct | tcg | gag | acc | |
| AJL07 AA | Q | V | Q | L | Q | E | S | G | P | G | L | V | K | P | S | E | T | |
| AJL07 Nuc | cag | gtg | cag | ctg | cag | gag | tcg | ggc | cca | gga | ctg | gtg | aag | cct | tcg | gag | acc | |

| | | | | | | | | 4-59 Codon | | | | | | | | | |
|---|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 34 | 35 | 36 |
| | | | | | | | | 4-59 Kabat | | | | | | | | | |
| | 18 | 19 | 20 | 21 | 22 | 23 | 24 | 25 | 26 | 27 | 28 | 29 | | | | | 30 | 31 |
| Region | | | FR1 | | | | | | | | | | CDR1 | | | | | |
| Germ. AA | L | S | L | T | C | T | V | S | G | G | S | I | | | | | S | S |
| Germ. Nuc | ctg | tcc | ctc | acc | tgc | act | gtc | tct | ggt | ggc | tcc | atc | | | | | agt | agt |
| AJL07 AA | L | S | L | T | C | T | V | S | G | G | S | I | | | | | N | N |
| AJL07 Nuc | ctg | tcc | ctc | acc | tgc | act | gtc | tct | ggt | ggc | tcc | atc | | | | | aac | aac |

| | | | | | | | | | 4-59 Codon | | | | | | | | | |
|---|---|---|---|---|---|---|---|---|---|---|---|---|---|---|---|---|---|---|
| | 37 | 38 | 39 | 40 | 41 | 42 | 43 | 44 | 45 | 46 | 47 | 48 | 49 | 50 | 51 | 52 | 53 | 54 |
| | | | | | | | | | 4-59 Kabat | | | | | | | | | |
| | 32 | 33 | 34 | 35 | 36 | 37 | 38 | 39 | 40 | 41 | 42 | 43 | 44 | 45 | 46 | 47 | 48 | 49 |
| Region | CDR1 | | | | | | | | | | FR2 | | | | | | | |
| Germ. AA | Y | Y | W | S | W | I | R | Q | P | P | G | K | G | L | E | W | I | G |
| Germ. Nuc | tac | tac | tgg | agc | tgg | atc | cgg | cag | ccc | cca | ggg | aag | gga | ctg | gag | tgg | att | ggg |

TABLE 1-continued

Heavy Chain Sequences of AGS Enriched CSF Antibodies

| AJL07 AA | Y | Y | W | S | W | I | R | Q | P | P | G | K | G | L | E | W | I | G |
|---|---|---|---|---|---|---|---|---|---|---|---|---|---|---|---|---|---|---|
| AJL07 Nuc | tat | tac | tgg | agt | tgg | atc | cgg | cag | ccc | cca | ggg | aag | gga | ctg | gag | tgg | att | ggt |

| | | | | | | | | | 4-59 Codon | | | | | | | | | |
|---|---|---|---|---|---|---|---|---|---|---|---|---|---|---|---|---|---|---|
| | 55 | 56 | 57 | 58 | 59 | 60 | 61 | 62 | 63 | 64 | 65 | 66 | 67 | 68 | 69 | 70 | 71 | 72 |
| | | | | | | | | | 4-59 Kabat | | | | | | | | | |
| | 50 | 51 | 52 | 53 | 54 | | | | 55 | 56 | 57 | 58 | 59 | 60 | 61 | 62 | 63 | 64 |
| Region | FR2 | | | | | CDR2 | | | | | | | | | FR3 | | | |
| Germ. AA | Y | I | Y | Y | N | | | | G | S | T | N | Y | N | P | S | L | K |
| Germ. Nuc | tat | atc | tat | tac | aat | | | | ggg | agc | acc | aac | tac | aac | ccc | tcc | ctc | aag |
| AJL07 AA | Y | I | Y | Y | N | | | | G | N | I | N | Y | N | P | S | L | K |
| AJL07 Nuc | tat | atc | tat | tac | aat | | | | ggg | aat | att | aat | tac | aac | cct | tcc | ctc | aag |

| | | | | | | | | | 4-59 Codon | | | | | | | | | |
|---|---|---|---|---|---|---|---|---|---|---|---|---|---|---|---|---|---|---|
| | 73 | 74 | 75 | 76 | 77 | 78 | 79 | 80 | 81 | 82 | 83 | 84 | 85 | 86 | 87 | 88 | 89 | 90 |
| | | | | | | | | | 4-59 Kabat | | | | | | | | | |
| | | 65 | 66 | 67 | 68 | 69 | 70 | 71 | 72 | 73 | 74 | 75 | 76 | 77 | 78 | 79 | 80 | 81 |
| Region | | | | | | | | | FR3 | | | | | | | | | |
| Germ. AA | | S | R | V | T | I | S | V | D | T | S | K | N | Q | F | S | L | K |
| Germ. Nuc | | agt | cga | gtc | acc | Ata | tca | gta | gac | acg | tcc | aag | aac | cag | ttc | tcc | ctg | aag |
| AJL07 AA | | S | R | V | T | I | S | R | D | M | S | K | N | Q | F | S | L | N |
| AJL07 Nuc | | agt | cga | gtc | acc | Ata | tca | aga | gac | atg | tcc | aag | aac | cag | ttc | tcc | ctg | aac |

| | | | | | | | | | 4-59 Codon | | | | | | | |
|---|---|---|---|---|---|---|---|---|---|---|---|---|---|---|---|---|
| | 91 | 92 | 93 | 94 | 95 | 96 | 97 | 98 | 99 | 100 | 101 | 102 | 103 | 104 | 105 | 106 |
| | | | | | | | | | 4-59 Kabat | | | | | | | |
| | 82 | 82a | 82b | 82c | 83 | 84 | 85 | 86 | 87 | 88 | 89 | 90 | 91 | 92 | 93 | 94 |
| Region | | | | | FR3 | | | | | | | | | | | CDR3 |
| Germ. AA | L | S | S | V | T | A | A | D | T | A | V | Y | Y | C | A | R | E |
| Germ. Nuc | ctg | agc | tct | gtg | acc | gct | gcg | gac | acg | gcc | gtg | tat | tac | tgt | gcg | aga | gaa |
| AJL07 AA | L | R | S | V | T | A | A | D | T | A | V | Y | Y | C | G | I | G | Y |
| AJL07 Nuc | ctg | cgg | tct | gtg | acc | gct | gcg | gac | acg | gcc | gtg | tat | tac | tgt | gga | att | gga | tat |

| | | | | | | | | | 4-59 Codon | |
|---|---|---|---|---|---|---|---|---|---|---|
| | | | | | | | | | 4-59 Kabat | |
| Region | | | | | | | | | CDR3 | |
| Germ. AA | | | | | | | | | | |
| Germ. Nuc | | | | | | | | | | |
| AJL07 AA | S | A | V | A | A | G | T | V | D | Y |
| AJL07 Nuc | agt | gcg | gtg | gca | gct | ggt | aca | gtt | gac | tac |

(SEQ ID NOS: 29-32, top to bottom)

TABLE 2

Light Chain Sequences of AGS Enriched CSF Antibodies

| | | | | | | | | | 1-13 Codon | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| | | | | | | | | | 1-13 Kabat | | | | | | | | | |
| | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | FR1 | | | | | | | | | |
| Germ. AA | A | I | Q | L | T | Q | S | P | S | S | L | S | A | S | V | G | D | R | V |
| Germ. Nuc | gcc | atc | cag | ttg | acc | cag | tct | cca | tcc | tcc | ctg | tct | gca | tct | gta | gga | gac | aga | gtc |
| AJL07 AA | A | I | Q | L | T | Q | S | P | S | S | L | S | A | S | V | G | D | R | V |
| AJL07 Nuc | gcc | atc | cag | ttg | acc | cag | tct | cca | tcc | tcc | ctg | tct | gca | tct | gtg | gga | gac | aga | gtc |

TABLE 2-continued

Light Chain Sequences of AGS Enriched CSF Antibodies

| | 1-13 Codon | | | | | | | | | | | | | | | | | | |
|---|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 34 | 35 | 36 | 37 | 38 |
| | | | | | | | | | | | 1-13 Kabat | | | | | | | | |
| | 20 | 21 | 22 | 23 | 24 | 25 | 26 | 27 | 28 | 29 | | | | | | | 30 | 31 | 32 |
| Region | | | | FR1 | | | | | | | | | | CDR1 | | | | | |
| Germ. AA | T | I | T | C | R | A | S | Q | G | I | | | | | | | S | S | A |
| Germ. Nuc | acc | atc | act | tgc | cgg | gca | agt | cag | ggc | att | | | | | | | agc | agt | gct |
| AJL07 AA | T | I | T | C | R | A | S | Q | G | I | | | | | | | S | S | G |
| AJL07 Nuc | acc | atc | act | tgc | cgg | gca | agt | cag | ggc | att | | | | | | | agc | agt | ggt |

| | 1-13 Codon | | | | | | | | | | | | | | | | | | |
|---|---|---|---|---|---|---|---|---|---|---|---|---|---|---|---|---|---|---|---|
| | 39 | 40 | 41 | 42 | 43 | 44 | 45 | 46 | 47 | 48 | 49 | 50 | 51 | 52 | 53 | 54 | 55 | 56 | 57 |
| | | | | | | | | | | | 1-13 Kabat | | | | | | | | |
| | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | | CDR2 |
| Germ. AA | L | A | W | Y | Q | Q | K | P | G | K | A | P | K | L | L | I | Y | D | A |
| Germ. Nuc | tta | gcc | tgg | tat | cag | cag | aaa | cca | ggg | aag | gct | cct | aaa | ctc | ctg | atc | tat | gat | gcc |
| AJL07 AA | L | A | W | Y | Q | Q | E | P | G | K | A | P | K | L | L | I | Y | D | A |
| AJL07 Nuc | tta | gcc | tgg | tat | cag | cag | gaa | cca | ggg | aaa | gct | cct | aaa | ctc | ctg | atc | tat | gat | gcc |

| | 1-13 Codon | | | | | | | | | | | | | | | | | | |
|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 |
| | | | | | | | | | | | 1-13 Kabat | | | | | | | | |
| | | | | | | | | 52 | 53 | 54 | 55 | 56 | 57 | 58 | 59 | | 60 | 61 | 62 |
| Region | | | CDR2 | | | | | | | | | | | FR3 | | | | | |
| Germ. AA | | | | | | | | S | S | L | E | S | G | V | P | | S | R | F |
| Germ. Nuc | | | | | | | | tcc | agt | ttg | gaa | agt | ggg | gtc | cca | | tca | agg | ttc |
| AJL07 AA | | | | | | | | S | T | L | E | S | G | V | P | | S | R | F |
| AJL07 Nuc | | | | | | | | tcc | act | ttg | gaa | agt | ggg | gtc | cca | | tca | aga | ttc |

| | 1-13 Codon | | | | | | | | | | | | | | | | | | |
|---|---|---|---|---|---|---|---|---|---|---|---|---|---|---|---|---|---|---|---|
| | 77 | 78 | 79 | 80 | 81 | 82 | 83 | 84 | 85 | 86 | 87 | 88 | 89 | 90 | 91 | 92 | 93 | 94 | 95 |
| | | | | | | | | | | | 1-13 Kabat | | | | | | | | |
| | 63 | 64 | 65 | 66 | | | 67 | 68 | 69 | 70 | 71 | 72 | 73 | 74 | 75 | 76 | 77 | 78 | 79 |
| Region | | | | | | | | | | | FR3 | | | | | | | | |
| Germ. AA | S | G | S | G | | | S | G | T | D | F | T | L | T | I | S | S | L | Q |
| Germ. Nuc | agc | ggc | agt | gga | | | tct | ggg | aca | gat | ttc | act | ctc | acc | atc | agc | agc | ctg | cag |
| AJL07 AA | S | G | S | G | | | S | A | I | D | F | T | L | T | I | S | S | L | Q |
| AJL07 Nuc | agc | ggc | agt | gga | | | tct | gca | ata | gat | ttc | act | ctc | acc | atc | agc | agt | ctg | cag |

| | 1-13 Codon | | | | | | | | | | | | | | | | | | |
|---|---|---|---|---|---|---|---|---|---|---|---|---|---|---|---|---|---|---|---|
| | 96 | 97 | 98 | 99 | 100 | 101 | 102 | 103 | 104 | 105 | 106 | 107 | 108 | 109 | 110 | 111 | | | |
| | | | | | | | | | | | 1-13 Kabat | | | | | | | | |
| | 80 | 81 | 82 | 83 | 84 | 85 | 86 | 87 | 88 | 89 | 90 | 91 | 92 | | | | | | |
| Region | | | | | FR3 | | | | | | | | | CDR3 | | | | | |
| Germ. AA | P | E | D | F | A | T | Y | Y | C | Q | Q | F | N | S | Y | P | | | |
| Germ. Nuc | cct | gaa | gat | ttt | gca | act | tat | tac | tgt | caa | cag | ttt | aat | agt | tac | cct | | | |
| AJL07 AA | P | E | D | F | A | T | Y | Y | C | Q | Q | F | N | T | F | P | Y | T | |
| AJL07 Nuc | cct | gaa | gat | ttt | gca | act | tat | tac | tgt | caa | cag | ttt | aat | act | ttc | ccg | tat | act | |

(SEQ ID NOS: 33-36, top to bottom)

| | 1-33 Codon | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| | | | | | | | | | | | 1-33 Kabat | | | | | | | | |
| | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | | | FR1 | | | | | | | | |
| Germ. AA | D | I | Q | M | T | Q | S | P | S | S | L | S | A | S | V | G | D | R | V |
| Germ. Nuc | gac | atc | cag | atg | acc | cag | tct | cca | tcc | tcc | ctg | tct | gca | tct | gta | gga | gac | aga | gtc |

TABLE 2-continued

Light Chain Sequences of AGS Enriched CSF Antibodies

| AJL03 AA  | D   | I   | Q   | M   | T   | Q   | S   | P   | S   | S   | L   | S   | A   | S   | V   | G   | D   | R   | V   |
|-----------|-----|-----|-----|-----|-----|-----|-----|-----|-----|-----|-----|-----|-----|-----|-----|-----|-----|-----|-----|
| AJL03 Nuc | gac | atc | cag | atg | acc | cag | tct | cca | tcc | tcc | ctg | tct | gca | tct | gta | gga | gac | aga | gtc |

| 1-33 Codon | | | | | | | | | | | | | | | | | | | |
|---|---|---|---|---|---|---|---|---|---|---|---|---|---|---|---|---|---|---|---|
| 20 | 21 | 22 | 23 | 24 | 25 | 26 | 27 | 28 | 29 | 30 | 31 | 32 | 33 | 34 | 35 | 36 | 37 | 38 | |
| 1-33 Kabat | | | | | | | | | | | | | | | | | | | |
| 20 | 21 | 22 | 23 | 24 | 25 | 26 | 27 | 28 | 29 | | | | | | | 30 | 31 | 32 | |

| Region | FR1 | | | | | | | | | | CDR1 | | | | | | | | | |
|---|---|---|---|---|---|---|---|---|---|---|---|---|---|---|---|---|---|---|---|---|
| Germ. AA | T | I | T | C | Q | A | S | Q | D | I | | | | | | | S | N | Y | |
| Germ. Nuc | acc | atc | act | tgc | cag | gcg | agt | cag | gac | att | | | | | | | agc | aac | tat | |
| AJL03 AA | T | I | T | C | Q | A | S | Q | D | I | | | | | | | N | N | Y | |
| AJL03 Nuc | acc | atc | act | tgc | cag | gcg | agt | cag | gac | att | | | | | | | aac | aac | tat | |

| 1-33 Codon | | | | | | | | | | | | | | | | | | | |
|---|---|---|---|---|---|---|---|---|---|---|---|---|---|---|---|---|---|---|---|
| 39 | 40 | 41 | 42 | 43 | 44 | 45 | 46 | 47 | 48 | 49 | 50 | 51 | 52 | 53 | 54 | 55 | 56 | 57 | |
| 1-33 Kabat | | | | | | | | | | | | | | | | | | | |
| 33 | 34 | 35 | 36 | 37 | 38 | 39 | 40 | 41 | 42 | 43 | 44 | 45 | 46 | 47 | 48 | 49 | 50 | 51 | |

| Region | FR2 | | | | | | | | | | | | | | | | | CDR2 | |
|---|---|---|---|---|---|---|---|---|---|---|---|---|---|---|---|---|---|---|---|
| Germ. AA | L | N | W | Y | Q | Q | K | P | G | K | A | P | K | L | L | I | Y | D | A |
| Germ. Nuc | tta | aat | tgg | tat | cag | cag | aaa | cca | ggg | aaa | gcc | cct | aag | ctc | ctg | atc | tac | gat | gca |
| AJL03 AA | L | N | W | F | Q | Q | Q | P | G | K | A | P | K | L | L | I | Y | D | A |
| AJL03 Nuc | tta | aat | tgg | ttt | cag | cag | caa | cca | ggg | aaa | gcc | cct | aag | ctg | ctg | atc | tac | gat | gca |

| 1-33 Codon | | | | | | | | | | | | | | | | | | | |
|---|---|---|---|---|---|---|---|---|---|---|---|---|---|---|---|---|---|---|---|
| 58 | 59 | 60 | 61 | 62 | 63 | 64 | 65 | 66 | 67 | 68 | 69 | 70 | 71 | 72 | 73 | 74 | 75 | 76 | |
| 1-33 Kabat | | | | | | | | | | | | | | | | | | | |
| | | | | | | | 52 | 53 | 54 | 55 | 56 | 57 | 58 | 59 | | 60 | 61 | 62 | |

| Region | CDR2 | | | | | | | | | | | | FR3 | | | | | | |
|---|---|---|---|---|---|---|---|---|---|---|---|---|---|---|---|---|---|---|---|
| Germ. AA | | | | | | | | S | N | L | E | T | G | V | P | | S | R | F |
| Germ. Nuc | | | | | | | | tcc | aat | ttg | gaa | aca | ggg | gtc | cca | | tca | agg | ttc |
| AJL03 AA | | | | | | | | S | K | L | Q | M | G | V | P | | S | R | F |
| AJL03 Nuc | | | | | | | | tcc | aaa | ttg | caa | atg | ggg | gtc | cca | | tca | agg | ttc |

| 1-33 Codon | | | | | | | | | | | | | | | | | | | |
|---|---|---|---|---|---|---|---|---|---|---|---|---|---|---|---|---|---|---|---|
| 77 | 78 | 79 | 80 | 81 | 82 | 83 | 84 | 85 | 86 | 87 | 88 | 89 | 90 | 91 | 92 | 93 | 94 | 95 | |
| 1-33 Kabat | | | | | | | | | | | | | | | | | | | |
| 63 | 64 | 65 | 66 | | 67 | 68 | 69 | 70 | 71 | 72 | 73 | 74 | 75 | 76 | 77 | 78 | 79 | | |

| Region | FR3 | | | | | | | | | | | | | | | | | | |
|---|---|---|---|---|---|---|---|---|---|---|---|---|---|---|---|---|---|---|---|
| Germ. AA | S | G | S | G | | S | G | T | D | F | T | F | T | I | S | S | L | Q | |
| Germ. Nuc | agt | gga | agt | gga | | tct | ggg | aca | gat | ttt | act | ttc | acc | atc | agc | agc | ctg | cag | |
| AJL03 AA | S | G | S | A | | S | G | T | D | F | T | F | T | I | S | S | L | Q | |
| AJL03 Nuc | agt | gga | agt | gca | | tct | ggg | aca | gat | ttt | act | ttt | acc | atc | agc | agc | ctg | cag | |

| 1-33 Codon | | | | | | | | | | | | | | | | |
|---|---|---|---|---|---|---|---|---|---|---|---|---|---|---|---|---|
| 96 | 97 | 98 | 99 | 100 | 101 | 102 | 103 | 104 | 105 | 106 | 107 | 108 | 109 | 110 | 111 | |
| 1-33 Kabat | | | | | | | | | | | | | | | | |
| 80 | 81 | 82 | 83 | 84 | 85 | 86 | 87 | 88 | 89 | 90 | 91 | 92 | | | | |

| Region | FR3 | | | | | | | | | CDR3 | | | | | | |
|---|---|---|---|---|---|---|---|---|---|---|---|---|---|---|---|---|
| Germ. AA | P | E | D | I | A | T | Y | Y | C | Q | Q | Y | D | N | L | P | |
| Germ. Nuc | cct | gaa | gat | att | gca | aca | tat | tac | tgt | caa | cag | tat | gat | aat | ctc | cct | |
| AJL03 AA | P | E | D | I | G | T | Y | Y | C | Q | Q | Y | Y | N | L | P | Y | T |
| AJL03 Nuc | cct | gaa | gat | att | ggc | aca | tat | tac | tgt | caa | cag | tat | tat | aat | ctc | ccg | tac | act |

(SEQ ID NOS: 37-40, top to bottom)

TABLE 2-continued

Light Chain Sequences of AGS Enriched CSF Antibodies

| | 1-39 Codon | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| | 1-39 Kabat | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 |
| Region | FR1 | | | | | | | | | | | | | | | | | | |
| Germ. AA | D | I | Q | M | T | Q | S | P | S | S | L | S | A | S | V | G | D | R | V |
| Germ. Nuc | gac | atc | cag | atg | acc | cag | tct | cca | tcc | tcc | ctg | tct | gca | tct | gta | gga | gac | aga | gtc |
| AJL02 AA | D | I | Q | M | T | Q | S | P | S | S | L | S | A | S | V | G | D | R | V |
| AJL02 Nuc | gac | atc | cag | atg | acc | cag | tct | cca | tcc | tcc | ctg | tct | gca | tct | gta | gga | gac | aga | gtc |

| | 1-39 Codon | | | | | | | | | | | | | | | | | | |
|---|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 34 | 35 | 36 | 37 | 38 |
| | 1-39 Kabat | | | | | | | | | | | | | | | | | | |
| | 20 | 21 | 22 | 23 | 24 | 25 | 26 | 27 | 28 | 29 | | | | | | | 30 | 31 | 32 |
| Region | | | | FR1 | | | | | | | | | CDR1 | | | | | | |
| Germ. AA | T | I | T | C | R | A | S | Q | S | I | | | | | | | S | S | Y |
| Germ. Nuc | acc | atc | act | tgc | cgg | gca | agt | cag | agc | att | | | | | | | agc | agc | tct |
| AJL02 AA | T | I | T | C | R | A | S | Q | G | I | | | | | | | S | S | S |
| AJL02 Nuc | acc | atc | act | tgc | cgg | gca | agt | cag | ggc | att | | | | | | | agc | agc | tct |

| | 1-39 Codon | | | | | | | | | | | | | | | | | | |
|---|---|---|---|---|---|---|---|---|---|---|---|---|---|---|---|---|---|---|---|
| | 39 | 40 | 41 | 42 | 43 | 44 | 45 | 46 | 47 | 48 | 49 | 50 | 51 | 52 | 53 | 54 | 55 | 56 | 57 |
| | 1-39 Kabat | | | | | | | | | | | | | | | | | | |
| | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | CDR2 | |
| Germ. AA | L | N | W | Y | Q | Q | K | P | G | K | A | P | K | L | L | I | Y | A | A |
| Germ. Nuc | gta | aat | tgg | ttt | cag | cag | aaa | cca | ggg | aaa | gcc | cct | aag | ctc | ctg | atc | tat | gct | gca |
| AJL02 AA | V | N | W | F | Q | Q | K | P | G | K | A | P | E | L | L | I | Y | A | A |
| AJL02 Nuc | gta | aat | tgg | ttt | cag | cag | aaa | cca | ggg | aaa | gcc | cct | gaa | ctc | ctg | atc | tat | gct | gca |

| | 1-39 Codon | | | | | | | | | | | | | | | | | | |
|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 |
| | 1-39 Kabat | | | | | | | | | | | | | | | | | | |
| | | | | | | | | 52 | 53 | 54 | 55 | 56 | 57 | 58 | 59 | | 60 | 61 | 62 |
| Region | | | CDR2 | | | | | | | | | | | FR3 | | | | | |
| Germ. AA | | | | | | | | S | S | L | Q | S | G | V | P | | S | R | F |
| Germ. Nuc | | | | | | | | tcc | agt | ttg | caa | agt | ggg | gtc | cca | | tca | agg | ttc |
| AJL02 AA | | | | | | | | S | T | L | Q | S | G | V | P | | S | R | F |
| AJL02 Nuc | | | | | | | | tcc | act | ttg | caa | agt | ggg | gtc | cca | | tca | aga | ttc |

| | 1-39 Codon | | | | | | | | | | | | | | | | | | |
|---|---|---|---|---|---|---|---|---|---|---|---|---|---|---|---|---|---|---|---|
| | 77 | 78 | 79 | 80 | 81 | 82 | 83 | 84 | 85 | 86 | 87 | 88 | 89 | 90 | 91 | 92 | 93 | 94 | 95 |
| | 1-39 Kabat | | | | | | | | | | | | | | | | | | |
| | 63 | 64 | 65 | 66 | | | 67 | 68 | 69 | 70 | 71 | 72 | 73 | 74 | 75 | 76 | 77 | 78 | 79 |
| Region | | | | | | | | | FR3 | | | | | | | | | | |
| Germ. AA | S | G | S | G | | | S | G | T | D | F | T | L | T | I | S | S | L | Q |
| Germ. Nuc | agt | ggc | agt | gga | | | tct | ggg | aca | gat | ttc | act | ctc | acc | atc | agc | agt | ctg | caa |
| AJL02 AA | S | G | S | G | | | S | G | T | D | F | T | L | T | V | S | S | L | Q |
| AJL02 Nuc | agt | ggc | agt | gga | | | tct | ggg | aca | gat | ttc | act | ctc | acc | gtc | agc | agt | ctg | caa |

| | 1-39 Codon | | | | | | | | | | | | | | | |
|---|---|---|---|---|---|---|---|---|---|---|---|---|---|---|---|---|
| | 96 | 97 | 98 | 99 | 100 | 101 | 102 | 103 | 104 | 105 | 106 | 107 | 108 | 109 | 110 | 111 |
| | 1-39 Kabat | | | | | | | | | | | | | | | |
| | 80 | 81 | 82 | 83 | 84 | 85 | 86 | 87 | 88 | 89 | 90 | 91 | 92 | | | |
| Region | | | | FR3 | | | | | | | | | CDR3 | | | |
| Germ. AA | P | E | D | F | A | T | Y | Y | C | Q | Q | S | Y | S | T | P |
| Germ. Nuc | cct | gaa | gat | ttt | gca | act | tac | tac | tgt | caa | cag | agt | tac | agt | acc | cct |

TABLE 2-continued

Light Chain Sequences of AGS Enriched CSF Antibodies

| | | | | | | | | | | | | | | | | | | |
|---|---|---|---|---|---|---|---|---|---|---|---|---|---|---|---|---|---|---|
| AJL02 AA | P | E | D | F | A | T | Y | Y | C | Q | Q | S | Y | S | P | P | R | T |
| AJL02 Nuc | cct | gaa | gat | ttt | gca | act | tac | tac | tgt | cag | cag | agt | tac | agt | ccc | cct | cga | act |

(SEQ ID NOS: 41-44, top to bottom)

| | 2-28 Codon | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| | 2-28 Kabat | | | | | | | | | | | | | | | | | | |
| Region | 1 | 2 | 3 | 4 | 5 | 6 | 7 | 8 | 9 | 10 | 11 | 12 | 13 | 14 | 15 | 16 | 17 | 18 | 19 |
| | | | | | | | | | | FR1 | | | | | | | | | |

| | | | | | | | | | | | | | | | | | | | |
|---|---|---|---|---|---|---|---|---|---|---|---|---|---|---|---|---|---|---|---|
| Germ. AA | D | I | V | M | T | Q | S | P | L | S | L | P | V | T | P | G | E | P | A |
| Germ. Nuc | gat | att | gtg | atg | act | cag | tct | cca | ctc | tcc | ctg | ccc | gtc | acc | cct | gga | gag | ccg | gcc |
| AJL10 AA | D | I | V | M | T | Q | S | P | L | S | L | P | V | T | P | G | E | P | A |
| AJL10 Nuc | gat | att | gtg | atg | act | cag | tct | cca | ctc | tcc | ctg | ccc | gtc | acc | cct | gga | gag | ccg | gcc |
| WR12 AA | D | I | V | M | T | Q | S | P | L | S | L | P | V | T | P | G | E | P | A |
| WR12 Nuc | gat | att | gtg | atg | act | cag | tct | cca | ctc | tcc | ctg | ccc | gtc | acc | cct | gga | gag | ccg | gcc |
| WR13 AA | D | I | V | M | T | Q | S | P | L | S | L | P | V | T | P | G | E | P | A |
| WR13 Nuc | gat | att | gtg | atg | act | cag | tct | cca | ctc | tcc | ctg | ccc | gtc | acc | cct | gga | gag | ccg | Gcc |

| | 2-28 Codon | | | | | | | | | | | | | | | | | | |
|---|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 34 | 35 | 36 | 37 | 38 |
| | 2-28 Kabat | | | | | | | | | | | | | | | | | | |
| Region | 20 | 21 | 22 | 23 | 24 | 25 | 26 | 27 | 27a | 27b | 27c | 27d | 27e | 28 | 29 | 30 | 31 | 32 | |
| | | | | FR1 | | | | | | | | CDR1 | | | | | | | |

| | | | | | | | | | | | | | | | | | | | |
|---|---|---|---|---|---|---|---|---|---|---|---|---|---|---|---|---|---|---|---|
| Germ. AA | S | I | S | C | R | S | S | Q | S | L | L | H | S | | N | G | Y | N | Y |
| Germ. Nuc | tcc | atc | tcc | tgc | agg | tct | agt | cag | agc | ctc | ctg | cat | agt | | aat | gga | tac | aac | tat |
| AJL10 AA | S | I | S | C | R | S | T | Q | S | L | L | H | S | | N | E | Y | I | Y |
| AJL10 Nuc | tcc | atc | tcc | tgc | agg | tct | act | cag | agc | ctc | cta | cac | agt | | aat | gaa | tac | att | tat |
| WR12 AA | S | I | S | C | R | S | S | Q | S | L | L | H | S | | N | G | Y | N | Y |
| WR12 Nuc | tcc | atc | tcc | tgc | agg | tct | agt | cag | agc | ctc | ctc | cat | agt | | aat | gga | tac | aac | tat |
| WR13 AA | S | I | S | C | R | S | S | Q | S | L | L | H | S | | N | G | Y | N | Y |
| WR13 Nuc | tcc | atc | tcc | tgc | agg | tct | agt | cag | agc | ctc | ctc | cat | agt | | aat | gga | tac | aac | tat |

| | 2-28 Codon | | | | | | | | | | | | | | | | | | |
|---|---|---|---|---|---|---|---|---|---|---|---|---|---|---|---|---|---|---|---|
| | 39 | 40 | 41 | 42 | 43 | 44 | 45 | 46 | 47 | 48 | 49 | 50 | 51 | 52 | 53 | 54 | 55 | 56 | 57 |
| | 2-28 Kabat | | | | | | | | | | | | | | | | | | |
| Region | 33 | 34 | 35 | 36 | 37 | 38 | 39 | 40 | 41 | 42 | 43 | 44 | 45 | 46 | 47 | 48 | 49 | 50 | 51 |
| | | | | | | | FR2 | | | | | | | | | | | CDR2 | |

| | | | | | | | | | | | | | | | | | | | |
|---|---|---|---|---|---|---|---|---|---|---|---|---|---|---|---|---|---|---|---|
| Germ. AA | L | D | W | Y | L | Q | K | P | G | Q | S | P | Q | L | L | I | Y | L | G |
| Germ. Nuc | ttg | gat | tgg | tac | ctg | cag | aag | cca | ggg | caa | tct | cca | caa | ctc | ctg | atc | tat | ttg | Ggt |
| AJL10 AA | L | D | W | Y | V | Q | K | P | G | Q | S | P | Q | L | L | I | F | L | A |
| AJL10 Nuc | ttg | gat | tgg | tac | gtg | cag | aag | cca | ggg | cag | tct | cca | caa | ctc | ctg | atc | ttt | ttg | gct |
| WR12 AA | L | S | W | Y | L | Q | K | P | G | Q | S | P | Q | L | L | I | F | S | S |
| WR12 Nuc | ttg | agt | tgg | tac | ctg | cag | aag | cca | ggg | cag | tct | cca | caa | ctc | ctg | atc | ttt | tcg | agt |
| WR13 AA | L | S | W | Y | L | Q | K | P | G | Q | S | P | Q | L | L | I | F | S | S |
| WR13 Nuc | ttg | agt | tgg | tac | ctg | cag | aag | cca | ggg | cag | tct | cca | caa | ctc | ctg | atc | ttt | tcg | agt |

| | 2-28 Codon | | | | | | | | | | | | | | | | | | |
|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 |
| | 2-28 Kabat | | | | | | | | | | | | | | | | | | |
| Region | | | | | | | | 52 | 53 | 54 | 55 | 56 | 57 | 58 | 59 | | 60 | 61 | 62 |
| | | | | CDR2 | | | | | | | | | | FR3 | | | | | |

| | | | | | | | | | | | | | | | | | | | |
|---|---|---|---|---|---|---|---|---|---|---|---|---|---|---|---|---|---|---|---|
| Germ. AA | | | | | | | | S | N | R | A | S | G | V | P | | D | R | F |
| Germ. Nuc | | | | | | | | tct | aat | cgg | gcc | tcc | ggg | gtc | cct | | gac | agg | ttc |
| AJL10 AA | | | | | | | | S | N | R | A | S | G | V | P | | D | R | F |
| AJL10 Nuc | | | | | | | | tct | aat | cgg | gcc | tcc | ggg | gtc | cct | | gac | agg | ttc |
| WR12 AA | | | | | | | | S | I | R | A | S | G | V | P | | D | R | F |
| WR12 Nuc | | | | | | | | tct | att | cgg | gcc | tcc | ggg | gtc | cct | | gac | agg | ttc |
| WR13 AA | | | | | | | | S | I | R | A | S | G | V | P | | D | R | F |
| WR13 Nuc | | | | | | | | tct | att | cgg | gcc | tcc | ggg | gtc | cct | | gac | agg | ttc |

TABLE 2-continued

Light Chain Sequences of AGS Enriched CSF Antibodies 2-28 Codon

| | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|
| | | | | | | | | | 2-28 Kabat | | | | | | | | | | |
| | 63 | 64 | 65 | 66 | | | 67 | 68 | 69 | 70 | 71 | 72 | 73 | 74 | 75 | 76 | 77 | 78 | 79 |
| Region | | | | | | | | | FR3 | | | | | | | | | | |
| Germ. AA | S | G | S | G | | | S | G | T | D | F | T | L | K | I | S | R | V | E |
| Germ. Nuc | agt | ggc | agt | gga | | | tca | ggc | aca | gat | ttt | aca | ctg | aaa | atc | agc | aga | gtg | gag |
| AJL10 AA | S | G | S | A | | | S | G | T | D | F | T | L | K | I | S | R | V | E |
| AJL10 Nuc | agt | ggc | agt | gca | | | tca | ggc | aca | gat | ttt | aca | ctg | aaa | atc | agc | aga | gtg | gag |
| WR12 AA | S | G | S | G | | | S | G | T | D | F | T | L | T | I | N | R | V | E |
| WR12 Nuc | agt | ggc | agt | gga | | | tca | ggc | aca | gat | ttt | aca | ctg | aca | atc | aac | aga | gtg | gag |
| WR13 AA | S | G | S | G | | | S | G | T | D | F | T | L | T | I | N | R | V | E |
| WR13 Nuc | agt | ggc | agt | gga | | | tca | ggc | aca | gat | ttt | aca | ctg | aca | atc | aac | aga | gtg | gag |

2-28 Codon

| | 96 | 97 | 98 | 99 | 100 | 101 | 102 | 103 | 104 | 105 | 106 | 107 | 108 | 109 | 110 | 111 | | |
|---|---|---|---|---|---|---|---|---|---|---|---|---|---|---|---|---|---|---|
| | | | | | | | | | 2-28 Kabat | | | | | | | | | |
| | 80 | 81 | 82 | 83 | 84 | 85 | 86 | 87 | 88 | 89 | 90 | 91 | 92 | | | | | |
| Region | | | FR3 | | | | | | | | | | CDR3 | | | | | |
| Germ. AA | A | E | D | V | G | V | Y | Y | C | M | Q | A | L | Q | T | P | | |
| Germ. Nuc | gct | gag | gat | gtt | ggg | gtt | tat | tac | tgc | atg | caa | gct | cta | caa | act | cct | | |
| AJL10 AA | A | E | D | V | G | V | Y | Y | C | M | Q | A | L | E | A | P | W | T |
| AJL10 Nuc | gct | gag | gat | gtt | ggg | gtt | tat | tac | tgc | atg | caa | gct | cta | gaa | gct | ccg | tgg | acg |
| WR12 AA | A | E | D | V | G | V | Y | Y | C | M | Q | A | L | Q | T | P | L | T |
| WR12 Nuc | gct | gag | gat | gtt | gga | gtt | tat | tac | tgc | atg | cag | gct | cta | caa | act | ccg | ctc | act |
| WR13 AA | A | E | D | V | G | V | Y | Y | C | M | Q | A | L | Q | T | P | L | T |
| WR13 Nuc | gct | gag | gat | gtt | gga | gtt | tat | tac | tgc | atg | cag | gct | cta | caa | act | ccg | ctc | act |

(SEQ ID NOS: 45-52, top to bottom)

2D-29 Codon

| | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| | | | | | | | | | 2D-29 Kabat | | | | | | | | | | |
| | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | FR1 | | | | | | | | | | |
| Germ. AA | D | I | V | M | T | Q | T | P | L | S | L | S | V | T | P | G | Q | P | A |
| Germ. Nuc | gat | att | gtg | atg | acc | cag | act | cca | ctc | tct | ctg | tcc | gtc | acc | cct | gga | cag | ccg | gcc |
| AJL15 AA | D | I | V | M | T | Q | T | P | L | S | L | S | V | T | P | G | Q | P | A |
| AJL15 Nuc | gat | att | gtg | atg | acc | cag | act | cca | ctc | tct | ttg | tcc | gtc | acc | cct | gga | cag | ccg | gcc |

2D-29 Codon

| | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|
| | | | | | | | | | 2D-29 Kabat | | | | | | | | | | |
| | 20 | 21 | 22 | 23 | 24 | 25 | 26 | 27 | 27a | 27b | 27c | 27d | 27e | 28 | 29 | 30 | 31 | 32 | |
| Region | | | FR1 | | | | | | | | | CDR1 | | | | | | | |
| Germ. AA | S | I | S | C | K | S | S | Q | S | L | L | H | S | D | G | K | T | Y | |
| Germ. Nuc | tcc | atc | tcc | tgc | aag | tct | agt | cag | agc | ctc | ctg | cat | agt | gat | gga | aag | acc | tat | |
| AJL15 AA | S | I | S | C | K | S | S | Q | S | L | L | D | S | D | G | K | T | H | |
| AJL15 Nuc | tcc | atc | tcc | tgc | aaa | tct | agt | cag | agc | ctc | ctg | gat | agt | gat | gga | aag | acc | cat | |

2D-29 Codon

| | 39 | 40 | 41 | 42 | 43 | 44 | 45 | 46 | 47 | 48 | 49 | 50 | 51 | 52 | 53 | 54 | 55 | 56 | 57 |
|---|---|---|---|---|---|---|---|---|---|---|---|---|---|---|---|---|---|---|---|
| | | | | | | | | | 2D-29 Kabat | | | | | | | | | | |
| | 33 | 34 | 35 | 36 | 37 | 38 | 39 | 40 | 41 | 42 | 43 | 44 | 45 | 46 | 47 | 48 | 49 | 50 | 51 |
| Region | | | | | | | | | FR2 | | | | | | | | | | CDR2 |
| Germ. AA | L | Y | W | Y | L | Q | K | P | G | Q | S | P | Q | L | L | I | Y | E | V |
| Germ. Nuc | ttg | tat | tgg | tac | ctg | cag | aag | cca | ggc | cag | tct | cca | cag | ctc | ctg | atc | tat | gaa | gtt |
| AJL15 AA | L | Y | W | Y | L | Q | K | P | G | Q | S | P | Q | S | L | I | Y | E | V |
| AJL15 Nuc | ttg | tac | tgg | tac | ctg | cag | aag | cca | ggc | cag | tct | cca | cag | tcc | ctg | atc | tat | gaa | gtt |

TABLE 2-continued

Light Chain Sequences of AGS Enriched CSF Antibodies

| | 2D-29 Codon | | | | | | | | | | | | | | | | | |
|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 |
| | 2D-29 Kabat | | | | | | | | | | | | | | | | | |
| | | | | | | | 52 | 53 | 54 | 55 | 56 | 57 | 58 | 59 | | 60 | 61 | 62 |
| Region | CDR2 | | | | | | | | | | | | FR3 | | | | | |
| Germ. AA | | | | | | | | S | N | R | F | S | G | V | P | | D | R | F |
| Germ. Nuc | | | | | | | | tcc | aac | cgg | ttc | tct | gga | gtg | cca | | gat | agg | ttc |
| AJL15 AA | | | | | | | | S | K | R | F | S | G | V | P | | D | R | F |
| AJL15 Nuc | | | | | | | | tct | aaa | cgg | ttc | tct | gga | gtg | cca | | gat | agg | ttc |

| | 2D-29 Codon | | | | | | | | | | | | | | | | | |
|---|---|---|---|---|---|---|---|---|---|---|---|---|---|---|---|---|---|---|
| | 77 | 78 | 79 | 80 | 81 | 82 | 83 | 84 | 85 | 86 | 87 | 88 | 89 | 90 | 91 | 92 | 93 | 94 | 95 |
| | 2D-29 Kabat | | | | | | | | | | | | | | | | | |
| | 63 | 64 | 65 | 66 | | | 67 | 68 | 69 | 70 | 71 | 72 | 73 | 74 | 75 | 76 | 77 | 78 | 79 |
| Region | | | | | | | | | FR3 | | | | | | | | | | |
| Germ. AA | S | G | S | G | | | S | G | T | D | F | T | L | K | I | S | R | V | E |
| Germ. Nuc | agt | ggc | agc | ggg | | | tca | ggg | aca | gat | ttc | aca | ctg | aaa | atc | agc | cgg | gtg | gag |
| AJL15 AA | T | G | S | G | | | S | G | T | D | F | T | L | K | I | S | R | V | E |
| AJL15 Nuc | act | ggc | agc | ggg | | | tca | ggg | aca | gat | ttc | aca | ctg | aaa | atc | agc | cgg | gtg | gag |

| | 2D-29 Codon | | | | | | | | | | | | | | | |
|---|---|---|---|---|---|---|---|---|---|---|---|---|---|---|---|---|
| | 96 | 97 | 98 | 99 | 100 | 101 | 102 | 103 | 104 | 105 | 106 | 107 | 108 | 109 | 110 | 111 |
| | 2D-29 Kabat | | | | | | | | | | | | | | | |
| | 80 | 81 | 82 | 83 | 84 | 85 | 86 | 87 | 88 | 89 | 90 | 91 | 92 | | | |
| Region | | | | | FR3 | | | | | | | | CDR3 | | | |
| Germ. AA | A | E | D | V | G | V | Y | Y | C | M | Q | S | I | Q | L | P |
| Germ. Nuc | gct | gag | gat | gtt | ggg | gtt | tat | tac | tgc | atg | caa | agt | ata | cag | ctt | cct |
| AJL15 AA | A | E | D | V | G | L | Y | Y | C | M | Q | S | A | Q | L | P | Y | T |
| AJL15 Nuc | gct | gag | gat | gtt | ggg | ctt | tat | tac | tgc | atg | caa | agt | gca | cag | ctt | ccg | tac | act |

(SEQ ID NOS: 53-56, top to bottom)

| | 3-20 Codon | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| | 3-20 Kabat | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 |
| Region | | | | | | | | | FR1 | | | | | | | | | |
| Germ. AA | E | I | V | L | T | Q | S | P | G | T | L | S | L | S | P | G | E | R | A |
| Germ. Nuc | gaa | att | gtg | ttg | acg | cag | tct | cca | ggc | acc | ctg | tct | ttg | tct | cca | ggg | gaa | aga | Gcc |
| AJL01 AA | E | I | V | L | T | Q | S | P | G | T | L | S | L | S | P | G | E | R | A |
| AJL01 Nuc | gaa | att | gtg | ttg | acg | cag | tct | cca | ggc | acc | ctg | tct | ttg | tct | cca | ggg | gaa | aga | Gcc |
| AJL19 AA | E | I | V | L | T | Q | S | P | G | T | L | S | L | S | P | G | E | R | A |
| AJL19 Nuc | gaa | att | gtg | ttg | acg | cag | tct | cca | ggc | acc | ctg | tct | ttg | tct | cca | ggg | gaa | aga | Gcc |
| WR10 AA | E | I | V | L | T | Q | S | P | G | T | L | S | L | S | P | G | E | R | A |
| WR10 Nuc | gaa | att | gtg | ttg | acg | cag | tct | cca | ggc | acc | ctg | tct | ttg | tct | cca | ggg | gaa | aga | Gcc |

| | 3-20 Codon | | | | | | | | | | | | | | | |
|---|---|---|---|---|---|---|---|---|---|---|---|---|---|---|---|---|
| | 20 | 21 | 22 | 23 | 24 | 25 | 26 | 27 | 28 | 29 | 30 | | | | 36 | 37 | 38 |
| | 3-20 Kabat | | | | | | | | | | | | | | | |
| | 20 | 21 | 22 | 23 | 24 | 25 | 26 | 27 | 27a | 28 | 29 | 31 | 32 | 33 | 34 | 35 | 30 | 31 | 32 |
| Region | | | | FR1 | | | | | | | | | CDR1 | | | | | | |
| Germ. AA | T | L | S | C | R | A | S | Q | S | V | S | | | | | | S | S | Y |
| Germ. Nuc | acc | ctc | tcc | tgc | agg | gcc | agt | cag | agt | gtt | agc | | | | | | agc | agc | Tac |
| AJL01 AA | T | L | S | C | R | A | S | Q | S | L | I | | | | | | G | S | F |
| AJL01 Nuc | acc | ctc | tcc | tgc | agg | gcc | agt | cag | agt | ctt | atc | | | | | | ggc | agc | Ttc |
| AJL19 AA | T | L | S | C | R | A | S | Q | S | V | S | | | | | | S | D | S |
| AJL19 Nuc | acc | ctc | tcc | tgc | agg | gcc | agt | cag | agt | gtt | agc | | | | | | agc | gac | tcc |
| WR10 AA | T | L | S | C | R | A | S | Q | S | L | I | | | | | | G | S | F |
| WR10 Nuc | acc | ctc | tcc | tgc | agg | gcc | agt | cag | agt | ctt | atc | | | | | | ggc | agc | ttc |

TABLE 2-continued

Light Chain Sequences of AGS Enriched CSF Antibodies

| | 3-20 Codon | | | | | | | | | | | | | | | | | | |
|---|---|---|---|---|---|---|---|---|---|---|---|---|---|---|---|---|---|---|---|
| | 39 | 40 | 41 | 42 | 43 | 44 | 45 | 46 | 47 | 48 | 49 | 50 | 51 | 52 | 53 | 54 | 55 | 56 | 57 |
| | 3-20 Kabat | | | | | | | | | | | | | | | | | | |
| | 33 | 34 | 35 | 36 | 37 | 38 | 39 | 40 | 41 | 42 | 43 | 44 | 45 | 46 | 47 | 48 | 49 | 50 | 51 |
| Region | | | | | | | FR2 | | | | | | | | | | | | CDR2 |
| Germ. AA | L | A | W | Y | Q | Q | K | P | G | Q | A | P | R | L | L | I | Y | G | A |
| Germ. Nuc | tta | gcc | tgg | tac | cag | cag | aaa | cct | ggc | cag | gct | ccc | agg | ctc | ctc | atc | tat | ggt | gca |
| AJL01 AA | L | A | W | Y | Q | Q | K | P | G | Q | A | P | R | L | L | I | Y | H | T |
| AJL01 Nuc | tta | gcc | tgg | tac | cag | cag | aaa | cct | ggc | cag | gct | ccc | agg | ctc | ctc | atc | tat | cat | aca |
| AJL19 AA | L | A | W | Y | Q | Q | K | P | G | Q | T | P | R | L | L | I | Y | H | T |
| AJL19 Nuc | tta | gcc | tgg | tac | cag | cag | aaa | cct | ggc | cag | act | ccc | agg | ctc | ctc | att | tat | cat | aca |
| WR10 AA | L | A | W | Y | Q | Q | K | P | G | Q | A | P | R | L | L | I | Y | H | T |
| WR10 Nuc | tta | gcc | tgg | tac | cag | cag | aaa | cct | ggc | cag | gct | ccc | agg | ctc | ctc | atc | tat | cat | aca |

| | 3-20 Codon | | | | | | | | | | | | | | | | | | |
|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 |
| | 3-20 Kabat | | | | | | | | | | | | | | | | | | |
| | | | | | | | | 52 | 53 | 54 | 55 | 56 | 57 | 58 | 59 | | 60 | 61 | 62 |
| Region | | | CDR2 | | | | | | | | | | | | FR3 | | | | |
| Germ. AA | | | | | | | | S | S | R | A | T | G | I | P | | D | R | F |
| Germ. Nuc | | | | | | | | tcc | agc | agg | gcc | act | ggc | atc | cca | | gac | agg | ttc |
| AJL01 AA | | | | | | | | S | N | R | A | S | G | I | P | | D | R | F |
| AJL01 Nuc | | | | | | | | tcc | aac | agg | gcc | tct | ggc | atc | cca | | gac | agg | ttc |
| AJL19 AA | | | | | | | | S | T | R | A | A | G | I | P | | D | R | F |
| AJL19 Nuc | | | | | | | | tcc | acc | agg | gcc | gct | ggc | atc | cca | | gac | agg | ttc |
| WR10 AA | | | | | | | | S | N | R | A | S | G | I | P | | D | R | F |
| WR10 Nuc | | | | | | | | tcc | aac | agg | gcc | tct | ggc | atc | cca | | gac | agg | ttc |

| | 3-20 Codon | | | | | | | | | | | | | | | | | | |
|---|---|---|---|---|---|---|---|---|---|---|---|---|---|---|---|---|---|---|---|
| | 77 | 78 | 79 | 80 | 81 | 82 | 83 | 84 | 85 | 86 | 87 | 88 | 89 | 90 | 91 | 92 | 93 | 94 | 95 |
| | 3-20 Kabat | | | | | | | | | | | | | | | | | | |
| | 63 | 64 | 65 | 66 | | | 67 | 68 | 69 | 70 | 71 | 72 | 73 | 74 | 75 | 76 | 77 | 78 | 79 |
| Region | | | | | | | | | FR3 | | | | | | | | | | |
| Germ. AA | S | G | S | G | | | S | G | T | D | F | T | L | T | I | S | R | L | E |
| Germ. Nuc | agt | ggc | agt | ggg | | | tct | ggg | aca | gac | ttc | act | ctc | acc | atc | agc | aga | ctg | gag |
| AJL01 AA | S | G | G | G | | | F | G | T | D | F | T | L | T | I | S | R | L | E |
| AJL01 Nuc | agt | ggc | ggt | ggg | | | ttt | ggg | aca | gac | ttc | act | ctc | acc | atc | agc | aga | ctg | gag |
| AJL19 AA | S | G | T | G | | | S | G | T | D | F | T | L | T | I | A | R | L | E |
| AJL19 Nuc | agt | ggc | act | ggg | | | tct | ggg | aca | gac | ttc | act | ctc | acc | atc | gcc | aga | ctg | gag |
| WR10 AA | S | G | G | G | | | F | G | T | D | F | T | L | T | I | S | R | L | E |
| WR10 Nuc | agt | ggc | ggt | ggg | | | ttt | ggg | aca | gac | ttc | act | ctc | acc | atc | agc | aga | ctg | gag |

| | 3-20 Codon | | | | | | | | | | | | | | | |
|---|---|---|---|---|---|---|---|---|---|---|---|---|---|---|---|---|
| | 96 | 97 | 98 | 99 | 100 | 101 | 102 | 103 | 104 | 105 | 106 | 107 | 108 | 109 | 110 | 111 |
| | 3-20 Kabat | | | | | | | | | | | | | | | |
| | 80 | 81 | 82 | 83 | 84 | 85 | 86 | 87 | 88 | 89 | 90 | 91 | 92 | | | |
| Region | | | | | FR3 | | | | | | | | | CDR3 | | |
| Germ. AA | P | E | D | F | A | V | Y | Y | C | Q | Q | Y | G | S | S | P |
| Germ. Nuc | cct | gaa | gat | ttt | gca | gtg | tat | tac | tgt | cag | cag | tat | ggt | agc | tca | cct |
| AJL01 AA | P | E | D | F | A | V | Y | Y | C | Q | Q | Y | D | S | S | P | I | T |
| AJL01 Nuc | cct | gaa | gat | ttt | gca | gtt | tat | tac | tgt | caa | cag | tat | gat | agc | tca | ccg | atc | acc |
| AJL19 AA | P | E | D | F | A | V | Y | Y | C | Q | H | Y | G | R | S | S | L | F | T |
| AJL19 Nuc | cct | gaa | gat | ttt | gca | gtc | tat | tac | tgt | cag | cac | tat | ggt | cgg | tca | tcc | cta | ttc | acc |
| WR10 AA | P | E | D | F | A | V | Y | Y | C | Q | Q | Y | D | S | S | P | I | T |
| WR10 Nuc | cct | gaa | gat | ttt | gca | gtt | tat | tac | tgt | caa | cag | tat | gat | agc | tca | ccg | atc | acc |

(SEQ ID NOS: 57-64, top to bottom)

TABLE 3

AGS Mutations and Binding Patterns

| | | AGS Codon | | | | | | | | | | | | | | | | | | |
|---|---|---|---|---|---|---|---|---|---|---|---|---|---|---|---|---|---|---|---|---|
| | | 36 (31b) | | | | | | 45 (40) | | | | | | 64 (56) | | | | | | |
| | Gene | 4-30 | 4-31 | 4-34 | 4-39 | 4-4 | 4-59 | 4-30 | 4-31 | 4-34 | 4-39 | 4-4 | 4-59 | 4-30 | 4-31 | 4-34 | 4-39 | 4-4 | 4-59 |
| | AA | D | G | — | S | — | — | P | H | P | P | P | P | S | S | S | S | S | S |
| | Nuc. | gat | ggt | — | agt | — | — | ccc | cac | ccc | ccc | ccc | ccc | agc | agc | agc | agc | agc | agc |
| Dual Binding | AJL02 | — | G | — | — | — | — | — | S | — | — | — | — | — | S | — | — | — | — |
| | | — | ggt | — | — | — | — | — | tcc | — | — | — | — | — | agc | — | — | — | — |
| | AJL07 | — | — | — | — | — | — | — | — | — | — | P | — | — | — | — | — | — | N |
| | | — | — | — | — | — | — | — | — | — | — | ccc | — | — | — | — | — | — | aat |
| | AJL19 | — | — | — | — | — | — | P | — | — | — | — | — | — | — | D | — | — | — |
| | | — | — | — | — | — | — | ccc | — | — | — | — | — | — | — | gat | — | — | — |
| | WR10 | — | — | — | — | — | — | — | — | S | — | — | — | — | — | — | — | G | — |
| | | — | — | — | — | — | — | — | — | tcc | — | — | — | — | — | — | — | ggc | — |
| Astrocyte | AJL01 | — | — | — | — | — | — | P | — | — | — | — | — | R | — | — | — | — | — |
| | | — | — | — | — | — | — | ccc | — | — | — | — | — | aga | — | — | — | — | — |
| | WR12 | D | — | — | — | — | — | P | — | — | — | — | — | T | — | — | — | — | — |
| | | gat | — | — | — | — | — | ccc | — | — | — | — | — | acc | — | — | — | — | — |
| | WR13 | D | — | — | — | — | — | P | — | — | — | — | — | T | — | — | — | — | — |
| | | gat | — | — | — | — | — | ccc | — | — | — | — | — | acc | — | — | — | — | — |
| Neuron | AJL03 | — | — | — | R | — | — | — | — | P | — | — | — | — | — | — | S | — | — |
| | | — | — | — | cgt | — | — | — | — | ccc | — | — | — | — | — | — | agc | — | — |
| | AJL10 | — | — | — | — | — | — | — | — | S | — | — | — | — | — | — | — | T | — |
| | | — | — | — | — | — | — | — | — | tcc | — | — | — | — | — | — | — | act | — |
| | AJL15 | — | — | — | N | — | — | S | — | — | — | — | — | — | — | — | S | — | — |
| | | — | — | — | aat | — | — | tcc | — | — | — | — | — | — | — | — | agc | — | — |

| | | AGS Codon | | | | | | | | | | | | | | | | | | |
|---|---|---|---|---|---|---|---|---|---|---|---|---|---|---|---|---|---|---|---|---|
| | | 65 (57) | | | | | | 90 (81) | | | | | | 101 (89) | | | | | | |
| | Gene | 4-30 | 4-31 | 4-34 | 4-39 | 4-4 | 4-59 | 4-30 | 4-31 | 4-34 | 4-39 | 4-4 | 4-59 | 4-30 | 4-31 | 4-34 | 4-39 | 4-4 | 4-59 |
| | AA | T | T | T | T | T | T | K | K | K | K | K | K | V | V | V | V | V | V |
| | Nuc. | acc | acc | acc | acc | acc | acc | aag | aag | aag | aag | aag | aag | gtg | gtg | gtg | gtg | gtg | gtg |
| Dual Binding | AJL02 | — | T | — | — | — | — | — | R | — | — | — | — | — | V | — | — | — | — |
| | | — | acc | — | — | — | — | — | agg | — | — | — | — | — | gtc | — | — | — | — |
| | AJL07 | — | — | — | — | I | — | — | — | — | — | N | — | — | — | — | — | — | V |
| | | — | — | — | — | att | — | — | — | — | — | aac | — | — | — | — | — | — | gtg |
| | AJL19 | — | — | A | — | — | — | — | — | K | — | — | — | — | — | L | — | — | — |
| | | — | — | gcc | — | — | — | — | — | aag | — | — | — | — | — | tta | — | — | — |
| | WR10 | — | — | — | T | — | — | — | — | — | K | — | — | — | — | — | V | — | — |
| | | — | — | — | acc | — | — | — | — | — | aag | — | — | — | — | — | gtg | — | — |
| Astrocyte | AJL01 | — | — | A | — | — | — | — | — | N | — | — | — | — | — | V | — | — | — |
| | | — | — | gcc | — | — | — | — | — | aac | — | — | — | — | — | gtc | — | — | — |
| | WR12 | T | — | — | — | — | — | R | — | — | — | — | — | V | — | — | — | — | — |
| | | acc | — | — | — | — | — | agg | — | — | — | — | — | gtc | — | — | — | — | — |
| | WR13 | T | — | — | — | — | — | R | — | — | — | — | — | V | — | — | — | — | — |
| | | acc | — | — | — | — | — | agg | — | — | — | — | — | gtc | — | — | — | — | — |
| Neuron | AJL03 | — | — | — | T | — | — | — | — | N | — | — | — | — | — | — | V | — | — |
| | | — | — | — | act | — | — | — | — | aac | — | — | — | — | — | — | gtg | — | — |
| | AJL10 | — | — | — | T | — | — | — | — | — | R | — | — | — | — | — | — | I | — |
| | | — | — | — | act | — | — | — | — | — | agg | — | — | — | — | — | — | ata | — |
| | AJL15 | — | — | D | — | — | — | — | — | K | — | — | — | — | — | V | — | — | — |
| | | — | — | gac | — | — | — | — | — | agg | — | — | — | — | — | gtg | — | — | — |

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,683,202
U.S. Pat. No. 4,684,611
U.S. Pat. No. 4,816,567
U.S. Pat. No. 4,867,973
U.S. Pat. No. 4,879,236
U.S. Pat. No. 4,938,948
U.S. Pat. No. 4,952,500
U.S. Pat. No. 5,021,236
U.S. Pat. No. 5,141,648
U.S. Pat. No. 5,196,066
U.S. Pat. No. 5,217,879
U.S. Pat. No. 5,302,523
U.S. Pat. No. 5,322,783

U.S. Pat. No. 5,384,253
U.S. Pat. No. 5,464,765
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,563,250
U.S. Pat. No. 5,565,332
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215
U.S. Pat. No. 5,824,544
U.S. Pat. No. 5,830,725
U.S. Pat. No. 5,849,304
U.S. Pat. No. 5,851,826
U.S. Pat. No. 5,856,456
U.S. Pat. No. 5,858,744
U.S. Pat. No. 5,871,982
U.S. Pat. No. 5,871,983
U.S. Pat. No. 5,871,986
U.S. Pat. No. 5,879,934
U.S. Pat. No. 5,880,270
U.S. Pat. No. 5,888,502
U.S. Pat. No. 5,925,565
U.S. Pat. No. 5,928,906
U.S. Pat. No. 5,932,210
U.S. Pat. No. 5,935,819
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 6,013,516
Abbondanzo et al., *Am. J. Pediatr. Hematol. Oncol.*, 12(4), 480-489, 1990.
Allred et al., *Arch. Surg.*, 125(1), 107-113, 1990.
Almendro et al., *J. Immunol.*, 157(12):5411-5421, 1996.
Amado and Chen, *Science*, 285(5428):674-676, 1999.
Angel et al., *Cell*, 49:729, 1987a.
Angel et al., *Cell*, 49:729, 1987b.
Armentano et al., *Proc. Natl. Acad. Sci. USA*, 87(16):6141-6145, 1990.
Atherton et al., *Biol. of Reproduction*, 32, 155-171, 1985.
Ausubel et al., *Current Protocols in Molecular Biology*, Greene Publishing Associates and Wiley Interscience, N.Y., 1994.
Banerji et al., *Cell*, 27:299, 1981.
Banerji et al., *Cell*, 33(3):729-740, 1983.
Bates, *Mol. Biotechnol.*, 2(2):135-145, 1994.
Batra et al., *Am. J. Respir. Cell Mol. Biol.*, 21(2):238-245, 1999.
Berkhout et al., *Cell*, 59:273-282, 1989.
Bett et al., *J. Virololgy*, 67(10):5911-5921, 1993.
Bhattacharjee et al., *J. Plant Bioch. Biotech.*, 6(2):69-73, 1997.
Bilbao et al., *FASEB J.*, 11(8):624-634, 1997.
Bitsch et al., *Brain*, Jun; 123 (Pt 6):1174-83, 2013.
Blackwell et al., *Arch. Otolaryngol Head Neck Surg.*, 125 (8):856-863, 1999.
Blanar et al., *EMBO J.*, 8:1139, 1989.
Blomer et al., *J. Virol.*, 71(9):6641-6649, 1997.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brown et al., *J. Immunol. Meth.*, 12; 130(1), 111-121, 1990.
Cameron et al., *Journal of Neuroimmunology*, 213:123-30, 2009.
Campo et al., *Nature*, 303:77, 1983.
Capaldi et al., *Biochem. Biophys. Res. Comm.*, 74(2):425-433, 1977.
Caplen et al., *Gene Ther.*, 6(3):454-459, 1999.
Carbonelli et al., *FEMS Microbiol. Lett.*, 177(1):75-82, 1999.
Case et al., *Proc. Natl. Acad. Sci. USA*, 96(6):2988-2993, 1999.
Celander and Haseltine, *J. Virology*, 61:269, 1987.
Celander et al., *J. Virology*, 62:1314, 1988.
Cepok et al., *Brain.*, July; 128(Pt 7):1667-76, 2005.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Chillon et al., *J. Virol.*, 73(3):2537-2540, 1999.
Choi et al., *J. Mol. Biol.*, 262(2):151-167, 1996.
Christou et al., *Proc. Natl. Acad. Sci. USA*, 84(12):3962-3966, 1987.
Clay et al., *J. Immunol.*, 162:1749, 1999.
Cocea, *Biotechniques*, 23(5):814-816, 1997.
Coffey et al., *Science*, 282(5392):1332-1334, 1998.
Cohen et al., *J. Cell. Physiol.*, 5:75, 1987.
Costa et al., *Mol. Cell. Biol.*, 8:81-90, 1988.
Cripe et al., *EMBO J.*, 6:3745, 1987.
Culotta and Hamer, *Mol. Cell. Biol.*, 9:1376-1380, 1989.
D'Halluin et al., *Plant Cell*, 4(12):1495-1505, 1992.
Dandolo et cll., J. Virology, 47:55-64, 1983.
De Jager et al., *Semin. Nucl. Med.* 23(2), 165-179, 1993.
de Vries et al., *Epilepsia.*, November; 53 Suppl 6:45-52, 2012.
DeLuca et al., *J. Virol.*, 56(2):558-570, 1985.
Derby et al., *Hear Res*, 134(1-2):1-8, 1999.
Derfuss et al., *Proc Natl Acad Sci USA.*, May 19; 106(20): 8302-7, 2009.
Deschamps et al., *Science*, 230:1174-1177, 1985.
Dholakia et al., *J. Biol. Chem.*, 264, 20638-20642, 1989.
Doolittle and Ben-Zeev, *Methods Mol. Biol.*, 109, 215-237, 1999.
Dorai et al., *Int. J. Cancer*, 82(6):846-52, 1999.
Duraisamy et al., *Gene*, 373:28-34, 2006.
Edbrooke et al., *Mol. Cell. Biol.*, 9:1908-1916, 1989.
Edlund et al., *Science*, 230:912-916, 1985.
Eikelenboom et al., *Neurology*, January 28; 60(2):219-23, 2003.
Engel and Kohn, *Front Biosci*, 4:e26-33, 1999.
EPO 0273085
Fechheimer et al., *Proc Natl. Acad. Sci. USA*, 84:8463-8467, 1987.
Feldman et al., *Cardiovasc. Res.*, 32(2):194-207, 1996.
Feldman et al., *Semin. Interv. Cardiol.*, 1(3):203-208, 1996.
Feng and Holland, *Nature*, 334:6178, 1988.
Feng et al., *Nat. Biotechnol.*, 15(9):866-870, 1997.
Fisher et al., *Hum. Gene Ther.*, 7(17):2079-2087, 1996.
Fisniku et al., *Ann Neurol.*, September; 64(3):247-54, 2008.
Foecking and Hofstetter, *Gene*, 45(1):101-105, 1986.

Fraley et al., *Proc. Natl. Acad. Sci. USA*, 76:3348-3352, 1979.
Fujita et al., *Cell*, 49:357, 1987.
Fujiwara and Tanaka, *Nippon Geka Gakkai Zasshi*, 99(7): 463-468, 1998.
Garoff and Li, *Curr. Opin. Biotechnol.*, 9(5):464-469, 1998.
Garrido et al., *J. Neurovirol.*, 5(3):280-288, 1999.
Gefter et al., *Somatic Cell Genet.*, 3:231-236, 1977.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gloss et al., *EMBO J.*, 6:3735, 1987.
Gnant et al., *Cancer Res.*, 59(14):3396-403, 1999.
Gnant et al., *J. Natl. Cancer Inst.*, 91(20):1744-1750, 1999.
Godbout et al., *Mol. Cell. Biol.*, 8:1169, 1988.
Goodbourn et al., *Cell*, 45:601, 1986.
Gopal, *Mol. Cell Biol.*, 5:1188-1190, 1985.
Graham and Prevec, *Mol Biotechnol*, 3(3):207-220, 1995.
Graham and Van Der Eb, *Virology*, 52:456-467, 1973.
Greene et al., *Immunology Today*, 10:272, 1989.
Grosschedl and Baltimore, *Cell*, 41:885, 1985.
Gulbis and Galand, *Hum. Pathol.* 24(12), 1271-1285, 1993.
Haecker et al., *Hum. Gene Ther.*, 7(15):1907-1914, 1996.
Han et al., *J. Infect. Dis.*, 179:230-233, 1999.
Harland and Weintraub, *J. Cell Biol.*, 101(3):1094-1099, 1985.
Haslinger and Karin, *Proc. Natl. Acad. Sci. USA*, 82:8572, 1985.
Hauber and Cullen, *J. Virology*, 62:673, 1988.
Hayashi et al., *Neurosci. Lett.*, 267(1):37-40, 1999.
He et al., *Plant Cell Reports*, 14 (2-3):192-196, 1994.
Hen et al., *Nature*, 321:249, 1986.
Hensel et al., *Lymphokine Res.*, 8:347, 1989.
Hermens and Verhaagen, *Prog. Neurobiol.*, 55(4):399-432, 1998.
Herr and Clarke, *Cell*, 45:461, 1986.
Hirochika et al., *J. Virol.*, 61:2599, 1987.
Holbrook et al., *Virology*, 157:211, 1987.
Holzer et al. *Virology*, 253(1):107-114, 1999.
Horlick and Benfield, *Mol. Cell. Biol.*, 9:2396, 1989.
Hou and Lin, *Plant Physiology*, 111:166, 1996.
Howard et al., *Ann. NY Acad. Sci.*, 880:352-365, 1999.
Huang et al., *Cell*, 27:245, 1981.
Huard et al., *Neuromuscul Disord*, 7(5):299-313, 1997.
Hwang et al., *Mol. Cell. Biol.*, 10:585, 1990.
Imagawa et al., *Cell*, 51:251, 1987.
Imai et al., *Nephrologie*, 19(7):397-402, 1998.
Imler et al., *Mol. Cell. Biol.*, 7:2558, 1987.
Inci et al., *Antisense Nucleic Acid Drug Dev.*, 9(4):341-349, 1999.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9(8):3393-3399, 1989.
Johnston et al., *J. Virol.*, 73(6):4991-5000, 1999.
Kadesch and Berg, *Mol. Cell. Biol.*, 6:2593, 1986.
Kaeppler et al., *Plant Cell Rep.*, 8:415-418, 1990.
Kaneda et al., *Science*, 243:375-378, 1989.
Karin et al., *Mol. Cell. Biol.*, 7:606, 1987.
Katinka et al., *Cell*, 20:393, 1980.
Katinka et al., *Nature*, 290:720, 1981.
Kato et al, *J. Biol. Chem.*, 266:3361-3364, 1991.
Kaufman et al., *Arch. Ophthalmol.*, 117(7):925-928, 1999.
Kawamoto et al., *Mol. Cell. Biol.*, 8:267, 1988.
Kay, *Haemophilia*, 4(4):389-392, 1998.
Keegan et al., *Lancet.*, August 13-19; 366(9485):579-82, 2005.
Khatoon et al., *Ann. of Neurology*, 26, 210-219, 1989.
Kiledjian et al., *Mol. Cell. Biol.*, 8:145, 1988.
King et al., *J. Biol. Chem.*, 269, 10210-10218, 1989.
Klamut et al., *Mol. Cell. Biol.*, 10:193, 1990.
Klimatcheva et al., *Front Biosci*, 4:D481-496, 1999.
Koch et al., *Mol. Cell. Biol.*, 9:303, 1989.
Kohler and Milstein, *Eur. J. Immunol.*, 6, 511-519, 1976.
Kohler and Milstein, *Nature*, 256, 495-497, 1975.
Kohut et al., *Am. J. Physiol.*, 275(6Pt1):L1089-1094, 1998.
Kooby et al., *FASEB J*, 13(11):1325-34, 1999.
Kraus et al. *FEBS Lett.*, 428(3):165-170, 1998.
Kriegler and Botchan, *Mol. Cell. Biol.*, 3:325, 1983.
Kriegler et al., *Cell*, 38:483, 1984a.
Kriegler et al., In: *Cancer Cells 2/Oncogenes and Viral Genes*, Van de Woude et al. eds, Cold Spring Harbor, Cold Spring Harbor Laboratory, 1984b.
Krisky et al., *Gene Ther*, 5(11):1517-1530, 1998a.
Krisky et al., *Gene Ther*, 5(12):1593-1603, 1998b.
Kuhl et al., *Cell*, 50:1057, 1987.
Kunz et al., *Nucl. Acids Res.*, 17:1121, 1989.
Kyte and Doolittle, *J. Mol. Biol.*, 157(1):105-132, 1982.
Lachmann and Efstathiou, *Curr. Opin. Mol. Ther.*, 1(5):622-632, 1999.
Lareyre et al., *J. Biol. Chem.*, 274(12):8282-8290, 1999.
Larsen et al., *Proc. Natl. Acad. Sci. USA*, 83:8283, 1986.
Laspia et al., *Cell*, 59:283, 1989.
Latimer et al., *Mol. Cell. Biol.*, 10:760, 1990.
Lazzeri, *Methods Mol. Biol.*, 49:95-106, 1995.
Lee et al., *DNA Cell Biol.*, 16(11):1267-1275, 1997.
Lee et al., *Environ. Mol. Mutagen.*, 13(1):54-59, 1989.
Lee et al., *Nature*, 294:228, 1981.
Lee et al., *Nucleic Acids Res.*, 12:4191-206, 1984.
Leibowitz et al., *Diabetes*, 48(4):745-753, 1999.
Lesch, *Biol Psychiatry*, 45(3):247-253, 1999.
Levenson et al., *Hum. Gene Ther.*, 9(8):1233-1236, 1998.
Li et al., *Cancer Biol. Ther.*, 2:187-193, 2003b.
Ligocki et al., *J Neuroimmunol.*, September 14; 226(1-2): 192-3, 2010.
Lin et al., *Mol. Cell. Biol.*, 10:850, 1990.
Lovato et al., *Brain.*, Jan. 7, 2011.
Lucchinetti et al., *Ann Neurol.*, June; 47(6):707-17, 2000.
Lundstrom, *J. Recept Signal Transduct. Res.*, 19(1-4):673-686, 1999.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Magliozzi et al., *Ann Neurol.*, October; 68(4):477-93, 2010.
Majors and Varmus, *Proc. Natl. Acad. Sci. USA*, 80:5866, 1983.
Marienfeld et al., *Gene Ther.*, 6(6):1101-1113, 1999.
Mastrangelo et al., *Biotechnol. Bioeng.*, 65(3):298-305, 1999.
McNeall et al., *Gene*, 76:81, 1989.
Miksicek et al., *Cell*, 46:203, 1986.
Miller et al., *J. Pharmacol. Exp. Ther.*, 264:11-16, 1993.
Miyatake et al., *Gene Ther.*, 6:564-572, 1999.
Moldawer et al., *Shock*, 12(2):83-101, 1999.
Mordacq and Linzer, *Genes and Dev.*, 3:760, 1989.
Moreau et al., *Nucl. Acids Res.*, 9:6047, 1981.
Moriuchi et al., *Cancer Res*, 58(24):5731-5737, 1998.
Morrison et al., *J. Gen. Virol.*, 78(Pt 4):873-878, 1997.
Morrison, *Science*, 229(4719):1202-1207, 1985.
Muesing et al., *Cell*, 48:691, 1987.
Nakamura et al., In: *Enzyme Immunoassays: Heterogeneous and Homogeneous Systems*, Chapter 27, 1987.

Naldini et al., *Science*, 272(5259):263-267, 1996.
Neumann et al., *Proc. Natl. Acad. Sci. USA*, 96(16):9345-9350, 1999.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Obermeier et al., *J Neuroimmunol.*, April; 233(1-2):245-8, 2011.
Omirulleh et al., *Plant Mol. Biol.*, 21(3):415-428, 1993.
Ondek et al., *EMBO J.*, 6:1017, 1987.
O'Shannessy et al., *J. Immun. Meth.*, 99, 153-161, 1987.
Owens and Haley, *J. Biol. Chem.*, 259, 14843-14848, 1987.
Palmiter et al., *Cell*, 29:701, 1982.
Parks et al., *J. Virol.*, 71(4):3293-8, 1997.
PCT Appln. WO 92/17598
PCT Appln. WO 94/09699
PCT Appln. WO 95/06128
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Petrof, *Eur Respir J*, 11(2):492-497, 1998.
Pinkert et al., *Genes and Dev.*, 1:268, 1987.
Ponta et al., *Proc. Natl. Acad. Sci. USA*, 82:1020, 1985.
Potrykus et al., *Mol. Gen. Genet.*, 199(2):169-177, 1985.
Potter and Haley, *Meth. Enzymol.*, 91, 613-633, 1983.
Potter et al., *Proc. Natl. Acad. Sci. USA*, 81:7161-7165, 1984.
Queen and Baltimore, Cell, 35:741, 1983.
Quinn et al., *Mol. Cell. Biol.*, 9:4713, 1989.
Reddy et al., *Virology*, 251(2):414-26, 1998.
Redondo et al., *Science*, 247:1225, 1990.
Resendez Jr. et al., *Mol. Cell. Biol.*, 8:4579, 1988.
Rhodes et al., *Methods Mol. Biol.*, 55:121-131, 1995.
Rittling et al., *Nucl. Acids Res.*, 17:1619, 1989.
Robbins and Ghivizzani, *Pharmacol Ther*, 80(1):35-47, 1998.
Robbins et al., *Trends Biotechnol.*, 16(1):35-40, 1998.
Sambrook et al., In: *Molecular cloning: a laboratory manual*, 2$^{nd}$ Ed., Cold Spring Harbor Laboratory Press, Cold Spring Harbor, N.Y., 1989.
Sawai et al. *Mol. Genet. Metab.*, 67(1):36-42, 1999.
Schaffner et al., *J. Mol. Biol.*, 201:81, 1988.
Searle et al., *Mol. Cell. Biol.*, 5:1480, 1985.
Sellebjerg et al., *J Neuroimmunol.*, August 1; 108(1-2):207-15, 2000.
Sellebjerg et al., *J Neurol Sci.*, May 7; 157(2):168-74, 1998.
Sherman et al., *Mol. Cell. Biol.*, 9:50, 1989.
Smith et al., *Neuron.*, 20:1093-1102, 1998.
Spalholz et al., *Cell*, 42:183, 1985.
Stewart et al., *Arch. Biochem. Biophys.* 365:71-74; 1999.
Stowe et al., *Ann Neurol.*, June; 69(6):975-85, 2011.
Stuart et al., *Nature*, 317:828, 1985.
Suzuki et al., *Biochem Biophys Res Commun*, 252(3):686-90, 1998.
Takebe et al., *Mol. Cell. Biol.*, 8:466, 1988.
Tavernier et al., *Nature*, 301:634, 1983.
Taylor et al., *J. Biol. Chem.*, 264:15160, 1989.
Thiesen et al., *J. Virology*, 62:614, 1988.
Tiller et al., *J Immunol Methods.*, January 1; 329(1-2):112-24, 2008.
Timiryasova et al., *Int. J. Oncol.*, 14(5):845-854, 1999.
Trapp et al., *N Engl J Med.*, January 29; 338(5):278-85, 1998.
Tronche et al., *Mol. Biol. Med.*, 7:173, 1990.
Tronche et al., *Mol. Cell. Biol.*, 9:4759, 1989.
Tsukada et al., *Plant Cell Physiol.*, 30(4)599-604, 1989.
Tsumaki et al., *J. Biol. Chem.*, 273(36):22861-22864, 1998.
Tur-Kaspa et al., *Mol. Cell Biol.*, 6:716-718, 1986.
Vanderkwaak et al., *Gynecol Oncol*, 74(2):227-234, 1999.
Vasseur et al., *Proc. Natl. Acad. Sci. USA*, 77:1068, 1980.
Wagner et al., *Proc. Natl. Acad. Sci. USA* 87(9):3410-3414, 1990.
Wang and Calame, Cell, 47:241, 1986.
Wang et al., *Infect. Immun.*, 66:4193-202, 1998.
Wawrzynczak & Thorpe, *Cancer Treat Res.*, 37:239-51, 1988.
Weber et al., *Cell*, 36:983, 1984.
Weihl et al., *Neurosurgery*, 44(2):239-252, 1999.
White et al. *J. Virol.*, 73(4):2832-2840, 1999.
Wilson, *J. Clin. Invest.*, 98(11):2435, 1996.
Wong et al., *Gene*, 10:87-94, 1980.
Wu and Wu, *Adv. Drug Delivery Rev.*, 12:159-167, 1993.
Wu and Wu, *J. Biol. Chem.*, 262:4429-4432, 1987.
Wu et al., *Biochem. Biophys. Res. Commun.*, 233(1):221-226, 1997.
Wu et al., *Cancer Res.*, 58(8): 1605-8, 1998.
Yamada et al., *Brain Res.*, 833(2):302-307, 1999.
Yeung et al., *Gene Ther.*, 6(9):1536-1544, 1999.
Yoon et al., *J. Gastrointest. Surg.*, 3(1):34-48, 1999.
Yurasov et al., *J Exp Med.*, March 7; 201(5):703-11, 2005.
Yutzey et al. *Mol. Cell. Biol.*, 9:1397, 1989.
Zhang et al., *J Autoimmun.*, November-December; 33(3-4): 270-4, 2009.
Zhao-Emonet et al., *Biochim. Biophys. Acta*, 1442(2-3):109-119, 1998.
Zheng et al., *J. Gen. Virol.*, 80(Pt 7):1735-1742, 1999.
Zhou et al., *Nature*, 361(6412):543-547, 1993.
Zufferey et al., *Nat. Biotechnol.*, 15(9):871-875, 1997.

What is claimed is:

1. A recombinant antibody or antigen-binding fragment thereof, wherein the recombinant antibody or fragment comprises:
   (a) heavy chain CDR1 comprising GGAVSNYY (SEQ ID NO: 65), heavy chain CDR2 comprising IYINGTT (SEQ ID NO: 66) and heavy chain CDR3 comprising ARWGALLGDYYYGLDV (SEQ ID NO: 67); and light chain CDR1 comprising QSLLHSNEYIY (SEQ ID NO: 68), light chain CDR2 comprising LAS and light chain CDR3 comprising MQALEAPWT (SEQ ID NO: 69); or
   (b) heavy chain CDR1 comprising GGSINNYY (SEQ ID NO: 70), heavy chain CDR2 comprising IYYNGNI (SEQ ID NO: 71) and heavy chain CDR3 comprising GIGYSAVAAGTVDY (SEQ ID NO: 72); and light chain CDR1 comprising QGISSG (SEQ ID NO: 73), light chain CDR2 comprising DAS and light chain CDR3 comprising QQFNTFPYT (SEQ ID NO: 74).

2. The antibody or fragment of claim 1, wherein said antibody or fragment has a heavy chain variable region comprising SEQ ID NO: 25 and a light chain variable region comprising SEQ ID NO: 47, or a heavy chain variable region comprising SEQ ID NO: 31 and a light chain variable region comprising SEQ ID NO: 35.

3. The recombinant antibody or fragment of claim 1, wherein the recombinant antibody or fragment has mutations at both codon position 40 and codon position 81.

4. The recombinant antibody or fragment of claim 1, wherein the recombinant antibody or fragment has a mutation at codon position 40.

5. The recombinant antibody or fragment of claim 1, wherein the recombinant antibody or fragment has a mutation at codon position 81.

6. The recombinant antibody or fragment of claim 1, wherein the recombinant antibody or fragment has a serine at codon position 40.

7. The recombinant antibody or fragment of claim 1, wherein the recombinant antibody or fragment has an asparagine at codon position 81.

8. The antibody or fragment of claim 1, wherein said recombinant antibody or fragment is linked to a toxin, a drug or a prodrug.

9. The antibody or fragment of claim 1, wherein said recombinant antibody or fragment is linked to a label.

10. The antibody or fragment of claim 9, wherein said label is a chromophore, fluorophore, chemilluminescent compound, dye, contrast agent, or radioabel.

* * * * *